(12) United States Patent
Webber

(10) Patent No.: US 9,822,122 B2
(45) Date of Patent: Nov. 21, 2017

(54) INDOLINE ANALOGS AND USES THEREOF

(71) Applicant: Oncternal Therapeutics, Inc., San Diego, CA (US)

(72) Inventor: Stephen E. Webber, San Diego, CA (US)

(73) Assignee: Oncternal Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/461,327

(22) Filed: Mar. 16, 2017

(65) Prior Publication Data

US 2017/0283420 A1   Oct. 5, 2017

Related U.S. Application Data

(60) Provisional application No. 62/316,156, filed on Mar. 31, 2016, provisional application No. 62/417,621, filed on Nov. 4, 2016.

(51) Int. Cl.
| | |
|---|---|
| *C07D 487/04* | (2006.01) |
| *C07D 209/34* | (2006.01) |
| *C07D 209/38* | (2006.01) |
| *C07D 209/40* | (2006.01) |
| *C07D 401/06* | (2006.01) |
| *C07D 403/06* | (2006.01) |
| *C07D 405/06* | (2006.01) |
| *C07D 409/06* | (2006.01) |
| *C07D 413/06* | (2006.01) |
| *C07D 417/06* | (2006.01) |

(52) U.S. Cl.
CPC ......... *C07D 487/04* (2013.01); *C07D 209/34* (2013.01); *C07D 209/38* (2013.01); *C07D 209/40* (2013.01); *C07D 401/06* (2013.01); *C07D 403/06* (2013.01); *C07D 405/06* (2013.01); *C07D 409/06* (2013.01); *C07D 413/06* (2013.01); *C07D 417/06* (2013.01)

(58) Field of Classification Search
None
See application file for complete search history.

(56) References Cited

U.S. PATENT DOCUMENTS

| | | | |
|---|---|---|---|
| 6,969,729 | B2 | 11/2005 | Jensen et al. |
| 8,232,310 | B2 | 7/2012 | Toretsky et al. |
| 8,232,410 | B2 | 7/2012 | Ojima et al. |
| 9,045,415 | B2 | 6/2015 | Toretsky et al. |
| 9,290,449 | B2 | 3/2016 | Toretsky et al. |
| 9,511,050 | B2 | 12/2016 | Toretsky et al. |
| 9,604,927 | B2 | 3/2017 | Vernier |
| 9,714,222 | B2 | 7/2017 | Toretsky et al. |
| 2002/0016354 | A1 | 2/2002 | Jensen et al. |
| 2005/0288244 | A1 | 12/2005 | Manoharan et al. |
| 2010/0004179 | A1 | 1/2010 | Toretsky et al. |
| 2010/0160260 | A1 | 6/2010 | Skordalakes |
| 2010/0167994 | A1 | 7/2010 | Toretsky et al. |
| 2013/0259927 | A1 | 10/2013 | Nemunaitis et al. |
| 2015/0051260 | A1 | 2/2015 | Toretsky et al. |
| 2015/0329488 | A1 | 11/2015 | Toretsky et al. |
| 2016/0102055 | A1 | 4/2016 | Vernier |
| 2016/0159741 | A1 | 9/2016 | Toretsky et al. |
| 2016/0263086 | A1 | 9/2016 | Toretsky et al. |
| 2017/0065559 | A1 | 3/2017 | Vernier |
| 2017/0066720 | A1 | 3/2017 | Vernier |

FOREIGN PATENT DOCUMENTS

| | | |
|---|---|---|
| CN | 1365972 A | 8/2002 |
| CN | 103435606 | 12/2013 |
| EP | 0133244 A2 | 2/1985 |
| WO | WO 2003/000925 A1 | 1/2003 |
| WO | WO 2006/113864 | 10/2006 |
| WO | WO 2006/117414 A1 | 11/2006 |
| WO | WO 2008/046083 | 4/2008 |
| WO | WO 2008/083326 | 7/2008 |
| WO | WO 2010/083505 | 7/2010 |
| WO | WO 2012/078519 | 6/2012 |
| WO | WO 2013/155341 | 10/2013 |

OTHER PUBLICATIONS

Chemical Abstract Registry No. 1159977-04-4 indexed in the Registry File on STN CAS Online Jun. 25, 2009.*
Abaan et al., "PTPL1 is a direct transcriptional target of EWS-FLI1 and modulates Ewing's sarcoma tumorigenesis", Oncogene (2005) 24(16): 2715-2722.
Allu et al., "Enantioselective organocatalytic adol reaction of unactivated ketones with isatins," Tetrahedron Letters 52:4080-4083 (2011).
Anderson et al., "BRCA1 protein is linked to the RNA polymerase II holoenzyme complex via RNA helicase A", Nat Genet (1998) 19(3):254-256.
Ankhiwala, Studies in Spiroheterocycles. Synthesis and Antimicrobial Activities of Some New Spiro (indoline-3, 5'-pyrazonlin)-1'-phenyl-2-ones and Spiro ( . . . J Indian Chem Soc. (1990) 67: 432-434.
Babu et al., "Heteropolyacid-silica mediated [3+2] cycloaddition of ylides—a facile multicomponent one-pot synthesis of novel dispiroheterocycles", Tetrahedron Ltt. (2006) 47(52): 9221-9225.
Baer et al., "Profiling and functional annotation of mRNA gene expression in pediatric rhabdomyosarcoma and Ewing's sarcoma", Int J Cancer (2004) 110(5):687-694.
Bayoumy et al., "Studies on Spiroheterocyclic Nitrogen Compounds. Part 1: Synthesis of Some New Spiro Pyrazolines, Isoxazolines and Pyrimidinethiones Containing Benzailide Moiety," J Indian Chem Soc. 61:520-522 (1984).

(Continued)

*Primary Examiner* — Matthew Coughlin
*Assistant Examiner* — Po-Chih Chen
(74) *Attorney, Agent, or Firm* — Knobbe, Martens, Olson & Bear, LLP

(57) ABSTRACT

Indoline derivative compounds that act as EWS-FLI1 transcription factor inhibitors are provided. Also provided are pharmaceutical compositions of the indoline derivatives, methods of synthesizing the same, methods of treating using same, and assays for identifying the inhibitors of EWS-FLI1 oncoprotein.

10 Claims, 41 Drawing Sheets

(56) References Cited

OTHER PUBLICATIONS

Beccalli et al., "Synthesis of [a]annulated carbazoles from indol-2,3-dione." Tetrahedron (1993) 49(21): 4741-4758.
Becerra et al., "Hydrogen-bonding patterns in 3-alkyl-3-hydroxyindolin-2-ones," Acta Cryst C66:o79-o86 (2010).
Berg et al., "Small-molecule antagonists of Myc/Max dimerization inhibit Myc-induced transformation of chicken embryo fibroblasts", Proc Natl Acad Sci U S A (2002) 99(6):3830-3835.
Bhalla et al., "Local flexibility in molecular function paradigm", Mol Cell Proteomics (2006) 5:1212-1223.
Bowdish et al., "Immunomodulatory properties of defensins and cathelicidins", Curr Top Microbiol Immunol (2006) 306:27-66.
Braun et al., "Identification of target genes for the Ewing's sarcoma EWS/FLI fusion protein by representational difference analysis", Mol Cell Biol (1995) 15(8):4623-4630.
Byler et al, "Identification of benzoylisoquinolines as potential anti-Chagas agents," J Bioorg Med Chem 20:2587-2594 (2012).
Carter et al., "Chemotherapy of Cancer", 2nd Edition; John Wiley & Sons, New York (1981), Appendix C—Drug-Tumor Interactions; 5 pages.
Castillero-Trejo et al., "Expression of the EWS/FLI-1 oncogene in murine primary bone-derived cells results in EWS/FLI-1-dependent, Ewing sarcoma-like tumors", Cancer Res (2005) 65(19):8698-8705.
Chen et al., "Specific alterations of U1-C protein or U1 small nuclear RNA can eliminate the requirement of Prp28p, an essential DEAD box splicing factor", Mol Cell (2001) 7(1):227-232.
Chen et al, "Catalyst-free aldol condensation of ketones and isatins under mild reaction conditions in DMF with molecular sieves 4 A as additive," Green Chem 11:1465-1476 (2009).
Cheng et al., "Rational drug design via intrinsically disordered protein", Trends Biotechnol. (2006) 24(10):435-442.
Dandia et al., "Investigation of the Reactions of some New Fluorine containing 3-Aroylmethylene-indol-2-ones with Urea and Thiourea Derivatives", J Indian Chem Soc., (Nov. 1995) 72: 833-835.
Dandia et al., "Facile One Pot Microwave Induced Solvent-Free Synthesis and Antifungal, Antitubercular Screening of Spiro [1,5]-Benzothiazepin-2,3'[3'H]indol-2[1'H]-ones", Chem Pharm Bull (2003) 51(10): 1137-1141.
Database accession No. CID 359736, 3-[2-(4-Amino-phenyl)-2-oxo-ethyl]-3-hydroxy-1,3-dihydro-indol-2-one—Compound Summary; (Mar. 26, 2005) XP-002717179; Database PubChem Compound; pp. 1-5
Database accession No. CID 326411; NSC297830—Compound summary; XP-002717181; (Mar. 26, 2004) Database PubChem Compound; pp. 1-5.
Database accession No. RN 362506-54-5; XP-002745329; (Oct. 16, 2001) Supplier: ChemBridge Corporation; 1 page.
Database accession No. RN 362507-29-7; XP-002745330; (Oct. 16, 2001) Supplier: Interbioscreen Ltd.; 1 page.
Database accession No. CID 366668, NSC635343—Compound summary; XP-002717180; (Mar. 26, 2005) Database PubChem Compound; pp. 1-3.
Database accession No. CID 366694, NSC635411—Compound summary; (Mar. 6, 2005) Database PubChem Compound; pp. 1-3.
Database accession No. CID 398900, NCI60_038544—Compound summary; (May 30, 2009) Database PubChem Compound; pp. 1-2.
Database accession No. CID 703160, ZINC00085926—Compound summary; (Jul. 8, 2005) Database PubChem Compound; pp. 1-2.
Database accession No. CID 772922, ZINC00257314—Compound summary; (Jul. 8, 2005) Database PubChem Compound; pp. 1-2.
Database accession No. CID 797457, ZINC00302255—Compound summary; (Jul. 9, 2005) Database PubChem Compound; pp. 1-2.
Database accession No. CID 797741, ZINC00302664—Compound summary; (Jul. 9, 2005) Database PubChem Compound; pp. 1-2.
Database accession No. CID 1149577, ZINC00894999—Compound summary; (Jul. 10, 2005) Database PubChem Compound; pp. 1-2.
Database accession No. RN 1144428-37-4; XP-002745331; (May 8, 2009) Supplier: Interbioscreen Ltd.; 1 page.
Database accession No. CID 1517002, ZINC01439946—Compound summary; (Jul. 11, 2005) Database PubChem Compound; pp. 1-2.
Database accession No. CID 51703682, ZINC35686355—Compound summary; (May 5, 2011) Database PubChem Compound; pp. 1-2.
Delattre et al., "The Ewing family of tumors—a subgroup of small-round-cell tumors defined by specific chimeric transcripts", N Engl J Med (1994) 331(5):294-299.
DeMichelis et al., TMPRSS2: ERG gene fusion associated with lethal cancer in a watchful waiting cohort, Oncogene (2007) 26:4596-4599.
DeRossi et al., "The third helix of the Antennapedia homeodomain translocates through biological membranes", J Biol Chem (1994) 269(14):10444-10450.
El-Gendy et al., "Synthesis and Antimicrobial Activity of some New 2-Indolinone Derived Oximes and Spiro-Isoxazolines," Arch Pharm Res 23(4):310-314 (2000).
Erkizan et al, "A small molecule blocing oncongenic protein EWS-FLI1 interaction with RNA helicase A inhibits growth of Ewing's sarcoma," Nature Medicine 15(7):750-757 (2009).
Feldmann et al., "Blockage of hedgehog signaling inhibits pancreatic cancer invasion and metastases: A new paradigm for combination therapy in solid cancers", Cancer Res. (2007) 67:2187-2196.
Frangioni et al., "Use of a general purpose mammalian expression vector for studying intracellular protein targeting: identification of critical residues in the nuclear lamin A/C nuclear localization signal", J Cell Sci (1993) 105(Pt. 2):481-488.
French et al., "Midline carcinoma of children and young adults with NUT rearrangement", J Clin Oncol (2004) 22(20):4135-4139.
Fujii et al., "An antagonist of dishevelled protein-protein interaction suppresses beta-catenin-dependent tumor cell growth", Cancer Res (2007) 67(2):573-579.
Gadek et al., "Small molecule antagonists of proteins", Biochem Pharmacol (2003) 65(1):1-8.
Gangwal et al., "Microsatellites as EWS/FLI response elements in Ewing's sarcoma", Proc Natl Acad Sci U S A (2008) 105(29):10149-10154.
Garden et al., "A versatile synthetic methodology for the synthesis of tryptophols", Tetrahedron (2002) 58(42):8399-8412.
Grier et al., "Addition of ifosfamide and etoposide to standard chemotherapy for Ewing's sarcoma and primitive neuroectodermal tumor of bone", N Engl J Med (2003) 348(8):694-701.
Grigg et al., "Silver Acetate Catalysed Cycloadditions of Isocyanoacetates," Tetrahedron 55:2025-2044 (1999).
Golub et al., "Molecular Classsification of Cancer: Class Discovery and Class Prediction by Gene Expression Monitoring", Science (1999) 286: 531-537.
Guo et al: "Quinidine Thiourea-catalyzed Aldol Reaction of Unactivated Ketones: Highly Enantioselective Synthesis of 3-Alkyl-3-hyroxy-indolin-2-ones," Angew Chem Int Ed 49:9460-9464 (2010).
Gyurkocza et al., "Antileukemic activity of shepherdin and molecular diversity of hsp90 inhibitors", J Natl Cancer Inst (2006) 98(15):1068-1077.
Hartman et al., "RNA helicase a is necessary for translation of selected messenger RNAs", Nat Struct Mol Biol. (2006) 13:509-516.
Helman et al., "Mechanisms of sarcoma development", Nat Rev Cancer (2003) 3(9):685-694.
Hu-Lieskovan et al., "Sequence-specific knockdown of EWS-FLI1 by targeted, nonviral delivery of small interfering RNA inhibits tumor growth in a murine model of metastatic Ewing's sarcoma", Cancer Res (2005) 65:8984-8992.
Ibrahim et al., "Synthesis of Spiro Heterocyclic Compounds", E-Journal of Chem. (2010) 7(1):55-58.
Iost et al., "mRNAs can be stabilized by DEAD-box proteins", Nature (1994) 372(6502):193-196.
Joshi et al., "Synthesis and central nervous system activities of certain fluorine-containing 3-substituted indol-2-ones." Pharmazie (1984) 39(3): 153-155.

(56) References Cited

OTHER PUBLICATIONS

Josh et al., "Studies in Spiro Hetercycles: Part 4: Investigation of the Reactions of Fluroinated 3-Aroylmethylene-indol-2-ones with Hydrazine and Phenylhydrazine and Synthesis of Spiro [indole3,3'-pyrazol]-2-ones," Pharmazie 40:21-22 (1985).

Joshi et al., "Studies in Spiroheterocycles: Part XXVIII: Investigation of the Reaction of 3-Aroylmethyleneindolin-2-Ones with Thiosemicarbazide and Synthesis of SPIRO[3H-INDOLE-3,4'(3'H)-PYRIMIDIN]-2(1H)-Ones," Heterocycles 31(3):473-477 (1990).

Joshi et al., "Investigation of the reaction of 1,3-dihydro-3-(20phenyl-2-oxoethylidene)-indol-2(H)-ones with 3-amino-1-phenyl-2-pyrazolin-5-one," Indian J Chem 29B:933-936 (1990).

Joshi et al., "Synthesis and Antibacterial Activity of some Novel Fluorine containing Sipro[3H-indole-3,3'-'3H]-pyrazol]-2(1H)-one Derivatives," J Indian Chem Soc. 67:753-756 (1990).

IUPAC-IUB [Inter'l Union of Pure and Applied Chemistry-Inter'l Union of Biochemistry] Commission of Biochemical Nomenclature. Appreviated nomenclature of synthetic polypeptides (polymerized amino acids). Revised Recommentations (1971); Biochem. (1972) 11(5):942-944.

Kaiser, J., "First Pass at Cancer Genome Reveals Complex Landscape", Sciene (2006) 94 313:1370.

Khan et al., "Classification and diagnostic prediction of cancers using gene expression profiling and artificial neural networks", Nat Med (2001) 7(6):673-679.

Kidwai et al., "Microwave-induced "solvent-free" novel technique for the synthesis of spiro [indole-pyrazole/isoxazole/pyrimidine] derivatives", Oxidation Communications (2001) 24(2):287-290.

Kinsey et al., "NROB1 is required for the oncogenic phenotype mediated by EWS/FLI in Ewing's sarcoma", Mol Cancer Res (2006) 4(11):851-859.

Klöck et al., "Acylideneoxoindoles: A new class of reversible inhibitors of human transglutaminase 2," J Bioorg Med Chem Lett 21:2692-2696 (2011).

Knoop et al., "The splicing factor U1C represses EWS/FLI-mediated transactivation", J Biol Chem (2000) 275(32):24865-24871.

Knoop et al., "EWS/FLI alters 5'-splice site selection", J Biol Chem (2001) 276(25):22317-22322.

Kobayashi et al., "Studies on Indole Derivatives. I. Synthesis of 3-Phenyl-9H-pyridazino[3,4-b]indole Derivatives," Chem Pharm Bull 12(10):1129-1135 (1964).

Kovar et al., "EWS/FLI-1 antagonists induce growth inhibition of Ewing tumor cells in vitro", Cell Growth Differ (1996) 7(4):429-437.

Kovar et al., "Potentials for RNAi in sarcoma research and therapy: Ewing's sarcoma as a model", Semin Cancer Biol. (2003) 13:275-281.

Krontiris et al., "Internal Medicine", 4th Edition, Elsevier Science (1994) Chapters 71-72, pp. 699-729.

Lala et al., "Role of nitric oxide in tumor progression: Lessons from experimental tumors", Cancer Metastasis Rev. (1998) 17(1): 91-106.

Lambert et al., EWS FLI-1 antisense nanocapsules inhibits Ewing sarcoma-related tumor in mice, Biochem Biophys Res Commun. (2000) 279(2):401-406.

Lang et al., "Identification of peptide mimetics of xenoreactive alpha-Gal antigenic epitope4 by phage display", Biochem Biophys Res Commun (2006) 306:27-66.

Lee et al., "RNA helicase A is essential for normal gastrulation", Proc Natl Acad Sci U S A (1998) 95(23):13709-13713.

Leeson et al., "The influence of drug-like concepts on decision-making in medicinal chemistry", Nature reviews (2007) 6(11):881-890.

Lessnick et al., "The Ewing's sarcoma oncoprotein EWS/FLI induces a p53-dependent growth arrest in primary human fibroblasts", Cancer Cell (2002) 1(4):393-401.

Li et al., "Control of apoptosis and mitotic spindle checkpoint by survivin", Nature (1998) 396(6711):580-584.

Lindgren et al., "Translocation properties of novel cell penetrating transportan and penetratin analogues", Bioconjug Chem (2000) 11(5):619-626.

Liu et al., "Organocatalytic asymmetric synthesis of 3-difluoroalkyl 3-hyrdrozyoxindoles" Chem Commun 48:1919-1921 (2012).

Lopez-Alvarado et al., "New Diastereoselective Synthesis of 3-Alkyidene-1-methyloxindoles" Synthesis 1:104-110 (2002).

Lu et al., "Synthesis of planar chiral [2.2] paracyclophane-based amino thioureas and their application in asymmetric aldol reactions of ketones with isatins" Tetrahetron 24:1082-1088 (2013).

Lutz et al., "Acid-Catalyzed Rearrangements of the y-(Methylanilino)lactone of cis-B(p-Bromobenzoyl)-B-methylacrylic Acid, and of trans-b-(p-Bromobenzoyl)acrykuc Methylanilide, to Oxindoles," J Organ Chem 25(1):193-196 (1960).

Macaev et al., "Synthesis and Structure of New Oxoindoles," Chem Hetero Compounds 43(3) 298-305 (2007).

Maitra et al., "Detection of t(11;22)(q24;q12) Translation and EWS-FLI-1 Fusion Transcript in a Case of Solid Pseudopapillary Tumor of the Pancreas", Ped Develop Pathol. (2000) 3:603-605.

Maksimenko et al., "Oligonucleotides targeted against a junction oncogene are made efficient by nanotechnologies", Pharm Res (2003) 20(10):1565-1567.

Mateo-Lozano et al.; Rapamycin induces the fusion-type independent downregulation of the EWS/FLI-1 proteins and inhibits Ewing's sarcoma cell proliferation; Oncogene (2003) 22(58):9282-9287.

May et al., "Ewing sarcoma 11;22 translocation produces a chimeric transcription factor that requires the DNA-binding domain encoded by FLI1 for transformation", Proc Natl Acad Sci U S A (1993) 90(12):5752-5756.

May et al., "The Ewing's sarcoma EWS/FLI-1 fusion gene encodes a more potent transcriptional activator and is a more powerful transforming gene than FLI-1", Mol Cell Biol (1993) 13(12):7393-7398.

McIntyre et al., "Design and cloning strategies for constructing shRNA expression vectors", BMC Biotechnol. (2006) 6:1.

MEDLINEPLUS; Cancer [online]; [retrieved on Jul. 6, 2007] URL—http://www.nlm.nik.gov/medlineplus/cancer.html. 10 pages.

Merchant et al., "Potential use of imatinib in Ewing's sarcoma: evidence for in vitro and in vivo activity", J Natl Cancer Inst (2002) 94(22):1673-1679.

Merchant et al., Interferon gamma enhances the effectiveness of tumor necrosis factor-related apoptosis—Inducing ligand receptor agonists in a xenograft model of Ewing's i ;'sarcoma, Cancer Res (2004) 64(22):8349-8356.

Mhawech-Fauceglia et al., "Friend leukaemia integration-1 expression in malignant and benign tumours: a multiple tumour tissue microarray analysis using polyclonal antibody", J i Clin Path. (2007) 60(6):694-700.

Murray et al., "Targeting protein-protein interactions: Lessons from p53/MDM2", Biopolymers (2007) 88(5):657-686.

Myohanen et al., "Sequence-specific DNA binding activity of RNA helicase A to the p16INK4a promoter", J Biol Chem (2001) 276(2):1634-1642.

Nagle et al., "3-(2-Oxoethylidene)indolin-2-one Derivatives Activate Nrf2 and Inhibit NF-xB: Potential Candidates for Chemoprevention," ChemMedChem 9:1763-1774 (2014).

Nakajima et al., "RNA helicase A mediates assocation of CBP with RNA polymerase II", Cell (1997) 90(6):1107-1112.

Nakatani et al., "Identification of p21WAF1/CIP1 as a direct target of EWS-Fli1 oncogenic 132 fusion protein", J Biol Chem (2003) 278(17):15105-15115.

National Center for Biotechnology Information. (PubChm Substance Database; SID=862348, (https://pubchem.ncbi.nlm.nih.gov/substance/862348; downloaded Jan. 2, 207); available Jun. 29, 2005; 8 pages.

Ng et al., "Multiple aromatic side chains within a disordered structure are critical for transcription and transforming activity of EWS family oncoproteins", Proc Natl Acad Sci U S A (2007) 104(2):479-484.

Ojida et al., "Highly enantioselective reformatsky reaction of ketones: Chelation-assisted enantioface discrimination", Org Lett (2002) 4(18):3051-3054.

(56) References Cited

OTHER PUBLICATIONS

Ouchida et al., "Loss of tumorigenicity of Ewing's sarcoma cells expressing antisense RNA to EWS-fusion transcripts", Oncogene (1995) 11(6):1049-1054.
137 Pagliaro et al., "Emerging classes of protein-protein interaction inhibitors and new tools for their development", Curr Opin Chem Biol. (2004) 8(4):442-449.
Pajouhesh et al., Potential Anticonvulsants VI: Condensation of Isatins with Cyclohexanone and other Cyclic Keytones, J Pharm Sci 72(3):318-321 (1983).
Palermo et al., "The AF4-mimetic peptide, PFWT, induces necrotic cell death in MV4-11 leukemia cells", Leuk Res. (2008) 32(4):633-42.
Perez et al., "Antennapedia homeobox as a signal for the cellular internalization and nuclear addressing of a small exogenous peptide", J Cell Sci (1992) 102(Pt. 4):717-722.
Petermann et al., "Oncogenic EWS-Fli1 interacts with hsRPB7, a subunit of human RNA polymerase II", Oncogene (1998) 17:603-610.
Pietra et al., "The stereochemistry of propiophenone addition to isatin," Gazzetta Chimica Italiana 92(XII): 1422-1431 (1962).
Plescia et al., "Rational design of shepherdin, a novel anticancer agent" Cancer Cell (2005) 7(5):457-468.
Popp et al., "Synthesis of 3-Hydroxy-3-phenacyloxindole Analogs", J Pharma Science (1979) 68(4):519-520.
Poppe et al., "Expression analyses identify MLL as a prominent target of 11q23 amplification and support an etiologic role for MLL gain of function in myeloid malignancies", Blood (2004) 103(1):229-235.
Pui et al., "Clinical heterogeneity in childhood acute lymphoblastic leukemia with 11q23 rearrangements", Leukemia (2003) 17(4):700-706.
Pui et al., "Acute lymphoblastic leukemia", N Engl J Med (2004) 350(15):1535-1548.
Rahim et al., "YK-4-279 Inhibits ERG and ETV1 Mediated Prostate Cancer Cell Invasion", PLoS One (2011) 6(4):e19343; 8 pages.
Registry File(STN), downloaded on Oct. 6, 2016; RN:1180038-32-7; 1146930-25-7; 1144428-37-4; 634174-66-6; 1144428-37-4; 634174-66-6; 442567-87-5; 421584-34-1; 421579-15-9; 149;421578-89-4; 385394-59-2; 383893-83-2; 370850-15-0; 370848-38-7; 369395-93-7; 36250729-7, and 362506-54-5; 8 pages.
Registry File(STN), published Aug. 6, 2002, RN:442639-80-7; 1 page.
"Remington's Pharmaceutical Sciences", Mack Publishing Company 19th edition (1995).
Richter et al, "Diazepam-bound $GABA_A$ receptor models identify new benzodiazepine binding-site ligands," Nature 8:455-464 (2012).
Riggi et al., "Ewing's sarcoma—Like tumors originate from EWS-FLI-1-expressing mesenchymal progenitor cells", Cancer Res (2006) 66(19):9786.
Righetti et al., "Heterodiene Syntheses. Part 21. etc.", J Chem Soc., Perkin Transactions I, (1979) 4: 863-868.
RN 667914-27-4 (Registry, 2H-Indol-2-one, 3-[2-(4-aminophenyl)-2-oxoethyl]-5, 7-dichloro-1, 3-dihydro-3-hydroxy, Mar. 26, 2004); 1 page.
RN 667914-33-2 (Registry, 2H-Indol-2-one, 4, 7-dichloro-3-[2-(4-aminophenyl)-2-oxoethyl]-1, 3-dihydro-3-hydroxy, Mar. 26, 2004); 1 page.
RN 672338-27-1 (Registry, 2H-Indol-2-one, 4, 6-dichloro-1, 3-dihydro-3-hydroxy-3-[2-(3-nitrophenyl)-2-oxoehyl], Apr. 7, 2004); 1 page.
RN 6938523-27-7 (Registry, 2H-Indol-2-one, 7-bromo-1,3-dihydro-3-hydroxy-3-[2-(4-methoxyphen1)-2-oxoethyl]-5-methyl, Jun. 16, 2004); 1 page.
RN 848688-25-5 (Registry, 2H-Indol-2-one, 4,6-dichloro-3-[2-(2, 4-dimethoxyphenyl)-2-oxoethyl]-1, 3-dihydro-3-hydroxy, Apr. 18, 2005); 1 page.

RN 900016-35-5 (Registry, 2H-Indol-2-one, 7-chloro-1, 3-dihydro-3-hydroxy-3-[2-oxo-2-(3,4,5-trimethoxyphenyl) ethyl, Aug. 9, 2006); 1 page.
RN 909225-77-0 (Registry, 2H-Indol-2-one, 7-chloro-3-[2-(4-ethylpheny1)-2-oxoethyl]-1,3-hydroxy, Oct. 2, 2006); 1 page.
RN 692281-43-9 (Registry, 2H-Indol-2-one, 4-chloro-3-[2-(4-fluorophenyl)-2-oxoethy1]-1,3-dihydro-3-hydroxy-7-methyl, Jun. 13, 2004); 1 page.
RN 848755-10-2 (Registry, 2H-Indol-2-one4,6-dichloro-3-[2-(3,4-dimethoxypheny1)-2-oxoethy1)-1,3-dihydro-3-hydroxy, Apr. 19, 2005); 1 page.
Saidalimu et al., "Highly Antioselective Construction of 3-Hyrdoxy Oxindoles through a Decarboxylative Aldol Additional Trifuoromethyl a-Fluorinated gen-diols to N-Benzyl Isatins," Agnew Chem Int. Ed 52:5566-5570 (2013).
Sanchez et al., "Alteration of cyclin D1 transcript elongation by a mutated transcription factor up-regulates the oncogenic D1b splice isoform in cancer", Proc Natl Acad Sci U S A. (2008) 105(16):6004-6009.
Segura-Cabrera et al., "Structure-based prediction of Mycobacterium tuberculosis shikimate kinase inhibitors by high-throughput virtual screening," Bioorg Med Chem Lett :18:3152-3157 (2008).
Sillerud et al., "Design and structure of peptide and peptidomimetic antagonists of protein-protein interaction", Curr Protein Pept Sci (2005) 6(2):151-169.
Smith et al., "Expression profiling of EWS/FLI identifies NKX2.2 as a critical target gene in Ewing's sarcoma", Cancer Cell (2006) 9(5):405-416.
Snyder et al., "Treatment of terminal peritoneal carcinomatosis by a transducible p53-activating peptide", PLos Biol (2004) 2(2):0186-0193.
Srinivasan et al., "The synthetic peptide PFWT disrupts AF4-AF9 protein complexes and induces apoptosis in t(4;11) leukemia cells", Leukemia (2004) 18(8):1364-1372.
Stegmaier et al., "Signature-based small molecule screening identifies cytosine arabinoside as an EWS/FLI modulator in Ewing sarcoma", PLoS medicine (2007) 4(4):e122.
Strigacova et al., "Novel oxindole derivatives and their biological activity", Folia Microbiol (Praha). (2001) 46(3):187-192.
Subramanian et al., "Gene set enrichment analysis: a knowledge-based approach for interpreting genome-wide expression profiles", Proc Natl Acad Sci U S A. (2005) 102(43):15545-15550.
Tanaka et al., "EWS-FLI1 antisense oligodeoxynucleotide inhibits proliferation of human Ewing's sarcoma and primitive neuroectodermal tumor cells", J Clin Invest (1997) 99(2):239-247.
Terrone et al., "Penetratin and related cell-penetrating cationic peptides can translocate across lipid bilayers in the presence of a transbilayer potential", Biochem. (2003) 42(47):13787-13799.
Tetsuka et al., "RNA helicase A interacts with nuclear factor kappaB p65 and functions as a transcriptional coactivator", Eur J Biochem (2004) 271(18):3741-3751.
Thoren et al., "The antennapedia peptide penetratin translocates across lipid bilayers—the first direct observation", FEBS Lett (2000) 482(3):265-268.
Tiemann et al., "Solid pseudopapillary neoplasms of the pancreas are associated with FLI-1 expression, but not with EWS/FLI-1 translocation." Mod Pathol. (2006) 19(11):1409-1413.
Torchia et al., "EWS/FLI-1 induces rapid onset of myeloid/erythroid leukemia in mice", Mol Cell Biol (2007) 27(22):7918-7934.
Toretsky et al., "Inhibition of EWS-FLI-1 fusion protein with antisense oligodeoxynucleotides", J Neurooncol. (1997) 31(1-2):9-16.
Toretsky et al., "Phosphoinositide 3-hydroxide kinase blockade enhances apoptosis in the Ewing's sarcoma family of tumors", Cancer Res (1999) 59(22):5745-5750.
Toretsky et al., "Glypican-3 expression in Wilms tumor and hepatoblastoma", J Pediatr Hematol Oncol. (2001) 23(8):496-499.
Toretsky et al., "Oncoprotein EWS-FLI1 activity is enhanced by RNA helicase A", Cancer Res (2006) 66(11):5574-5581.
Üren et al., "Recombinant EWS-FLI1 oncoprotein activates transcription", Biochem. (2004) 43(42):13579-13589.

(56) References Cited

OTHER PUBLICATIONS

Üren et al., "Activation of the canonical Wnt pathway during genital keratinocyte transformation: a model for cervical cancer progression", Cancer Res (2005) 65(14):6199-6206.
Üren et al., "Ewing's Sarcoma Oncoprotein EWS-FLI1: The Perfect Target without a Therapeutic Agent", Future Onc. (2005) 1(4):521-528.
Üren et al., "Pediatric malignancies provide unique cancer therapy targets", Curr Opin Pediatr. (2005) 17:14-19.
Välineva et al., "Characterization of RNA helicase A as component of STAT6-dependent enhanceosome", Nucleic Acids Res (2006) 34(14):3938-3946.
Velikorodov et al., "Some Condensations of Methyl 4-Acetylphenylcarbamate", Russian J Org Chem (2010) 46(7):971-975.
Velikorodov et al., "Synthesis of New Spiro Compounds Containing a Carbamate Group", Russian J Org Chem. (2010) 46(12):1826-1829.
Velikorodov et al., "Synthesis of 3-Pyrrol-3'-yloxindoles with a Carbamate Function", Russian J Org Chem. (2011) 47(11):1715-1717.
Velikorodov et al., "L-Proline-Catalyzed 1,3-Dipolar Cycloaddition of Some Schiff Bases to Methyl 4-[1-Oxo-2(2-oxo-2,3-dihydro1H-indol-3-ylidene)ethyl]phenylcarbamate", Russian J Org Chem. (2011) 47(10)1596-1597.
Velikorodov et al., "Three-Component Synthesis of Spiro Compounds with a Carbamate Functionality", Russian J Org Chem. (2011) 47(3):402-404.
Von Hippel et al., "A general model for nucleic acid helicases and their "coupling" within macromolecular machines", Cell (2001) 104(2):177-190.
Walensky et al., "Activation of apoptosis in vivo by a hydrocarbon-stapled BH3 helix", Science (2004) 305(5689):1466-1470.
Wikipedia—Cancer [online]; [retrieved on Jul. 6, 2007]. URL; http://en.wikipedia.org/wiki/Cancer; 2 pages.
Xie et al., "Functional anthology of intrinsic disorder. 1. Biological processes and functions of proteins with long disordered regions", J Proteome Res. (2007) 6(5):1882-1898.
Yin et al., "Low molecular weight inhibitors of Myc-Max interaction and function", Oncogene (2003) 22(40):6151-6159.
Yu et al., "Highly Efficient "On Water" Catalyst-Free Neucleophilic Addition Reactions Using Difluoroenoxysilanes: Dramatic Flourine Effects," Agnew Chem Int. Ed 53:9512-9516 (2014).
Zhang et al., "Multiple functions of nuclear DNA helicase II (RNA helicase A) in nucleic acid metabolism", Acta Biochim Biophys Sin (Shanghai) (2004) 36(3):177-183.
Zhong et al., "RNA helicase A in the MEF1 transcription factor complex upregulates the MDR1 gene in multidrug-resistant cancer cells", J Biol Chem (2004) 279(17):17134-17141.
Zhong et al., "Molecular sieve mediated decarboxylative Mannich and aldol reactions of B-ketoacids," Tetrahedron Letters 54:4333-4336 (2013).
Chemical Abstract compound, STN express; RN-340220-38-4 (Entered STN: Jun. 10, 2001); 1 Page.
Chemical Abstract compound, STN express; RN-908809-06-3 (Entered STN: Sep. 27, 2006); 1 Page.
Gupta et al., "Ordered short channel mesoporous silica modified with 1,3,5-triazine-piperazine as a versatile recyclable basic catalyst for cross-aldol, Knoevenagel and conjugate addition reactions with isatins", RSC advances, (2015) 5(23): 17843-17850.
Yong et al., "Synthesis of novel 3' -spirocycline-oxindole derivatives and assessment of their cytostatic activities", Tetrahedron (2007) 63(25): 5579-5586.
International Search Report and Written Opinion dated Jun. 27, 2017 for International Patent Application No. PCT/US2017/022682, filed Mar. 16, 2017.

\* cited by examiner

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

TC71 (Type 1, 7/6)

SKES (Type 2, 7/5)

A4573 (Type 3, 10/6)

US 9,822,122 B2

INDOLINE ANALOGS AND USES THEREOF

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/316,156, filed on Mar. 31, 2016 and U.S. Provisional Application No. 62/417,621, filed on Nov. 4, 2016. Each of the aforementioned applications is incorporated by reference herein in its entirety, and each is hereby expressly made a part of this specification.

BACKGROUND

Field

Indoline analog compounds that act as EWS-FLI1 transcription factor inhibitors are provided. Also provided are pharmaceutical compositions of the indoline analogs, methods of synthesizing the same, methods of treating using same, and assays for identifying the inhibitors of EWS-FLI1 oncoprotein.

Description

The EWS-FLI transcription factor present in vast variety of Ewing's sarcoma family of tumors (ESFT) was characterized over ten years ago. Progress in the treatment of Ewing's sarcoma the second most common bone tumor in children and adolescents, has improved survival for patients with localized tumors. However, patients with metastases still fare badly and the therapy carries short and long-term toxicities. The Ewing sarcoma family of tumors (ESFT) is characterized by a chromosomal translocation that generates EWS-FLI1, on oncogenic fusion transcription factor whose continued expression is believed to be critical for ESFT cell survival (Balamuth, N J, Womer, R B, Lancet Oncology 11, 184-192 (2010)).

In vitro and in vivo studies have demonstrated that the inhibition of the binding of the oncoprotein, EWS-FLI1, to RNA Helicase A (RHA) leads to a decrease in proliferation of ESFT cell lines and a decrease of tumor volume. EWS-FLI1 lacks enzymatic activity, however, the protein-protein interaction between RNA helicase A (RHA) and EWS-FLI1-modulates oncogenesis, and is therefore required for the maintenance of the tumor growth (Hyariye N Erkizan et al. Nature Medicine 15(7) 750-756 (2009)). The paradigm of disrupting key protein interactions may have utility in treatment of diseases including sarcomas with similar translocations, and leukemias with MLL translocations ((Helman L J, Meltzer P. Mechanisms of sarcoma development. Nat Rev Cancer 2003; 3(9):685-94); and Pui C H, et al., N Engl J Med 2004; 350(15):1535-48). Moreover, disordered proteins may be excellent therapeutic targets based on their intrinsic biochemical properties (Cheng Y, LeGall T, Oldfield C J, et al., Trends Biotechnol 2006; 24(10):435-42).

SUMMARY

Despite years of in vitro and xenograft studies with antisense and siRNA directed towards EWS-FLI1, none of these is heretofore practical as a human therapy based on inadequate delivery and stability. Accordingly, there is a need for improved therapies to treat disorders such as ESFTs.

FLI-1 is a member of the ETS family transcription factors which are normally active in the developing embryo, but not after birth. There are 29 members of this family of transcription factors, four of which, FLI-1, ETV1, ETV4 and ERG, have been associated with a wide range of cancers.

Therapeutic compounds targeting the inhibition of the binding of oncogenic fusion proteins of FLI1, ETV1, ETV4 or ERG or the transcription factors themselves will have utility in treatment of cancers including the Ewing's sarcoma family of tumors, pancreatic cancer, prostate cancer, glioblastoma, non-small cell lung cancer, and several other cancers. The preferred embodiments fulfill these needs, and provide other advantages as well.

Some embodiments disclosed herein relate to a compound of Formulae (I)-(VII) described herein, including forms such as stereoisomers, free forms, pharmaceutically acceptable salts or esters thereof, solvates, or combinations of such forms.

Some embodiments disclosed herein relate to methods for treating cancer in a mammal, comprising administering to the mammal an effective amount of one or more compounds of Formulae (I)-(VII) including forms such as stereoisomers, free forms, or a pharmaceutically acceptable salt thereof, or a pharmaceutical composition that includes one or more compounds of Formulae (I)-(VII) including forms such as stereoisomers, free forms, or a pharmaceutically acceptable salt thereof. Other embodiments described herein relate to using one or more compounds of Formulae (I)-(VII) including forms such as stereoisomers, free forms, or a pharmaceutically acceptable salt thereof, in the manufacture of a medicament for treatment of cancer.

Still other embodiments described herein relate to a compound of Formulae (I)-(VII) including forms such as stereoisomers, free forms, or a pharmaceutically acceptable salt thereof, for treatment of cancer wherein the cancer is selected from the group consisting of Ewing's sarcoma, glioblastoma, acute myeloid leukemia, breast cancer, head & neck cancer, melanoma, non-small cell lung cancer, ovarian cancer, prostate cancer, and uterine cancer. These and other embodiments are described in greater detail below.

DESCRIPTION OF THE DRAWINGS

FIG. 1A provides data for growth inhibition of TC71 (Type 1, 7/6) cells by TK216-2 at different concentrations (lower absorbance numbers correlating to greater growth inhibition). FIG. 1B provides cell viability (%) for SKES (Type 2, 7/5) cells exposed to TK216-2 at different concentrations. FIG. 1C provides data for growth inhibition of A4573 (Type 3, 10/6) cells by TK216-2 at different concentrations (lower absorbance numbers correlating to greater growth inhibition).

FIG. 2A provides data for growth inhibition of TC71 (Type 1, 7/6) cells by YK-4-279 at different concentrations (lower absorbance numbers correlating to greater growth inhibition). FIG. 1B provides cell viability (%) for SKES (Type 2, 7/5) cells exposed to YK-4-279 at different concentrations. FIG. 2C provides data for growth inhibition of A4573 (Type 3, 10/6) cells by YK-4-279 at different concentrations (lower absorbance numbers correlating to greater growth inhibition).

FIG. 3A provides data for growth inhibition of TC71 (Type 1, 7/6) cells by TK100-OCD3 at different concentrations (lower absorbance numbers correlating to greater growth inhibition). FIG. 3B provides cell viability (%) for SKES (Type 2, 7/5) cells exposed to TK100-OCD3 at different concentrations. FIG. 3C provides data for growth inhibition of A4573 (Type 3, 10/6) cells by TK100-OCD3 at different concentrations (lower absorbance numbers correlating to greater growth inhibition).

FIG. 4A provides data for growth inhibition of TC71 (Type 1, 7/6) cells by TK Analog 6 at different concentrations (lower absorbance numbers correlating to greater growth inhibition). FIG. 4B provides cell viability (%) data for SKES (Type 2, 7/5) cells exposed to TK Analog 6 at different concentrations. FIG. 4C provides data for growth inhibition of A4573 (Type 3, 10/6) cells by TK Analog 6 at different concentrations (lower absorbance numbers correlating to greater growth inhibition).

FIG. 5A provides data for growth inhibition of TC71 (Type 1, 7/6) cells by TK Analog 7 at different concentrations (lower absorbance numbers correlating to greater growth inhibition). FIG. 5B provides cell viability (%) data for SKES (Type 2, 7/5) cells exposed to TK Analog 7 at different concentrations. FIG. 5C provides data for growth inhibition of A4573 (Type 3, 10/6) cells by TK Analog 7 at different concentrations (lower absorbance numbers correlating to greater growth inhibition).

FIG. 6A provides data for growth inhibition of TC71 (Type 1, 7/6) cells by TK Analog 8 at different concentrations (lower absorbance numbers correlating to greater growth inhibition). FIG. 6B provides cell viability (%) data for SKES (Type 2, 7/5) cells exposed to TK Analog 8 at different concentrations. FIG. 6C provides data for growth inhibition of A4573 (Type 3, 10/6) cells by TK Analog 8 at different concentrations (lower absorbance numbers correlating to greater growth inhibition).

FIG. 7A provides data for growth inhibition of TC71 (Type 1, 7/6) cells by TK216-2 at different concentrations (lower absorbance numbers correlating to greater growth inhibition). FIG. 7B provides cell viability (%) data for SKES (Type 2, 7/5) cells exposed to TK216-2 at different concentrations. FIG. 7C provides data for growth inhibition of A4573 (Type 3, 10/6) cells by TK216-2 at different concentrations (lower absorbance numbers correlating to greater growth inhibition).

FIG. 8A provides data for growth inhibition of TC71 (Type 1, 7/6) cells by TK Analog 9 at different concentrations (lower absorbance numbers correlating to greater growth inhibition). FIG. 8B provides cell viability (%) data for SKES (Type 2, 7/5) cells exposed to TK Analog 9 at different concentrations. FIG. 8C provides data for growth inhibition of A4573 (Type 3, 10/6) cells by TK Analog 9 at different concentrations (lower absorbance numbers correlating to greater growth inhibition).

FIG. 9A provides data for growth inhibition of TC71 (Type 1, 7/6) cells by TK Analog 10 at different concentrations (lower absorbance numbers correlating to greater growth inhibition). FIG. 9B provides cell viability (%) data for SKES (Type 2, 7/5) cells exposed to TK Analog 10 at different concentrations. FIG. 9C provides data for growth inhibition of A4573 (Type 3, 10/6) cells by TK Analog 10 at different concentrations (lower absorbance numbers correlating to greater growth inhibition).

FIG. 10A provides data for growth inhibition of TC71 (Type 1, 7/6) cells by TK Analog 11 at different concentrations (lower absorbance numbers correlating to greater growth inhibition). FIG. 10B provides cell viability (%) data for SKES (Type 2, 7/5) cells exposed to TK Analog 11 at different concentrations. FIG. 10C provides data for growth inhibition of A4573 (Type 3, 10/6) cells by TK Analog 11 at different concentrations (lower absorbance numbers correlating to greater growth inhibition).

FIG. 11A provides data for growth inhibition of TC71 (Type 1, 7/6) cells by TK216-2 at different concentrations (lower absorbance numbers correlating to greater growth inhibition). FIG. 11B provides cell viability (%) data for SKES (Type 2, 7/5) cells exposed to TK216-2 at different concentrations. FIG. 11C provides cell viability (%) data for A4573 (Type 3, 10/6) cells by TK216-2 at different concentrations (lower absorbance numbers correlating to greater growth inhibition).

FIG. 12A provides cell viability (%) data for TC71 (Type 1, 7/6) cells exposed to TK Analog 2 at different concentrations. FIG. 12B provides cell viability (%) data for SKES (Type 2, 7/5) cells exposed to TK Analog 2 at different concentrations. FIG. 12C provides cell viability (%) data for A4573 (Type 3, 10/6) cells exposed to TK Analog 2 at different concentrations.

FIG. 13A provides data for growth inhibition of TC71 (Type 1, 7/6) cells by TK Analog 3 at different concentrations (lower absorbance numbers correlating to greater growth inhibition). FIG. 13B provides cell viability (%) data for SKES (Type 2, 7/5) cells exposed to TK Analog 3 at different concentrations. FIG. 13C provides data for growth inhibition of A4573 (Type 3, 10/6) cells by TK Analog 3 at different concentrations (lower absorbance numbers correlating to greater growth inhibition).

FIG. 14A provides data for growth inhibition of TC71 (Type 1, 7/6) cells by TK Analog 4 at different concentrations (lower absorbance numbers correlating to greater growth inhibition). FIG. 14B provides cell viability (%) data for SKES (Type 2, 7/5) cells exposed to TK Analog 4 at different concentrations. FIG. 14C provides data for growth inhibition of A4573 (Type 3, 10/6) cells by TK Analog 4 at different concentrations (lower absorbance numbers correlating to greater growth inhibition).

FIG. 15A provides data for growth inhibition of TC71 (Type 1, 7/6) cells by TK Analog 5 at different concentrations (lower absorbance numbers correlating to greater growth inhibition). FIG. 15B provides cell viability (%) data for SKES (Type 2, 7/5) cells exposed to TK Analog 5 at different concentrations. FIG.

15C provides data for growth inhibition of A4573 (Type 3, 10/6) cells by TK Analog 5 at different concentrations (lower absorbance numbers correlating to greater growth inhibition).

Figure 1A:
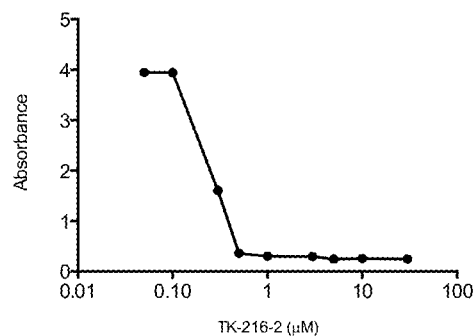
FIGS. 1A-C provide data for TK216-2 on growth inhibition of cells and cell viability.
Figure 1B:
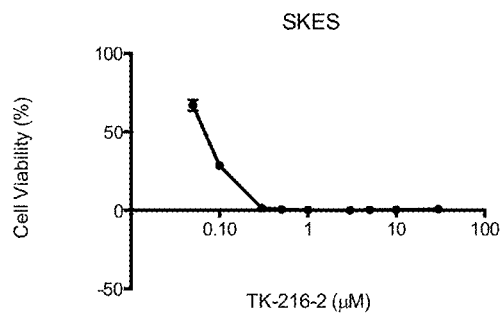
Figure 1C:
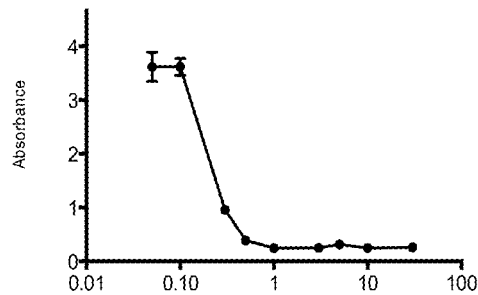
Figure 2A:
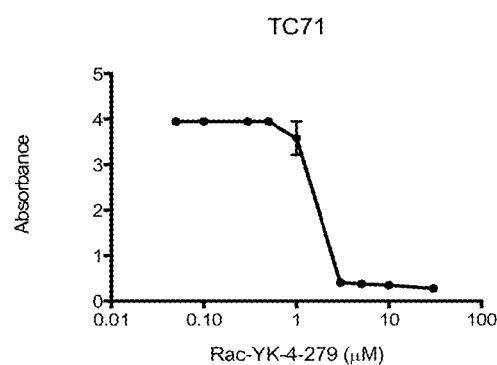
FIGS. 2A-C provide data for YK-4-279 on growth inhibition of cells and cell viability.
Figure 2B:
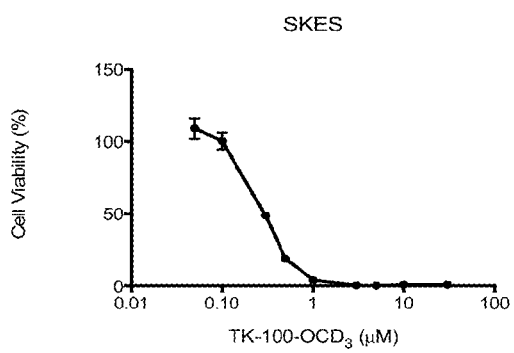
Figure 2C:
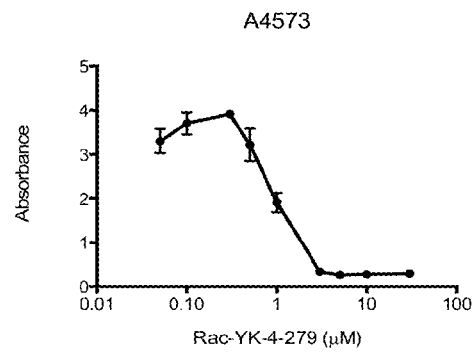
Figure 3A:
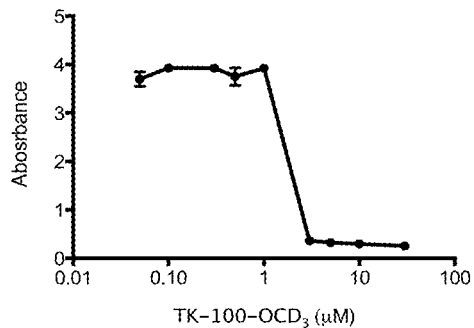
FIGS. 3A-C provide data for TK100-OCD3 on growth inhibition of cells and cell viability.
Figure 3B:
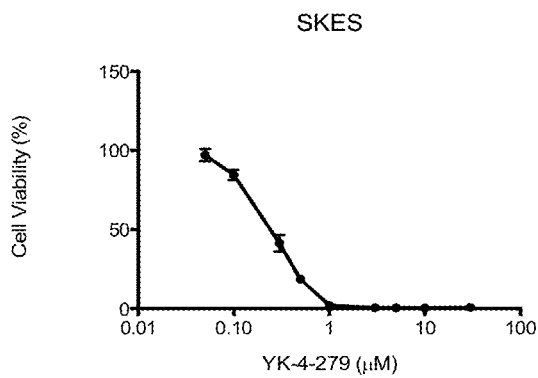
Figure 3C:
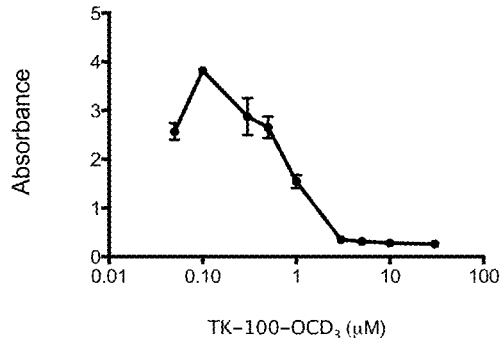
Figure 4A:
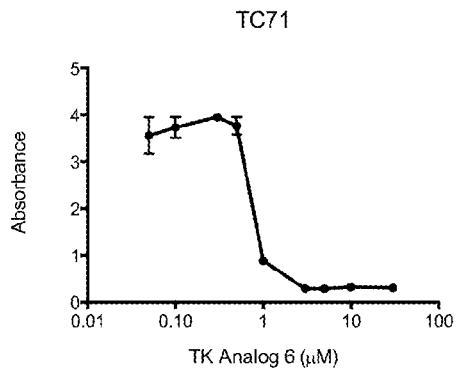
FIGS. 4A-C provide data for TK Analog 6 on growth inhibition of cells and cell viability.
Figure 4B:
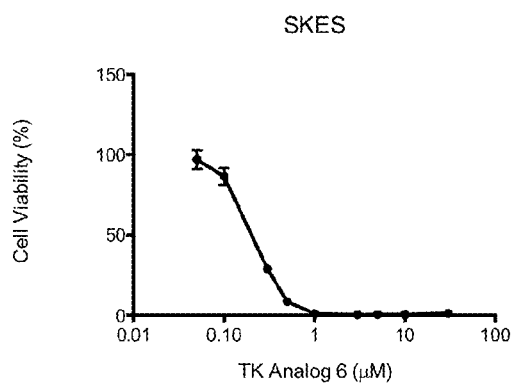
Figure 4C:
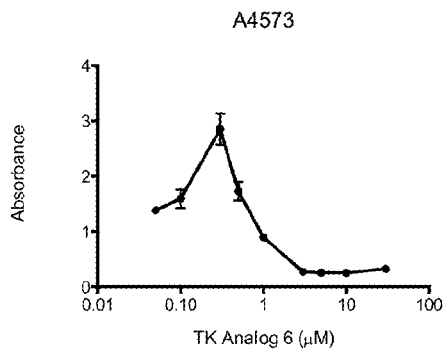
Figure 5A:
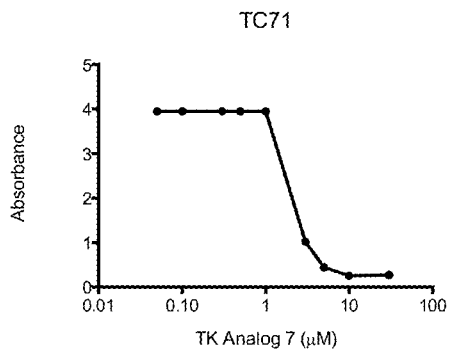
FIGS. 5A-C provide data for TK Analog 7 on growth inhibition of cells and cell viability.
Figure 5B:
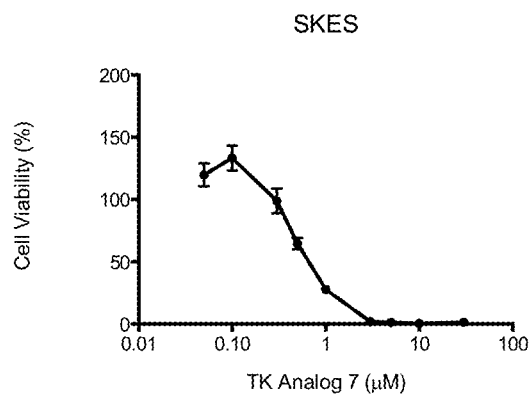
Figure 5C:
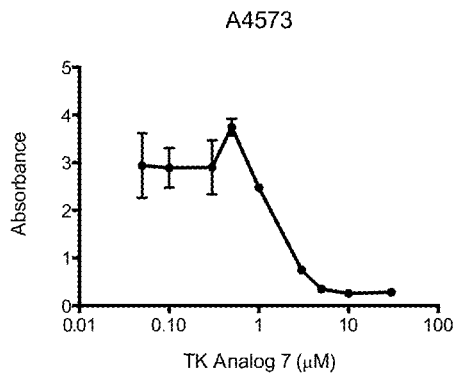
Figure 6A:
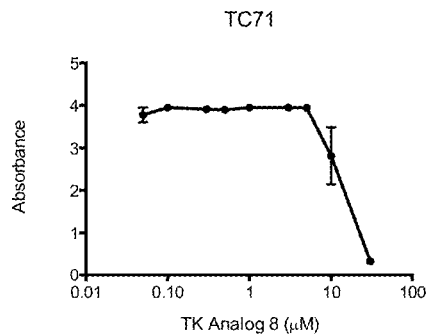
FIGS. 6A-C provide data for TK Analog 8 on growth inhibition of cells and cell viability.
Figure 6B:
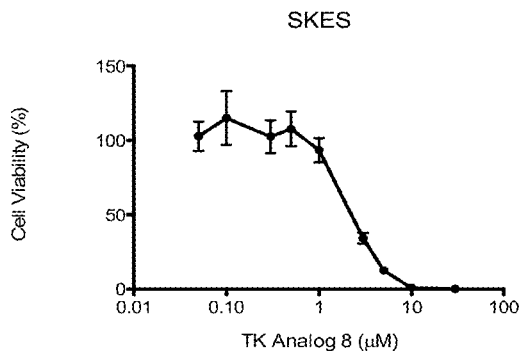
Figure 6C:
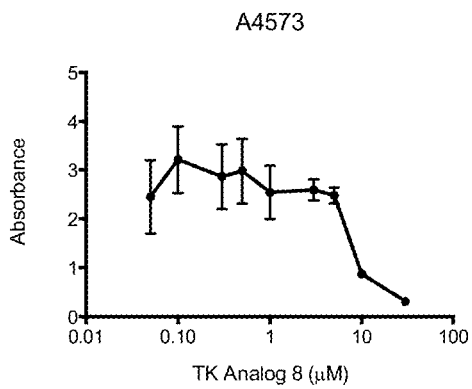
Figure 7A:
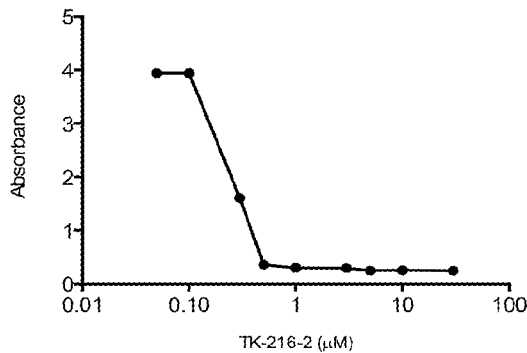
FIGS. 7A-C provide data for TK216-2 on growth inhibition of cells and cell viability.
Figure 7B:
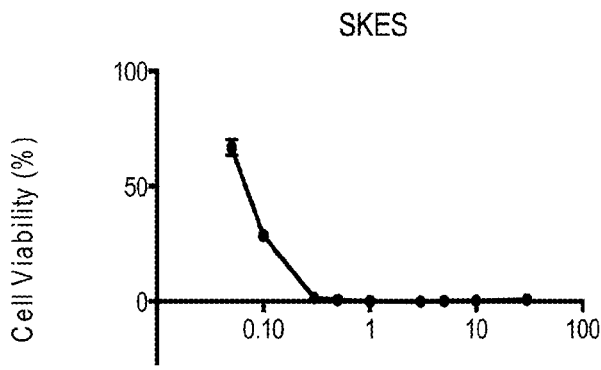
Figure 7C:
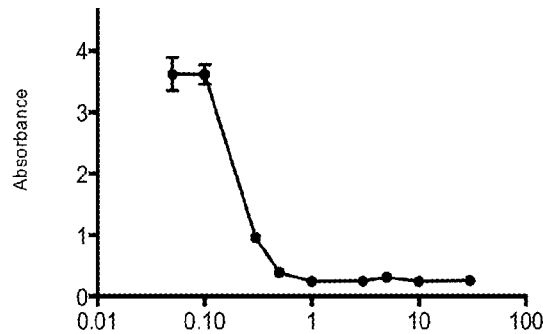
Figure 8A:
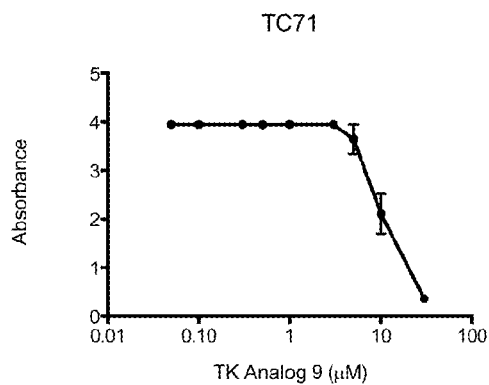
FIGS. 8A-C provide data for TK Analog 9 on growth inhibition of cells and cell viability.
Figure 8B:
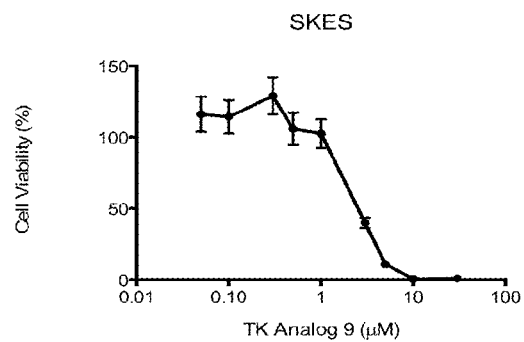
Figure 8C:
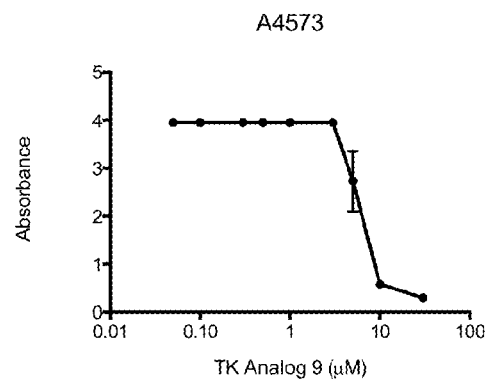
Figure 9A:
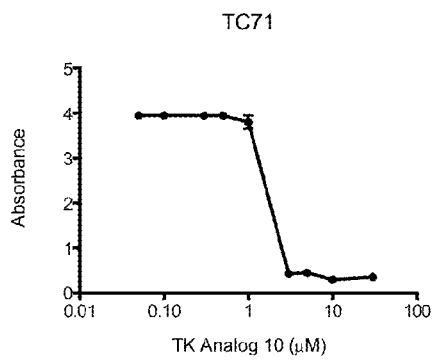
FIGS. 9A-C provide data for TK Analog 10 on growth inhibition of cells and cell viability.
Figure 9B:
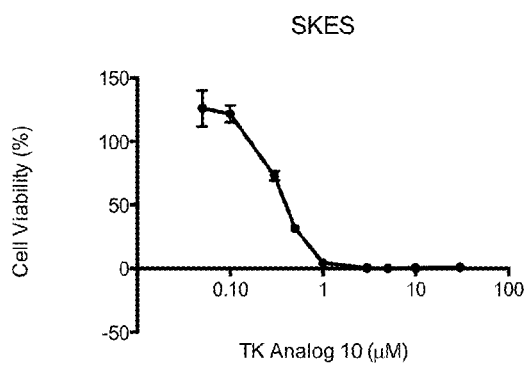
Figure 9C:
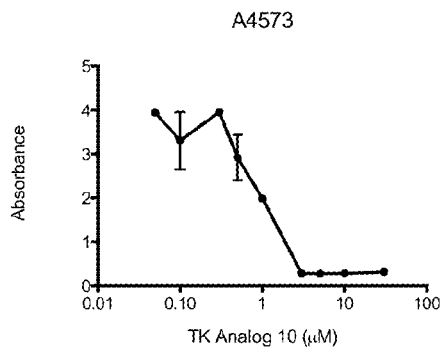
Figure 10A:
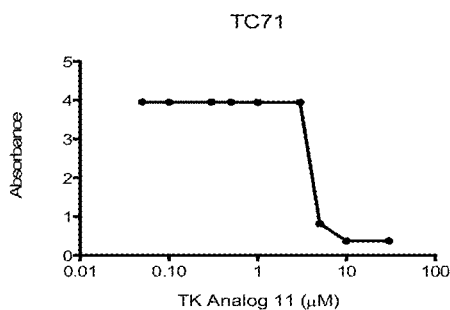
FIGS. 10A-C provide data for TK Analog 11 on growth inhibition of cells and cell viability.
Figure 10B:
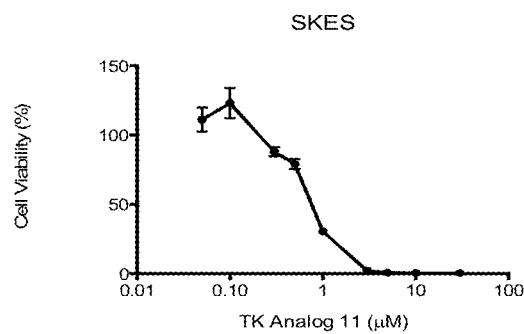
Figure 10C:
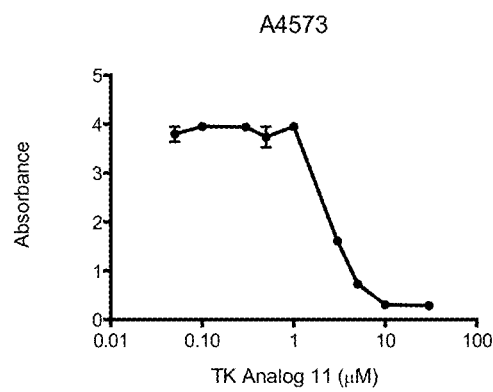
Figure 11A:
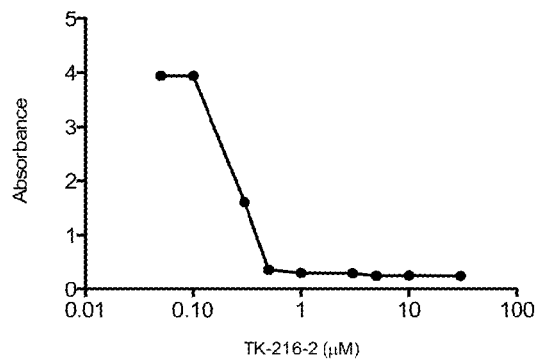
FIGS. 11A-C provide data for TK216-2 on growth inhibition of cells and cell viability.
Figure 11B:
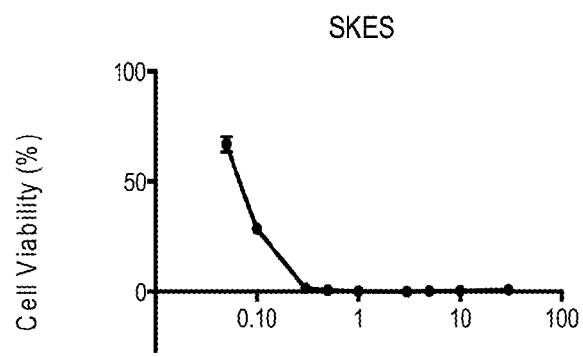
Figure 11C:
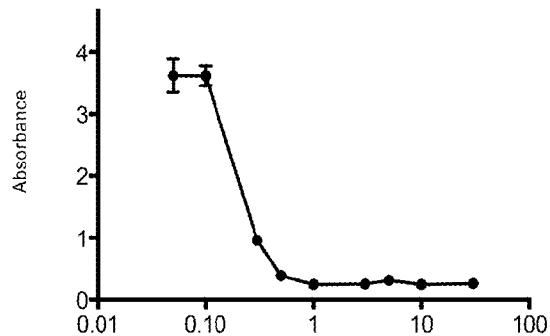
Figure 12A:
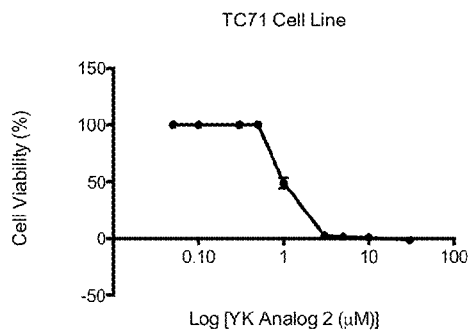
FIGS. 12A-C provide data for TK Analog 2 on cell viability.
Figure 12B:
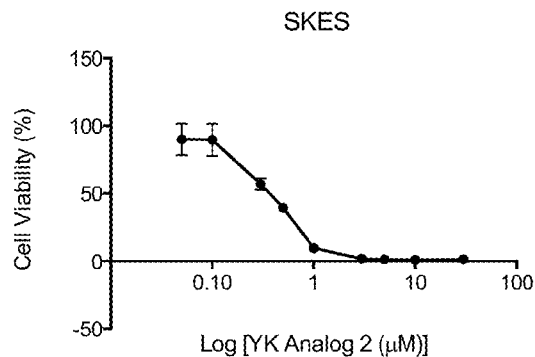
Figure 12C:
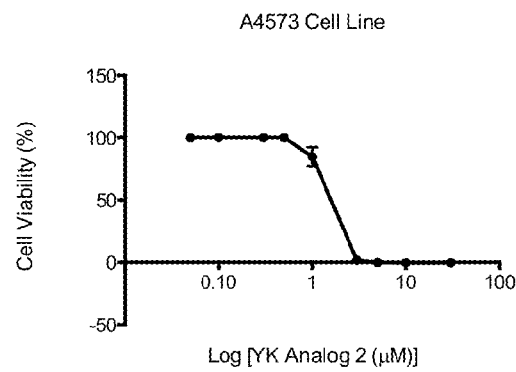
Figure 13A:
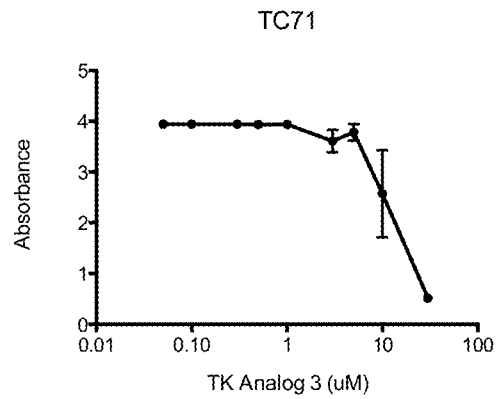
FIGS. 13A-C provide data for TK Analog 3 on growth inhibition of cells and cell viability.
Figure 13B:
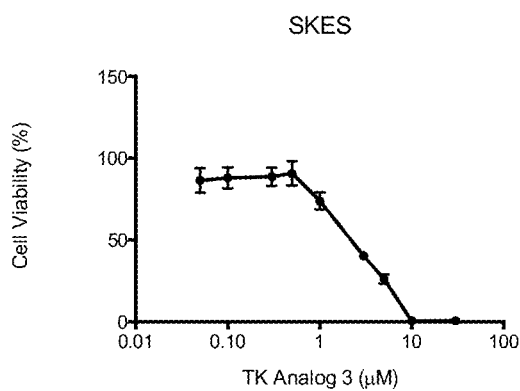
Figure 13C:
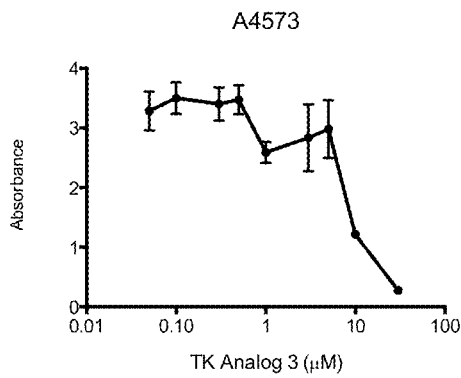
Figure 14A:
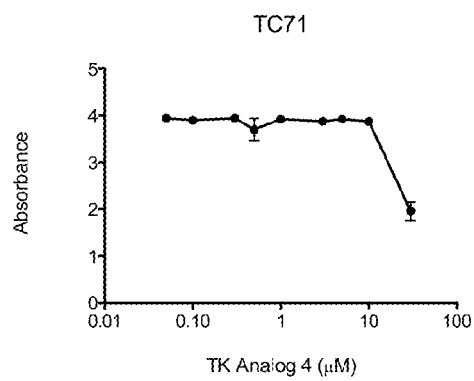
FIGS. 14A-C provide data for TK Analog 4 on growth inhibition of cells and cell viability.
Figure 14B:
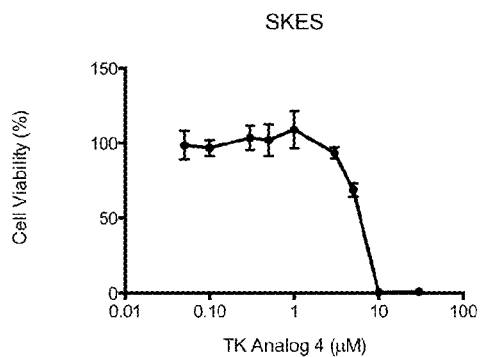
Figure 14C:
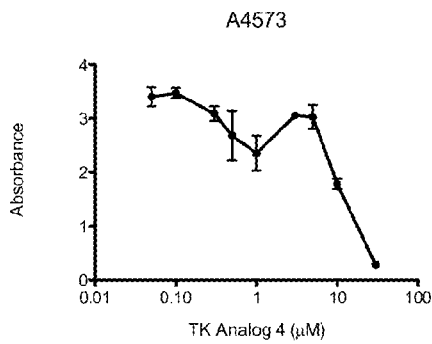
Figure 15A:
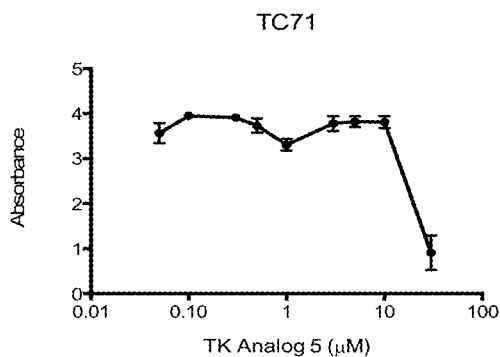
FIGS. 15A-C provide data for TK Analog 5 on growth inhibition of cells and cell viability.
Figure 15B:
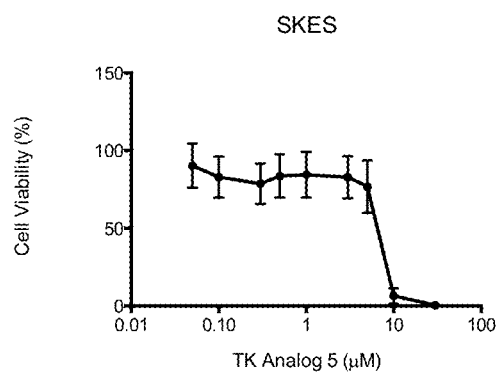
Figure 15C:
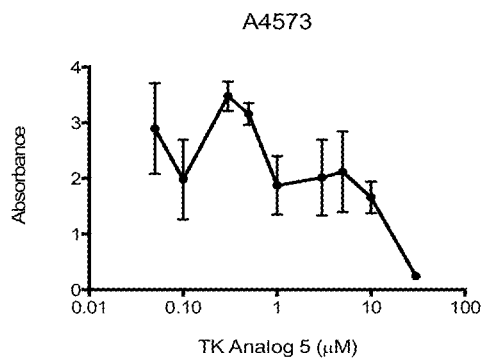
Figure 16A:
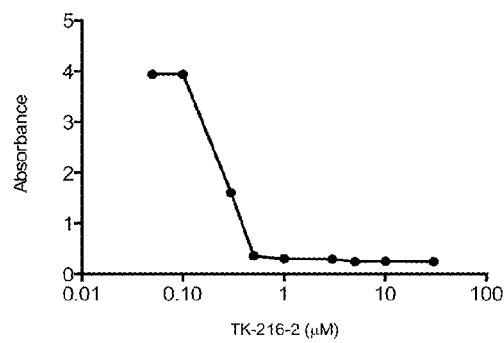
Figure 16B:
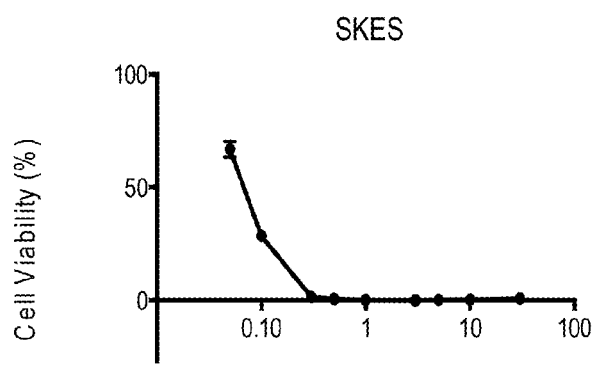
Figure 16C:
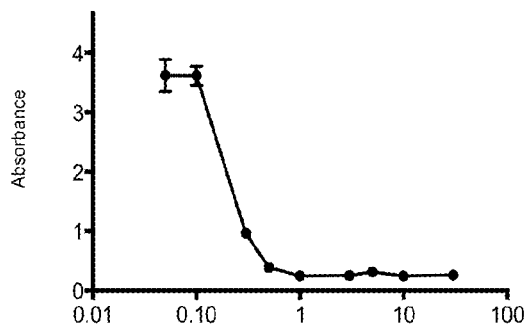

FIGS. 16A-C provide data for TK216-2 on growth inhibition of cells and cell viability. FIG. 16A provides data for growth inhibition of TC71 (Type 1, 7/6) cells by TK216-2 at different concentrations (lower absorbance numbers correlating to greater growth inhibition). FIG. 16B provides cell viability (%) data for SKES (Type 2, 7/5) cells exposed to TK216-2 at different concentrations. FIG. 16C provides data for growth inhibition of A4573 (Type 3, 10/6) cells by TK216-2 at different concentrations (lower absorbance numbers correlating to greater growth inhibition).

Figure 17A:
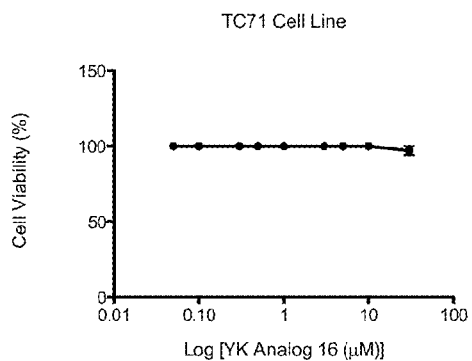
Figure 17B:
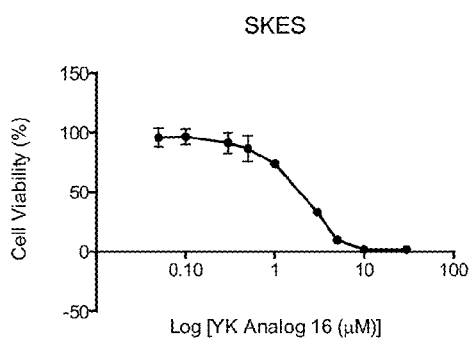
Figure 17C:
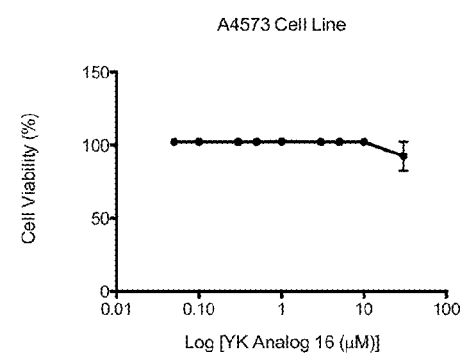

FIGS. 17A-C provide data for TK Analog 16 on cell viability. FIG. 17A provides cell viability (%) data for TC71 (Type 1, 7/6) cells exposed to TK Analog 16 at different concentrations. FIG. 17B provides cell viability (%) data for SKES (Type 2, 7/5) cells exposed to TK Analog 16 at different concentrations. FIG. 17C provides cell viability (%) data for A4573 (Type 3, 10/6) cells exposed to TK Analog 16 at different concentrations.

Figure 18A:
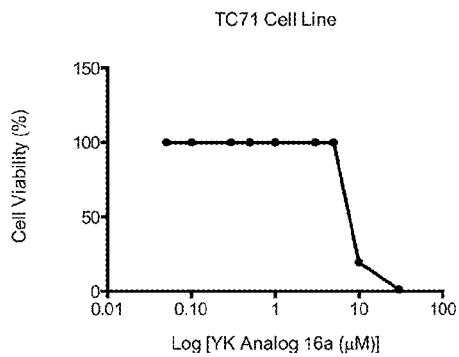
Figure 18B:
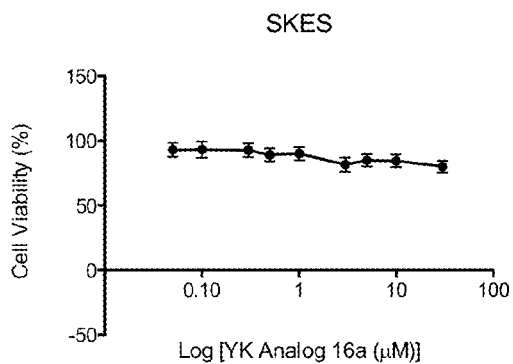
Figure 18C:
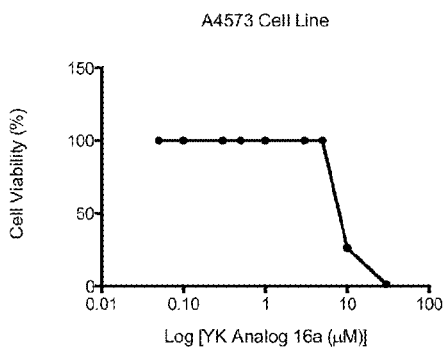

FIGS. 18A-C provide data for TK Analog 16A on cell viability. FIG. 18A provides cell viability (%) data for TC71 (Type 1, 7/6) cells exposed to TK Analog 16A at different concentrations. FIG. 18B provides cell viability (%) data for SKES (Type 2, 7/5) cells exposed to TK Analog 16A at different concentrations. FIG. 18C provides cell viability (%) data for A4573 (Type 3, 10/6) cells exposed to TK Analog 16A at different concentrations.

Figure 19A:
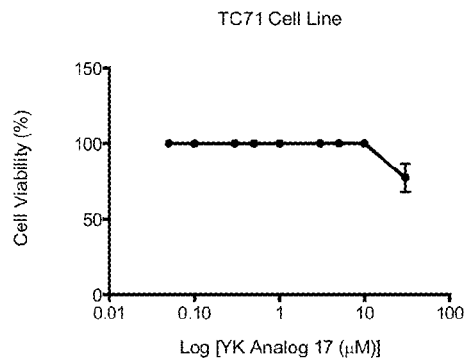
Figure 19B:
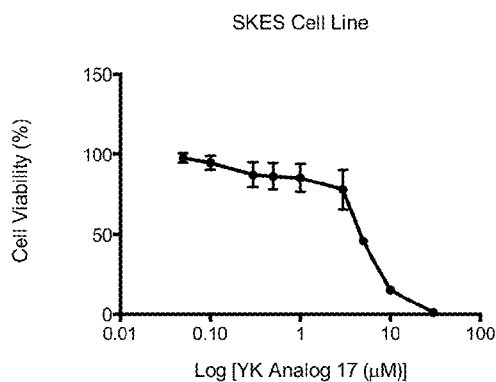
Figure 19C:
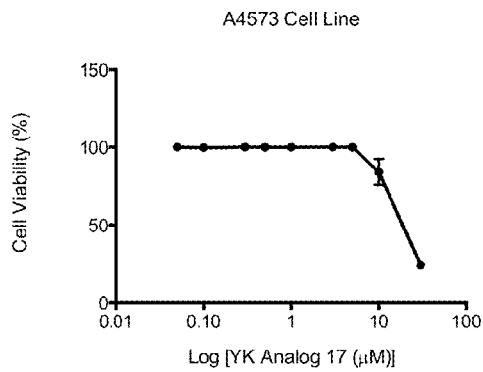

FIGS. 19A-C provide data for TK Analog 17 on cell viability. FIG. 19A provides cell viability (%) data for TC71 (Type 1, 7/6) cells exposed to TK Analog 17 at different concentrations. FIG. 19B provides cell viability (%) data for SKES (Type 2, 7/5) cells exposed to TK Analog 17 at different concentrations. FIG. 19C provides cell viability (%) data for A4573 (Type 3, 10/6) cells exposed to TK Analog 17 at different concentrations.

Figure 20A:
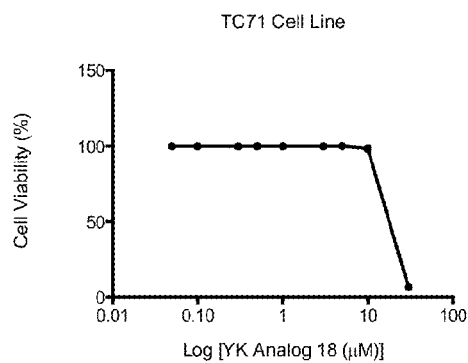
Figure 20B:
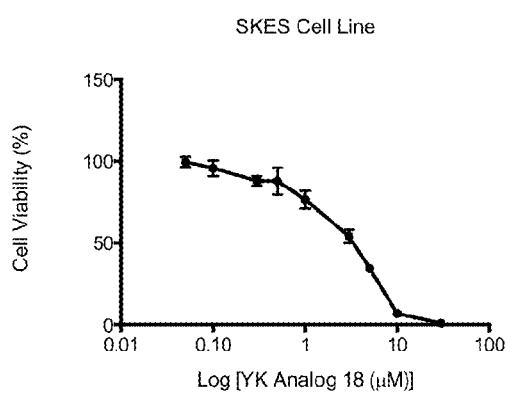
Figure 20C:
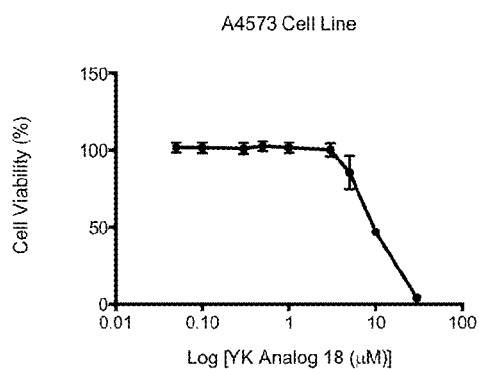

FIGS. 20A-C provide data for TK Analog 18 on cell viability. FIG. 20A provides cell viability (%) data for TC71 (Type 1, 7/6) cells exposed to TK Analog 18 at different concentrations. FIG. 20B provides cell viability (%) data for SKES (Type 2, 7/5) cells exposed to TK Analog 18 at different concentrations. FIG. 20C provides cell viability (%) data for A4573 (Type 3, 10/6) cells exposed to TK Analog 18 at different concentrations.

Figure 21A:
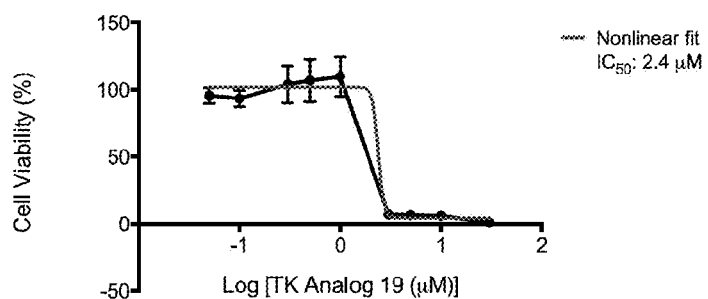
Figure 21B:
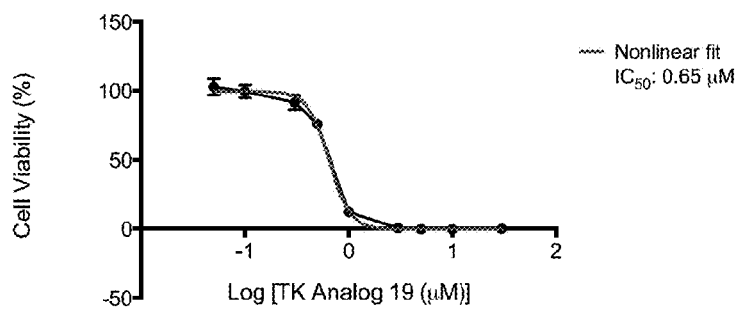
Figure 21C:
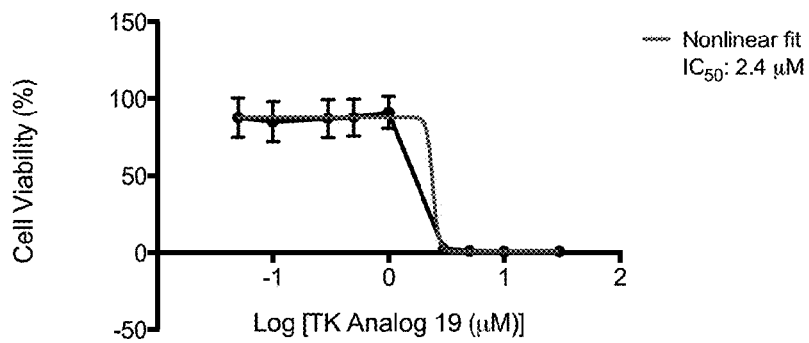

FIGS. 21A-C provide data for TK Analog 19 on cell viability. FIG. 21A provides cell viability (%) data for TC71 (Type 1, 7/6) cells exposed to TK Analog 19 at different concentrations. FIG. 21B provides cell viability (%) data for SKES (Type 2, 7/5) cells exposed to TK Analog 19 at different concentrations. FIG. 21C provides cell viability (%) data for A4573 (Type 3, 10/6) cells exposed to TK Analog 19 at different concentrations.

Figure 22A:
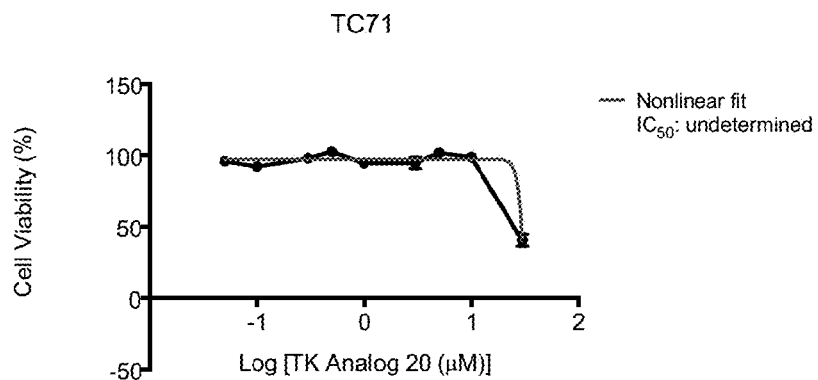
Figure 22B:
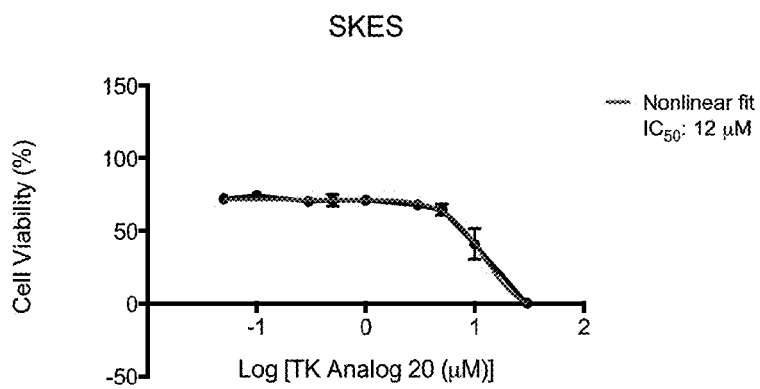
Figure 22C:
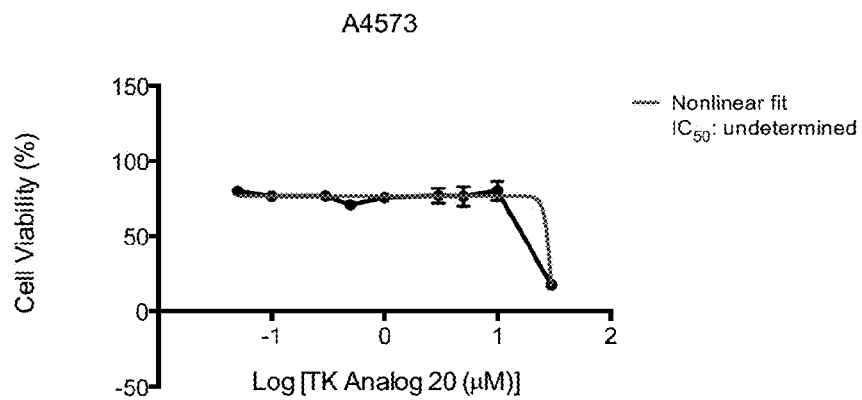

FIGS. 22A-C provide data for TK Analog 20 on cell viability. FIG. 22A provides cell viability (%) data for TC71 (Type 1, 7/6) cells exposed to TK Analog 20 at different concentrations. FIG. 22B provides cell viability (%) data for SKES (Type 2, 7/5) cells exposed to TK Analog 20 at different concentrations. FIG. 22C provides cell viability (%) data for A4573 (Type 3, 10/6) cells exposed to TK Analog 20 at different concentrations.

Figure 23A:
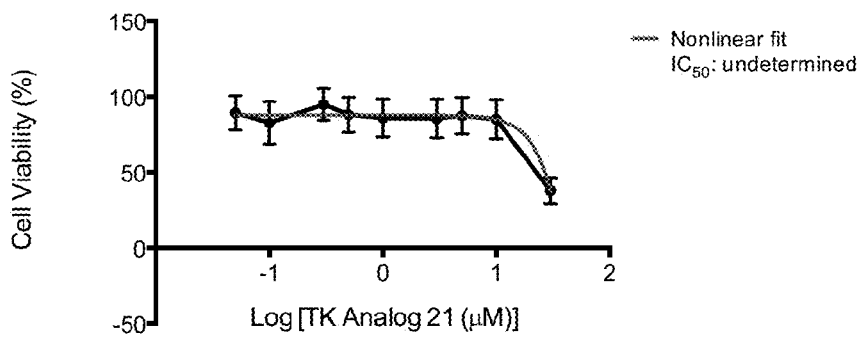
Figure 23B:
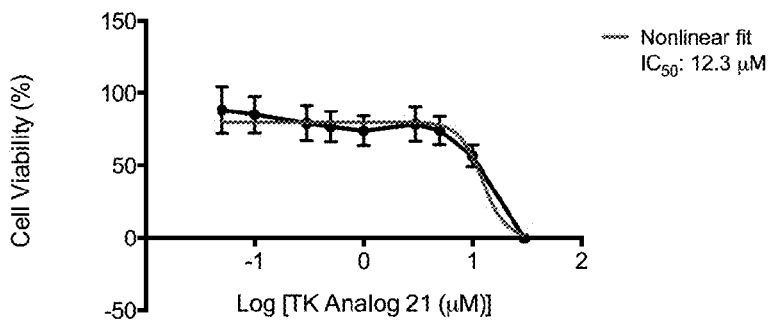
Figure 23C:
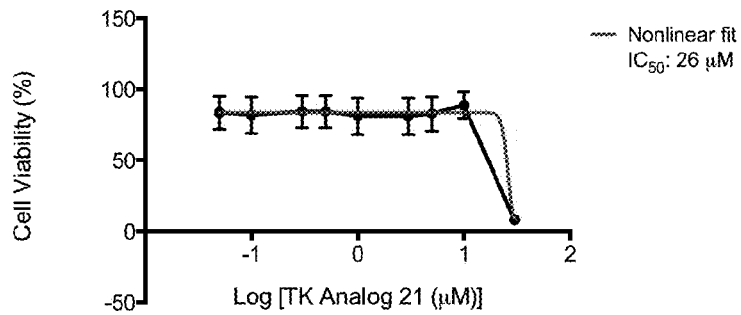

FIGS. 23A-C provide data for TK Analog 21 on cell viability. FIG. 23A provides cell viability (%) data for TC71 (Type 1, 7/6) cells exposed to TK Analog 21 at different concentrations. FIG. 23B provides cell viability (%) data for SKES (Type 2, 7/5) cells exposed to TK Analog 21 at different concentrations. FIG. 23C provides cell viability (%) data for A4573 (Type 3, 10/6) cells exposed to TK Analog 21 at different concentrations.

Figure 24A:
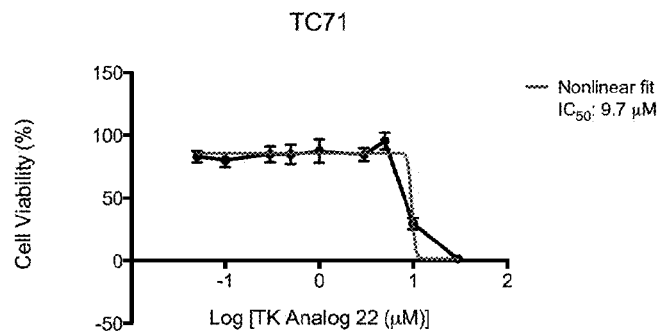
Figure 24B:
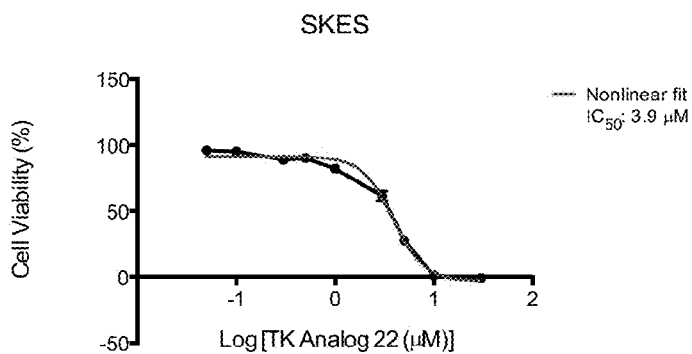
Figure 24C:
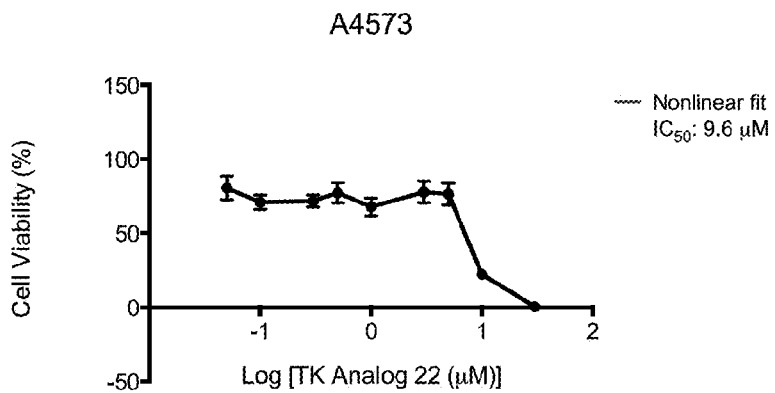

FIGS. 24A-C provide data for TK Analog 22 on cell viability. FIG. 24A provides cell viability (%) data for TC71 (Type 1, 7/6) cells exposed to TK Analog 22 at different concentrations. FIG. 24B provides cell viability (%) data for SKES (Type 2, 7/5) cells exposed to TK Analog 22 at different concentrations. FIG. 24C provides cell viability (%) data for A4573 (Type 3, 10/6) cells exposed to TK Analog 22 at different concentrations.

Figure 25A:
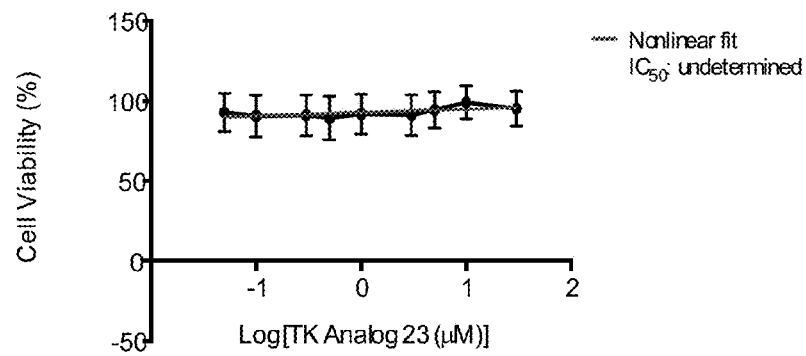
Figure 25B:
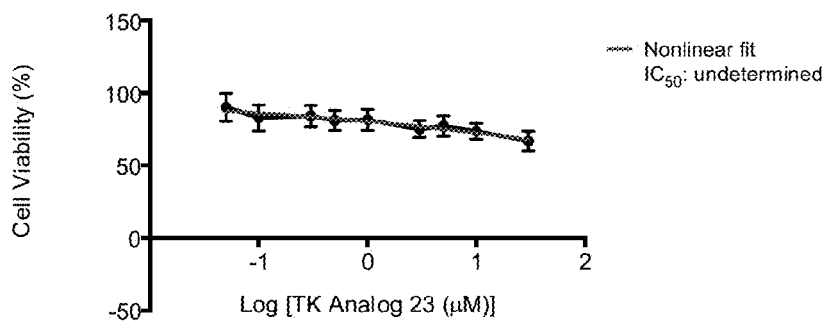
Figure 25C:
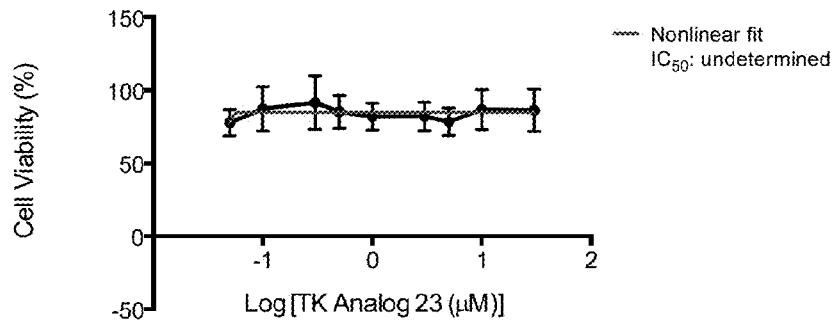

FIGS. 25A-C provide data for TK Analog 23 on cell viability. FIG. 25A provides cell viability (%) data for TC71 (Type 1, 7/6) cells exposed to TK Analog 23 at different concentrations. FIG. 25B provides cell viability (%) data for SKES (Type 2, 7/5) cells exposed to TK Analog 23 at different concentrations. FIG. 25C provides cell viability (%) data for A4573 (Type 3, 10/6) cells exposed to TK Analog 23 at different concentrations.

Figure 26A:
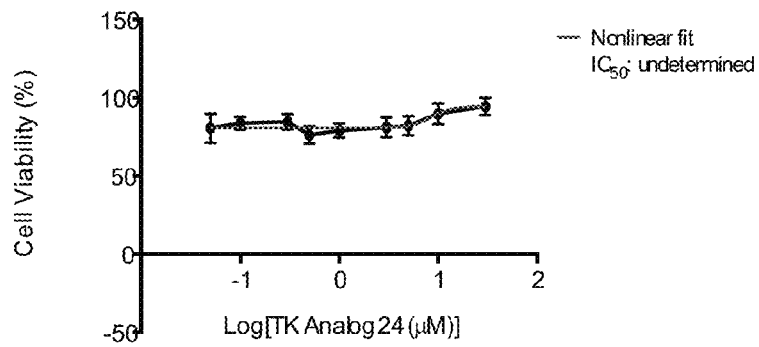
Figure 26B:
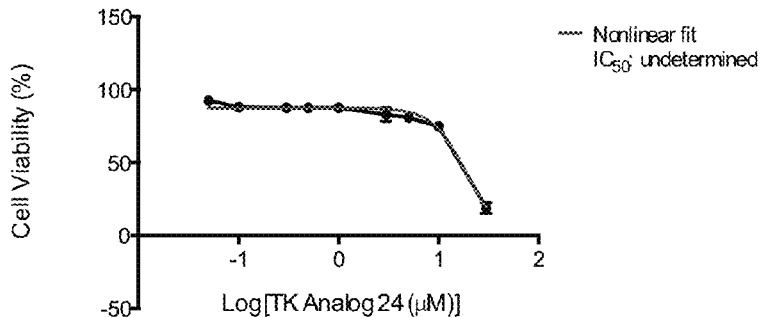
Figure 26C:
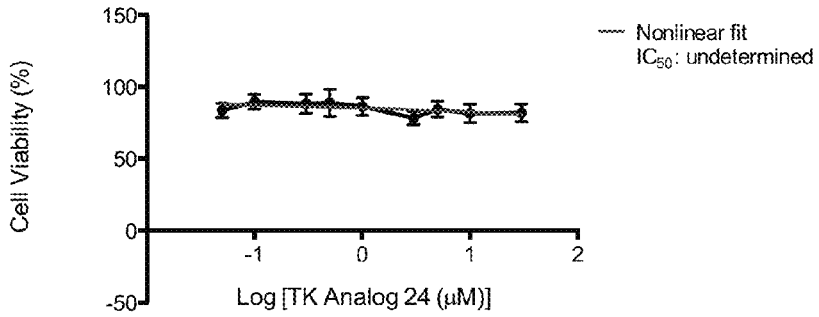

FIGS. 26A-C provide data for TK Analog 24 on cell viability. FIG. 26A provides cell viability (%) data for TC71 (Type 1, 7/6) cells exposed to TK Analog 24 at different concentrations. FIG. 26B provides cell viability (%) data for SKES (Type 2, 7/5) cells exposed to TK Analog 24 at different concentrations. FIG. 26C provides cell viability (%) data for A4573 (Type 3, 10/6) cells exposed to TK Analog 24 at different concentrations.

Figure 27A:
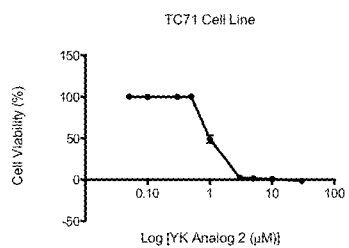
Figure 27B:
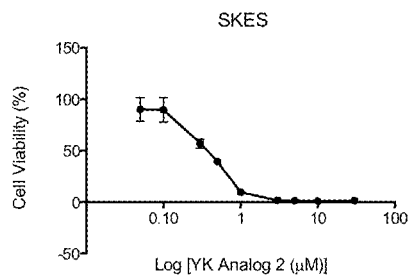
Figure 27C:
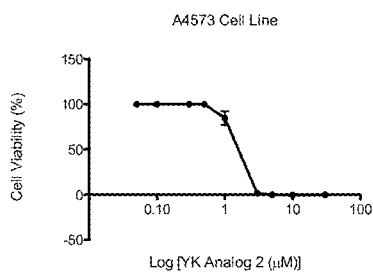

FIGS. 27A-C provide data for racemic TK Analog 2 on cell viability. FIG. 27A provides cell viability (%) data for TC71 (Type 1, 7/6) cells exposed to TK Analog 2 at different concentrations. FIG. 27B provides cell viability (%) data for SKES (Type 2, 7/5) cells exposed to TK Analog 2 at different concentrations. FIG. 27C provides cell viability (%) data for A4573 (Type 3, 10/6) cells exposed to TK Analog 2 at different concentrations.

Figure 28A:
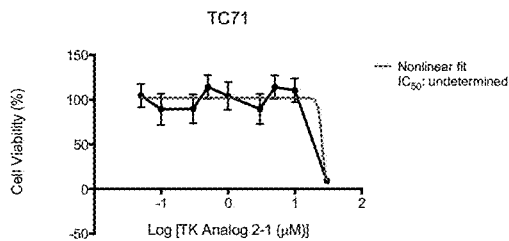
Figure 28B:
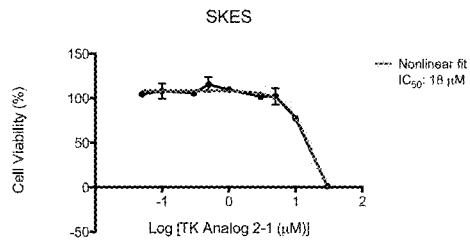
Figure 28C:
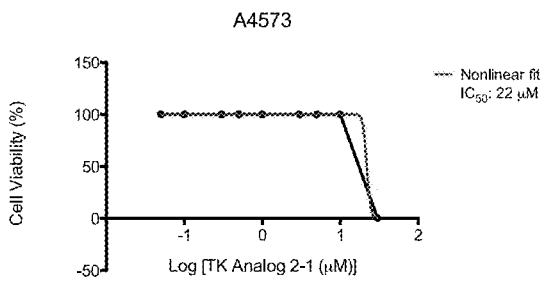

FIGS. 28A-C provide data for TK Analog 2-1 (Enantiomer 1) on cell viability. FIG. 28A provides cell viability (%) data for TC71 (Type 1, 7/6) cells exposed to TK Analog 2-1 (Enantiomer 1) at different concentrations. FIG. 28B provides cell viability (%) data for SKES (Type 2, 7/5) cells exposed to TK Analog 2-1 (Enantiomer 1) at different concentrations. FIG. 28C provides cell viability (%) data for A4573 (Type 3, 10/6) cells exposed to TK Analog 2-1 (Enantiomer 1) at different concentrations.

Figure 29A:
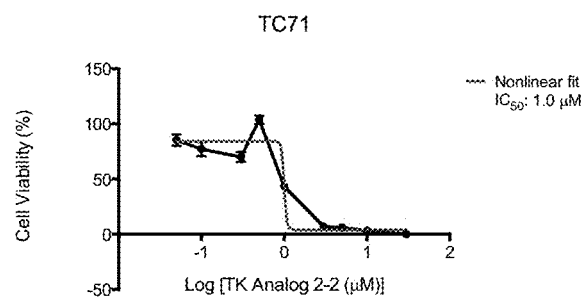
Figure 29B:
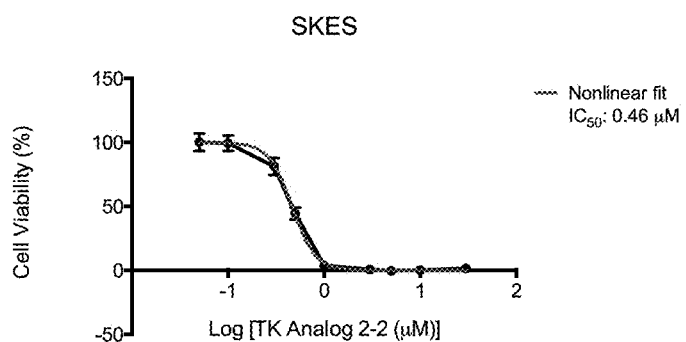
Figure 29C:
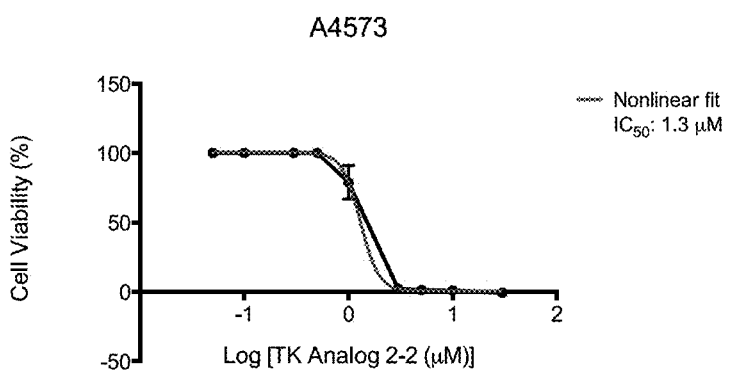

FIGS. 29A-C provide data for enantiomers for TK Analog 2-2, (Enantiomer 2) on cell viability. FIG. 29A provides cell viability (%) data for TC71 (Type 1, 7/6) cells exposed to TK Analog 2-2, (Enantiomer 2) at different concentrations. FIG. 29B provides cell viability (%) data for SKES (Type 2, 7/5) cells exposed to TK Analog 2-2, (Enantiomer 2) at different concentrations. FIG. 29C provides cell viability (%) data for A4573 (Type 3, 10/6) cells exposed to TK Analog 2-2, (Enantiomer 2) at different concentrations.

Figure 30A:
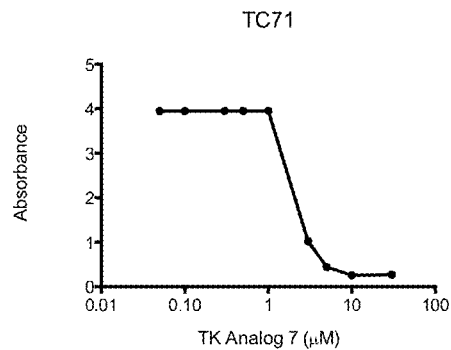
Figure 30B:
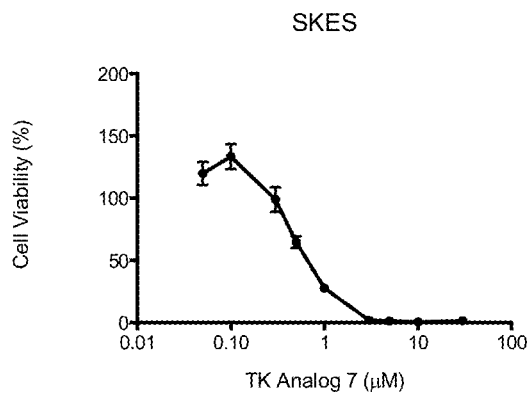
Figure 30C:
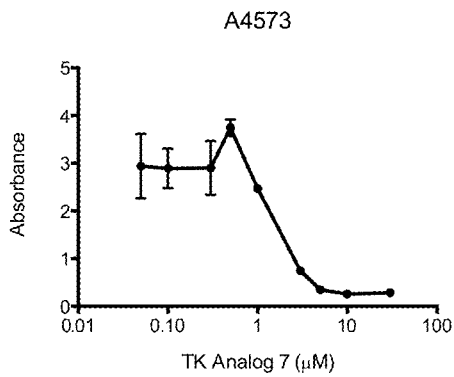

FIGS. 30A-C provide data for racemic TK Analog 7 on growth inhibition of cells and cell viability. FIG. 30A provides data for growth inhibition of TC71 (Type 1, 7/6) cells by TK Analog 7 at different concentrations (lower absorbance numbers correlating to greater growth inhibition). FIG. 30B provides cell viability (%) data for SKES (Type 2, 7/5) cells exposed to TK Analog 7 at different concentrations. FIG. 30C provides data for growth inhibition of A4573 (Type 3, 10/6) cells by TK Analog 7 at different concentrations (lower absorbance numbers correlating to greater growth inhibition).

Figure 31A:
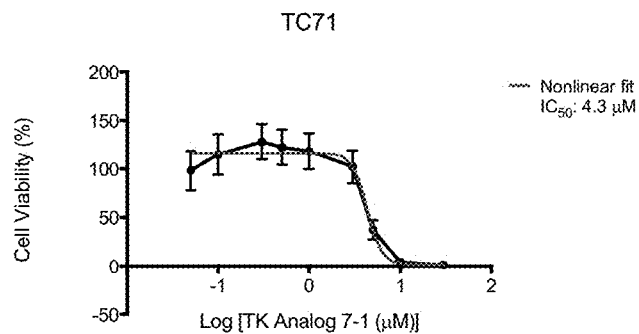
Figure 31B:
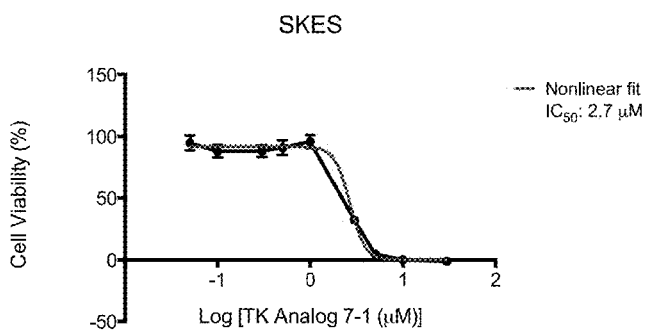
Figure 31C:
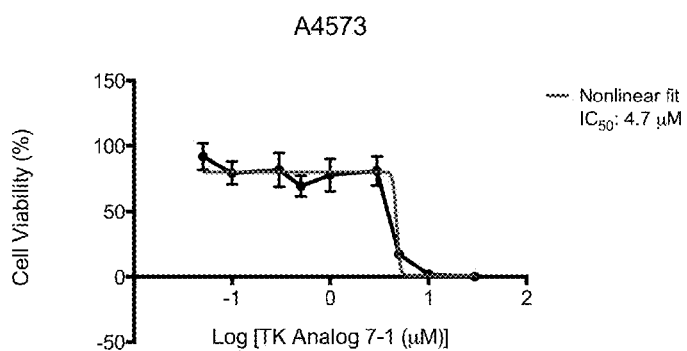

FIGS. 31A-C provide data for TK Analog 7 (Enantiomer 1) on cell viability. FIG. 31A provides cell viability (%) data for TC71 (Type 1, 7/6) cells exposed to TK Analog 7

(Enantiomer 1) at different concentrations. FIG. 31B provides cell viability (%) data for SKES (Type 2, 7/5) cells exposed to TK Analog 7 (Enantiomer 1) at different concentrations. FIG. 31C provides cell viability (%) data for A4573 (Type 3, 10/6) cells exposed to TK Analog 7 (Enantiomer 1) at different concentrations.

Figure 32A:
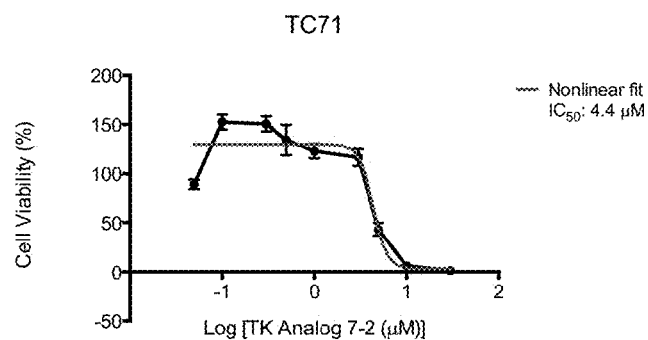
Figure 32B:
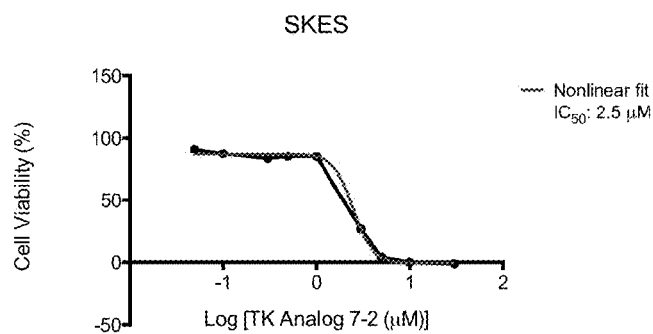
Figure 32C:
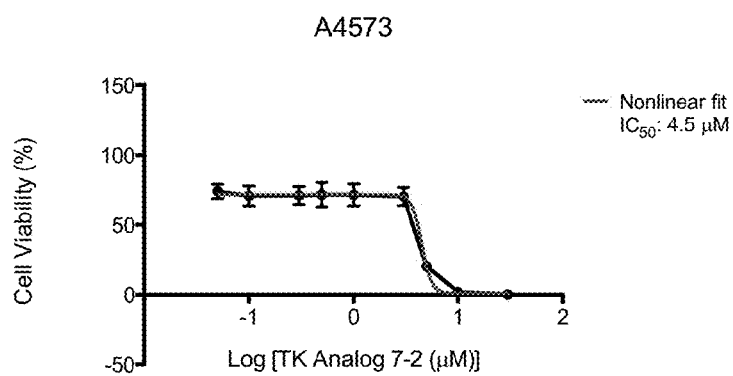

FIGS. 32A-C provide data for TK Analog 7 (Enantiomer 2) on cell viability. FIG. 32A provides cell viability (%) data for TC71 (Type 1, 7/6) cells exposed to TK Analog 7 (Enantiomer 2) at different concentrations. FIG. 32B provides cell viability (%) data for SKES (Type 2, 7/5) cells exposed to TK Analog 7 (Enantiomer 2) at different concentrations. FIG. 32C provides cell viability (%) data for A4573 (Type 3, 10/6) cells exposed to TK Analog 7 (Enantiomer 2) at different concentrations.

Figure 33A:
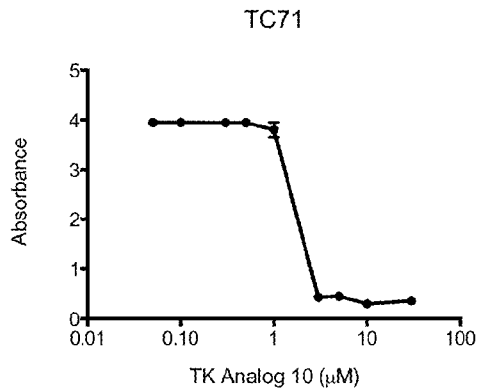
Figure 33B:
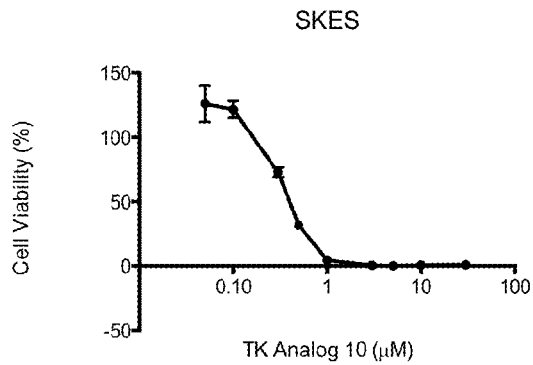
Figure 33C:
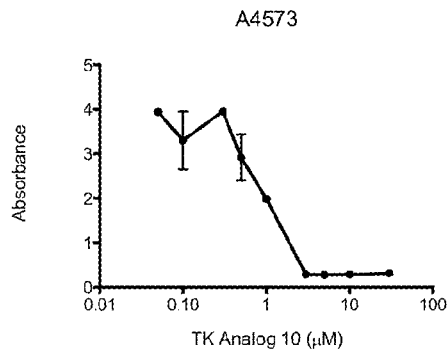

FIGS. 33A-C provide data for racemic TK Analog 10 on growth inhibition of cells and cell viability. FIG. 33A provides data for growth inhibition of TC71 (Type 1, 7/6) cells by TK Analog 10 at different concentrations (lower absorbance numbers correlating to greater growth inhibition). FIG. 33B provides cell viability (%) data for SKES (Type 2, 7/5) cells exposed to TK Analog 10 at different concentrations. FIG. 33C provides data for growth inhibition of A4573 (Type 3, 10/6) cells by TK Analog 10 at different concentrations (lower absorbance numbers correlating to greater growth inhibition).

Figure 34A:
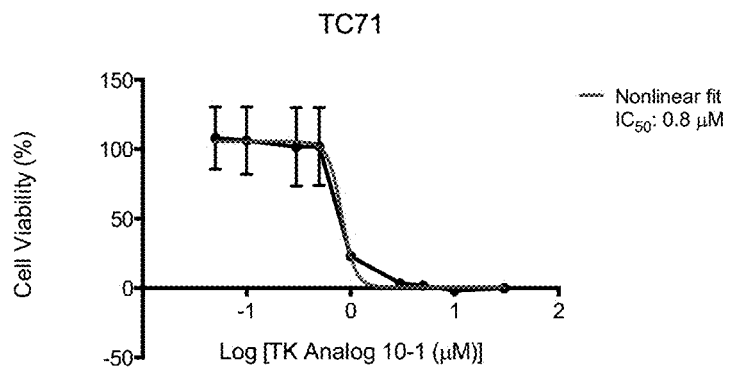
Figure 34B:
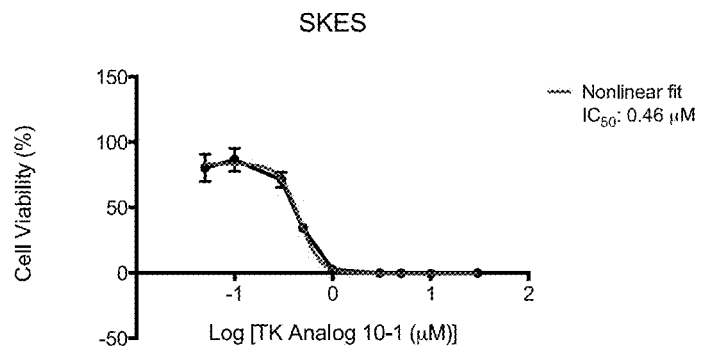
Figure 34C:
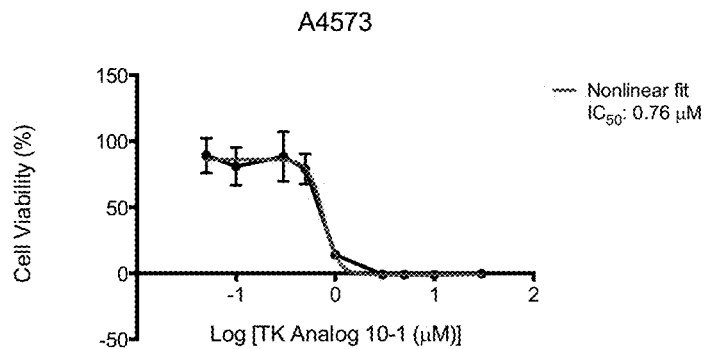

FIGS. 34A-C provide data for TK Analog 10 (Enantiomer 1) on cell viability. FIG. 34A provides cell viability (%) data for TC71 (Type 1, 7/6) cells exposed to TK Analog 10 (Enantiomer 1) at different concentrations. FIG. 34B provides cell viability (%) data for SKES (Type 2, 7/5) cells exposed to TK Analog 10 (Enantiomer 1) at different concentrations. FIG. 34C provides cell viability (%) data for A4573 (Type 3, 10/6) cells exposed to TK Analog 10 (Enantiomer 1) at different concentrations.

Figure 35A:
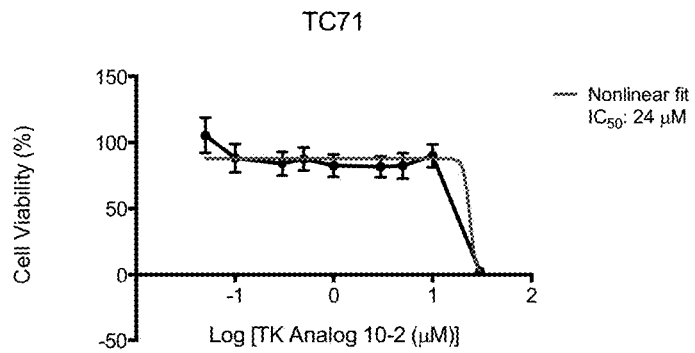
Figure 35B:
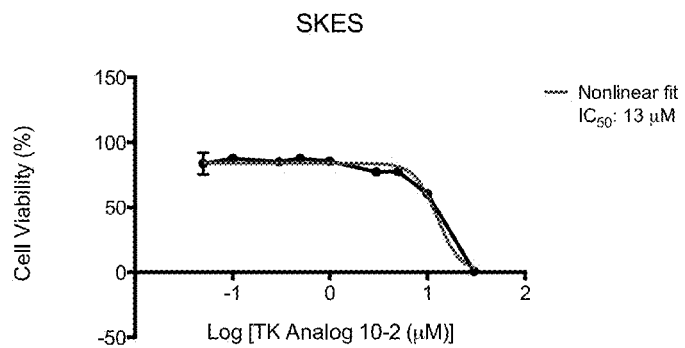
Figure 35C:
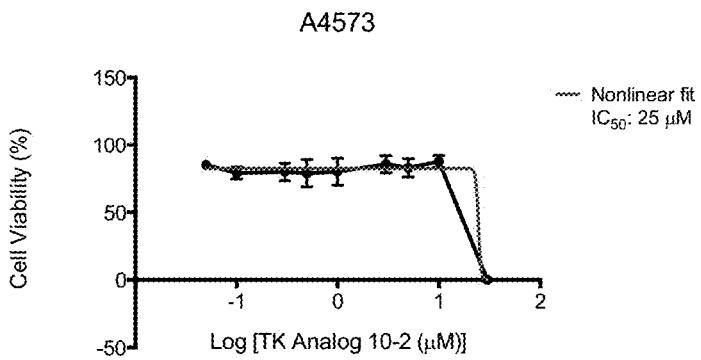

FIGS. 35A-C provide data for enantiomers for TK Analog 10 (Enantiomer 2) on cell viability. FIG. 35A provides cell viability (%) data for TC71 (Type 1, 7/6) cells exposed to TK Analog 10 (Enantiomer 2) at different concentrations. FIG. 35B provides cell viability (%) data for SKES (Type 2, 7/5) cells exposed to TK Analog 10 (Enantiomer 2) at different concentrations. FIG. 35C provides cell viability (%) data for A4573 (Type 3, 10/6) cells exposed to TK Analog 10 at different concentrations.

Figure 36A:
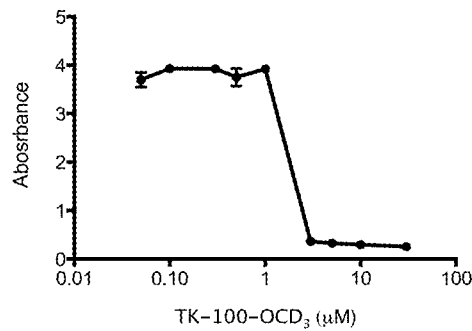
Figure 36B:
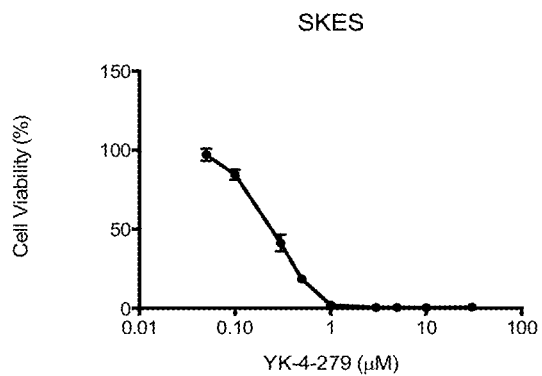
Figure 36C:
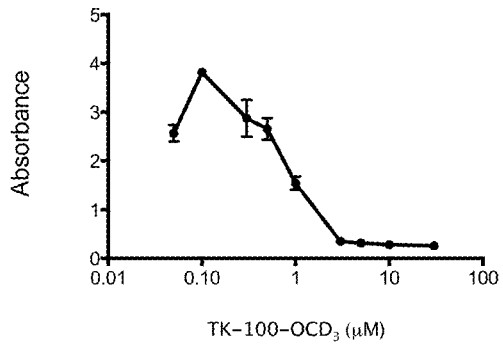

FIGS. 36A-C provide data for racemic TK100-OCD3 on growth inhibition of cells and cell viability. FIG. 36A provides data for growth inhibition of TC71 (Type 1, 7/6) cells by TK100-OCD3 at different concentrations (lower absorbance numbers correlating to greater growth inhibition). FIG. 36B provides cell viability (%) data for SKES (Type 2, 7/5) cells exposed to TK100-OCD3 at different concentrations. FIG. 36C provides data for growth inhibition of A4573 (Type 3, 10/6) cells by TK100-OCD3 at different concentrations (lower absorbance numbers correlating to greater growth inhibition).

Figure 37A:
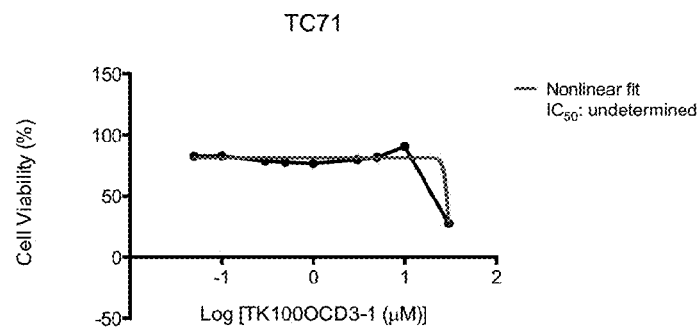
Figure 37B:
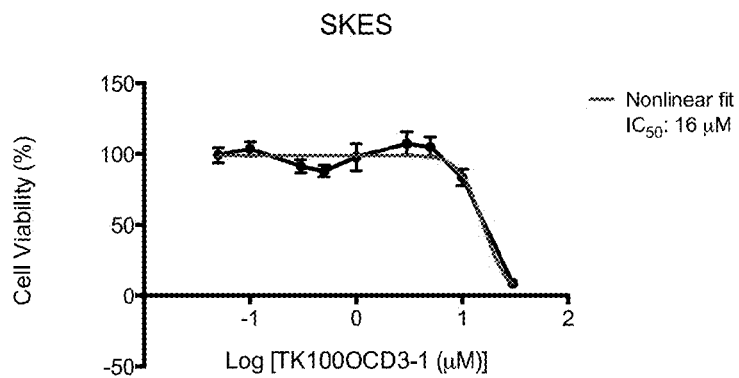
Figure 37C:
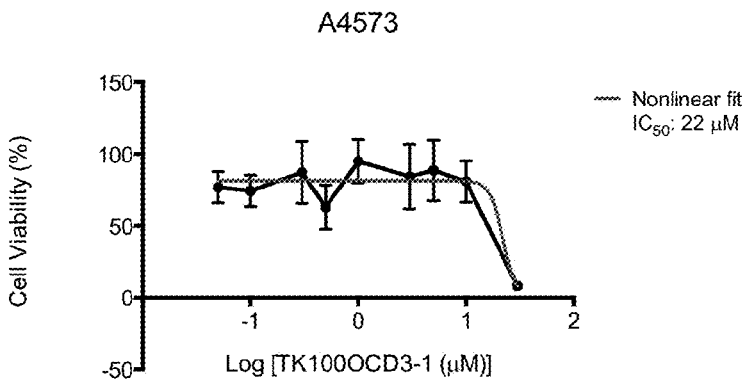

FIGS. 37A-C provide data for TK100-OCD3 (Enantiomer 1) on cell viability. FIG. 37A provides cell viability (%) data for TC71 (Type 1, 7/6) cells exposed to TK100-OCD3 (Enantiomer 1) at different concentrations. FIG. 37B provides cell viability (%) data for SKES (Type 2, 7/5) cells exposed to TK100-OCD3 (Enantiomer 1) at different concentrations. FIG. 37C provides cell viability (%) data for A4573 (Type 3, 10/6) cells exposed to TK100-OCD3 (Enantiomer 1) at different concentrations.

Figure 38A:
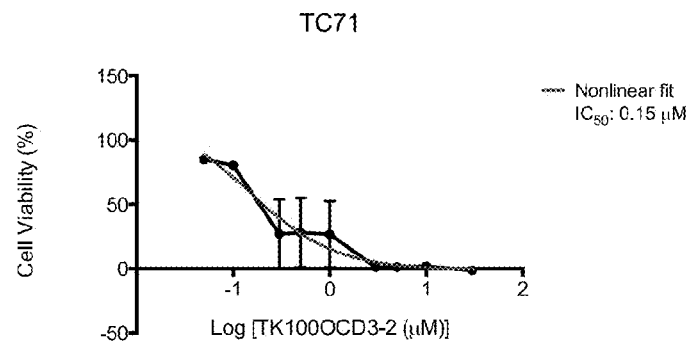
Figure 38B:
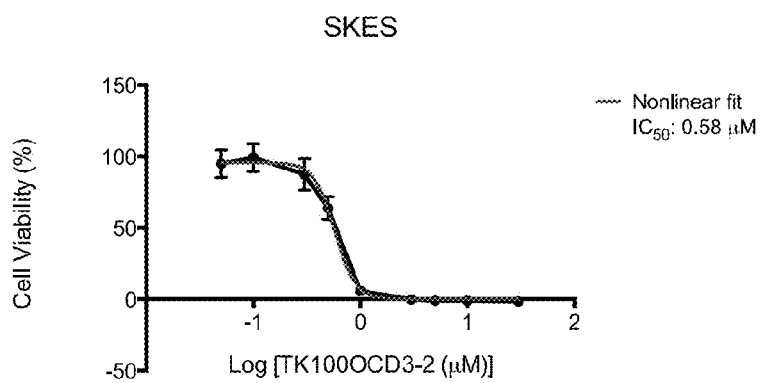
Figure 38C:
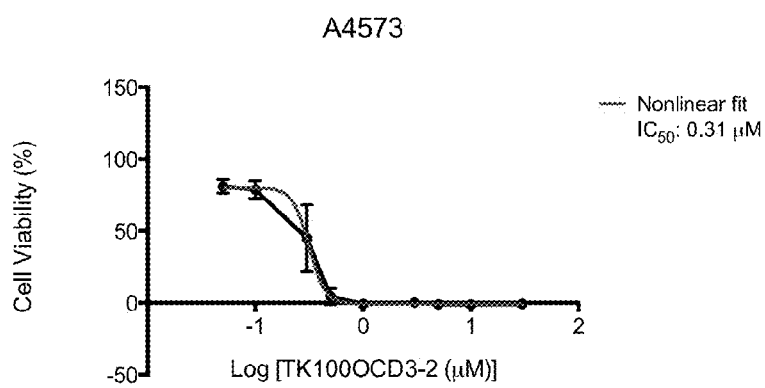

FIGS. 38A-C provide data for enantiomers for TK100-OCD3 (Enantiomer 2) on cell viability. FIG. 38A provides cell viability (%) data for TC71 (Type 1, 7/6) cells exposed to TK100-OCD3 (Enantiomer 2) at different concentrations. FIG. 38B provides cell viability (%) data for SKES (Type 2, 7/5) cells exposed to TK100-OCD3 (Enantiomer 2) at different concentrations. FIG. 38C provides cell viability (%) data for A4573 (Type 3, 10/6) cells exposed to TK100-OCD3 (Enantiomer 2) at different concentrations.

Figure 39:
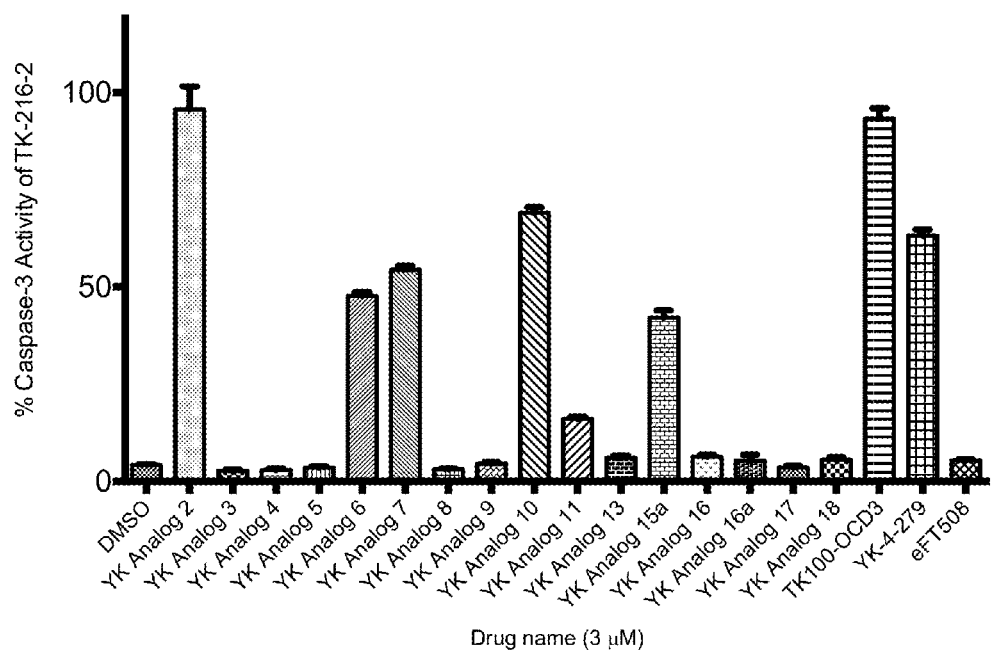

FIG. 39 provides data comparing the activity of various compounds and analogs as a percentage of the activity of TK-216-2 with respect to apoptosis, 18 hour treatment, CASP-3 fluorogenic substrate cleavage.

Figure 40:
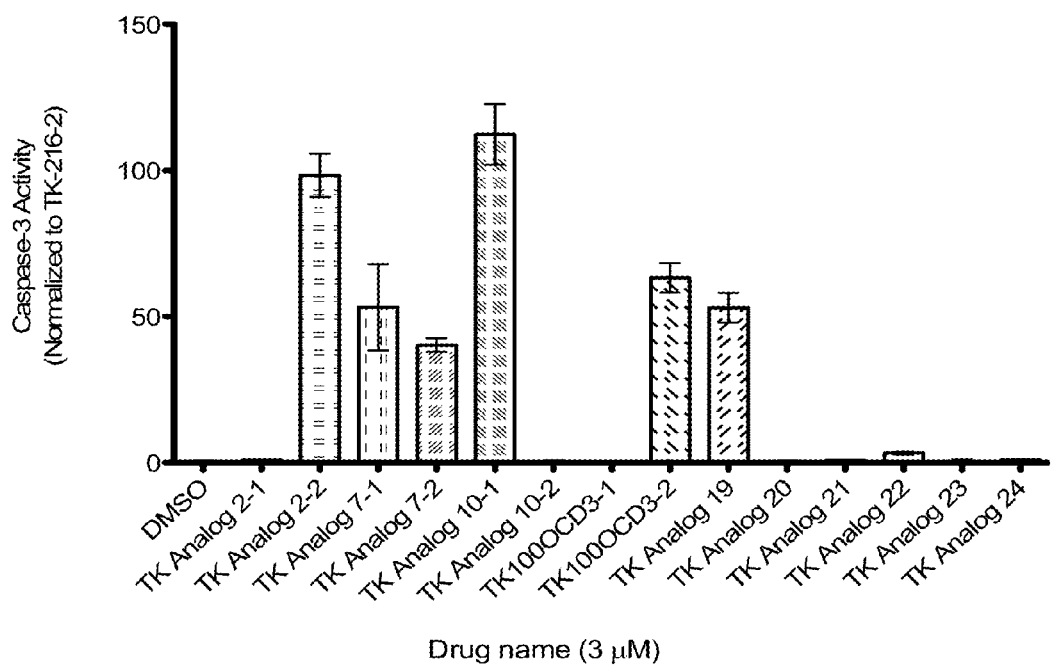

FIG. 40 provides data comparing the activity of various compounds and analogs normalized to the activity of TK-216-2 with respect to apoptosis, 18 hour treatment, CASP-3 fluorogenic substrate cleavage.

Figure 41:
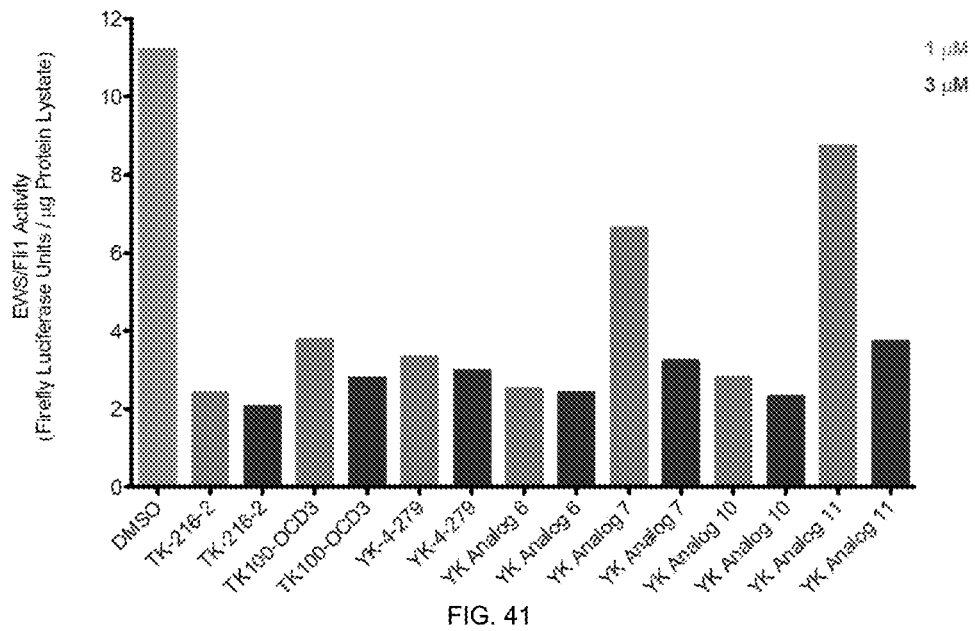

FIG. 41 provides EWS/Fli1 activity (firefly luciferase units/μg protein lysate) for various compounds and analogs at 1 μM and 3 μM concentrations.

DETAILED DESCRIPTION

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention Chromosomal translocations generating oncogenic transcription factors are the hallmark of a variety of tumors, including many sarcomas. Ewing sarcoma family of tumors (ESFTs) are characterized by the t(11; 22)(q24; q12) translocation that generates the Ewing sarcoma breakpoint region 1 and Friend leukemia virus integration 1 (EWS-FLI1) fusion transcription factor responsible for the highly malignant phenotype of this tumor. Continued expression of EWS-FLI1 is believed to be critical for ESFT cell survival. EWS-FLI1 is an attractive treatment target for Ewing sarcoma because of its malignant cell specificity. Furthermore, experimental evidence indicates that EWS/FLI expression is essential for Ewing sarcoma tumor cells. In vitro targeting of EWS-FLI1 with antisense oligodeoxynucleotides and RNA interference (RNAi) inhibits Ewing sarcoma cell viability, growth, and oncogenic transformation, supporting EWS-FLI1 attenuation as a potential treatment modality. The therapeutic agents of the preferred embodiments have broad applicability to a larger group of tumors, and are useful as therapeutics for treatment for other oncogenic transcription factor related malignancies such as chemotherapy-resistant sarcomas and leukemias and difficult to treat tumors such as Ewing's sarcoma.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, and $R_{12}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

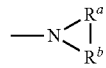

In addition, if two "R" groups are described as being "taken together" with the atom(s) to which they are attached to form a ring as an alternative, the R groups may not be limited to the variables or substituents defined previously.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from methyl, ethyl, propyl, iso-propyl, n-butyl, iso-butyl, sec-butyl, and t-butyl, pentyl (straight and branched) and hexyl (straight and branched). Typical alkyl groups include, but are in no way limited to, methyl, ethyl, propyl, isopropyl, butyl, isobutyl, tertiary butyl, pentyl (straight and branched) and hexyl (straight and branched). The alkyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "aryl" refers to a carbocyclic (all carbon) mono-cyclic or multi-cyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a mono-cyclic or multi-cyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, heterocycloalkyl refers to three-, four-, five-, six-, seven-, eight-, nine-, ten-, up to 18-membered mono-cyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocycloalky may be quaternized. Heterocycloalkyl groups may be unsubstituted or substituted. Examples of such heterocycloalkyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline and 3,4-methylenedioxyphenyl).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl) methylamine, $C_1$-$C_7$ alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium), hydrogen-2 (deuterium), and hydrogen-3 (tritium). In any chemical formulae presented herein, it is to be understood that H represents protium, D represents deuterium, and T represents tritium.

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Similarly, isotopes of carbon are also contemplated, e.g., carbon-12 ($^{12}C$), carbon-13 ($^{13}C$), and carbon-14 ($^{14}C$). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

In a first aspect a compound is provided having Formula (I):

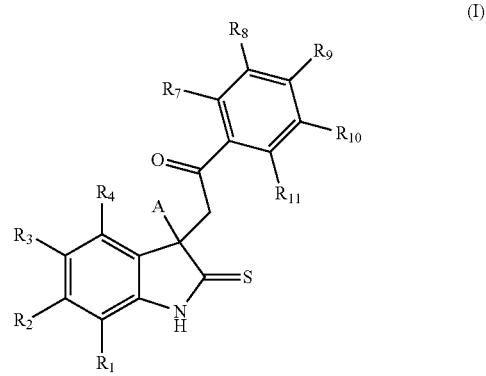

or a stereoisomer, a pharmaceutically acceptable salt, or solvate thereof, wherein A is selected from the group consisting of —OH, D, H, F, and —NH$_2$; wherein $R_1$, $R_2$, $R_3$, and $R_4$ are independently selected from the group consisting of H, Cl, —CN, —CF$_3$, $C_{1-6}$ alkyl, $C_{1-6}$ alkoxy, —C(=O)NH$_2$, —NO$_2$, —NH$_2$, and —OH; and wherein $R_7$, $R_8$, $R_9$, $R_{10}$ and $R_{11}$ are independently selected from the group consisting of H, D, F, Cl, halogen, CN, CF$_3$, $C_{1-6}$ alkyl, aryl, heteroaryl, —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$($C_{1-6}$ alkyl), —SO$_2$NH$_2$, —SO$_2$NH($C_{1-6}$ alkyl), —SO$_2$N($C_{1-6}$ alkyl)$_2$, $C_{3-8}$ cycloalkyl, and $C_{3-8}$ heterocycloalkyl.

In an embodiment of the first aspect, $R_1$, $R_2$, $R_3$, and $R_4$ are independently selected from the group consisting of H and Cl.

In an embodiment of the first aspect, $R_1$ and $R_4$ are Cl and $R_2$ and $R_3$ are H.

In an embodiment of the first aspect, A is —OH.

In an embodiment of the first aspect, $R_7$, $R_8$, $R_{10}$, and $R_{11}$ are H.

In an embodiment of the first aspect, $R_9$ is —OCH$_3$.

In an embodiment of the first aspect, the compound has a Formula (I-12):

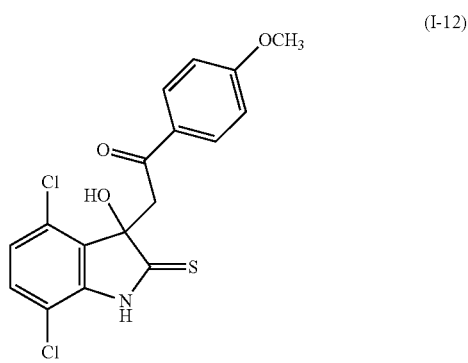 [SMILES: COc1ccc(C(=O)CC2(O)C(=S)Nc3c(Cl)ccc(Cl)c32)cc1]

In a second aspect a compound is provided having Formula (II):

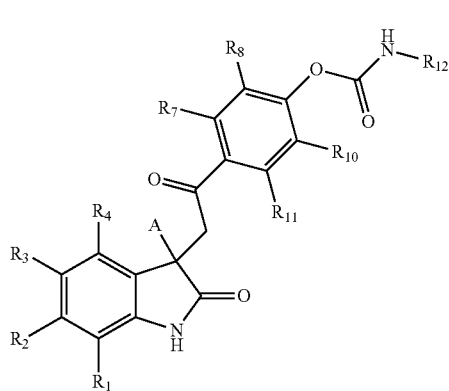

(II)

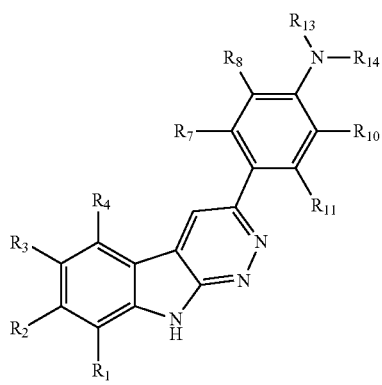

(III)

or a stereoisomer, a pharmaceutically acceptable salt, or solvate thereof, wherein A is selected from the group consisting of —OH, D, H, F, and —NH$_2$; wherein R$_1$, R$_2$, R$_3$, and R$_4$ are independently selected from the group consisting of H, Cl, —CN, —CF$_3$, C$_{1-6}$ alkyl, C$_{1-6}$ alkoxy, —C(=O)NH$_2$, —NO$_2$, —NH$_2$, and —OH; R$_7$, R$_8$, R$_{10}$, and R$_{11}$ are independently selected from the group consisting of H, D, F, Cl, halogen, CN, CF$_3$, C$_{1-6}$ alkyl, aryl, heteroaryl, —O(aryl), —O(heteroaryl), —CO$_2$H, —CO$_2$(C$_{1-6}$ alkyl), —NHSO$_2$(C$_{1-6}$ alkyl), —NHSO$_2$(aryl), —NHCONH(C$_{1-6}$ alkyl), —NHCON(C$_{1-6}$ alkyl)$_2$, —N(C$_{1-6}$ alkyl)CONH$_2$, —N(C$_{1-6}$ alkyl)CONH(C$_{1-6}$ alkyl), —N(C$_{1-6}$ alkyl)CON(C$_{1-6}$ alkyl)$_2$, —SO$_2$(C$_{1-6}$ alkyl), —SO$_2$NH$_2$, —SO$_2$NH(C$_{1-6}$ alkyl), —SO$_2$N(C$_{1-6}$ alkyl)$_2$, C$_{3-8}$ cycloalkyl, and C$_{3-8}$ heterocycloalkyl; and wherein R$_{12}$ is substituted or unsubstituted C$_{1-6}$ alkyl.

In an embodiment of the second aspect, R$_1$, R$_2$, R$_3$, and R$_4$ are independently selected from the group consisting of H and Cl.

In an embodiment of the second aspect, R$_1$, R$_2$, R$_3$, and R$_4$ are independently selected from the group consisting of H and Cl.

In an embodiment of the second aspect, A is —OH.

In an embodiment of the second aspect, R$_7$, R$_8$, R$_{10}$, and R$_{11}$ are H.

In an embodiment of the second aspect, R$_{12}$ is —CH$_3$.

In an embodiment of the second aspect, the compound has a Formula (II-13):

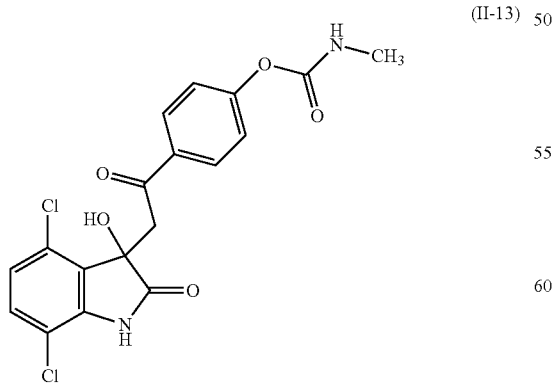

(II-13)

In a third aspect a compound is provided having Formula (III):

or a stereoisomer, a pharmaceutically acceptable salt, or solvate thereof, wherein R$_1$, R$_2$, R$_3$, and R$_4$ are independently selected from the group consisting of H, Cl, —CN, —CF$_3$, C$_{1-6}$ alkyl, C$_{1-6}$ alkoxy, —C(=O)NH$_2$, —NO$_2$, —NH$_2$, and —OH; wherein R$_7$, R$_8$, R$_{10}$ and R$_{11}$ are independently selected from the group consisting of H, D, F, Cl, halogen, CN, CF$_3$, C$_{1-6}$ alkyl, aryl, heteroaryl, —O(aryl), —O(heteroaryl), —CO$_2$H, —CO$_2$(C$_{1-6}$ alkyl), —NHSO$_2$(C$_{1-6}$ alkyl), —NHSO$_2$(aryl), —NHCONH(C$_{1-6}$ alkyl), —NHCON(C$_{1-6}$ alkyl)$_2$, —N(C$_{1-6}$ alkyl)CONH$_2$, —N(C$_{1-6}$ alkyl)CONH(C$_{1-6}$ alkyl), —N(C$_{1-6}$ alkyl)CON(C$_{1-6}$ alkyl)$_2$, —SO$_2$(C$_{1-6}$ alkyl), —SO$_2$NH$_2$, —SO$_2$NH(C$_{1-6}$ alkyl), —SO$_2$N(C$_{1-6}$ alkyl)$_2$, C$_{3-8}$ cycloalkyl, and C$_{3-8}$ heterocycloalkyl; and wherein R$_{12}$ and R$_{13}$ are independently substituted or unsubstituted C$_{1-6}$ alkyl.

In an embodiment of the third aspect, R$_1$, R$_2$, R$_3$, and R$_4$ are independently selected from the group consisting of H and Cl.

In an embodiment of the third aspect, R$_1$ and R$_4$ are Cl and R$_2$ and R$_3$ are H.

In an embodiment of the third aspect, R$_7$, R$_8$, R$_{10}$, and R$_{11}$ are H.

In an embodiment of the third aspect, R$_{12}$ and R$_{13}$ are —CH$_3$.

In an embodiment of the third aspect, the compound has a Formula (III-14):

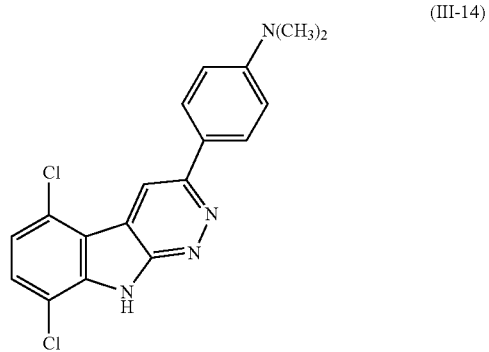 [SMILES: CN(C)c1ccc(-c2cc3c(nn2)[nH]c2c(Cl)ccc(Cl)c23)cc1]

(III-14)

In a fourth aspect a compound is provided having a Formula (IV-A), (IV-B), (IV-C), or (IV-D):

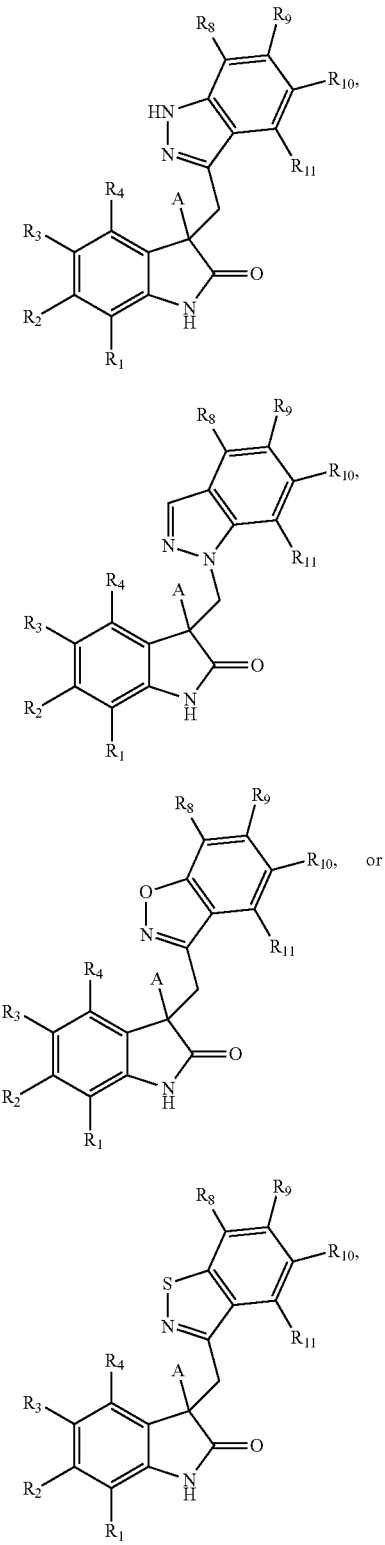

or a stereoisomer, a pharmaceutically acceptable salt, or solvate thereof, wherein A is selected from the group consisting of —OH, D, H, F, and —NH$_2$; wherein $R_1$, $R_2$, $R_3$, and $R_4$ are independently selected from the group consisting of H, Cl, —CN, —CF$_3$, C$_{1-6}$ alkyl, C$_{1-6}$ alkoxy, —C(═O) NH$_2$, —NO$_2$, —NH$_2$, and —OH; and wherein $R_8$, $R_9$, $R_{10}$ and $R_{11}$ are independently selected from the group consisting of H, D, F, Cl, halogen, CN, CF$_3$, C$_{1-6}$ alkyl, aryl, heteroaryl, —O(aryl), —O(heteroaryl), —CO$_2$H, —CO$_2$(C$_{1-6}$ alkyl), —NHSO$_2$(C$_{1-6}$ alkyl), —NHSO$_2$(aryl), —NHCONH(C$_{1-6}$ alkyl), —NHCON(C$_{1-6}$ alkyl)$_2$, —N(C$_{1-6}$ alkyl)CONH$_2$, —N(C$_{1-6}$alkyl)CONH(C$_{1-6}$ alkyl), —N(C$_{1-6}$ alkyl)CON(C$_{1-6}$ alkyl)$_2$, —SO$_2$(C$_{1-6}$ alkyl), —SO$_2$NH$_2$, —SO$_2$NH(C$_{1-6}$ alkyl), —SO$_2$N(C$_{1-6}$ alkyl)$_2$, C$_{3-8}$ cycloalkyl, and C$_{3-8}$ heterocycloalkyl.

In an embodiment of the fourth aspect, $R_1$, $R_2$, $R_3$, and $R_4$ are independently selected from the group consisting of H and Cl.

In an embodiment of the fourth aspect, $R_1$ and $R_4$ are Cl and $R_2$ and $R_3$ are H.

In an embodiment of the fourth aspect, A is —OH.

In an embodiment of the fourth aspect, $R_8$, $R_{10}$, and $R_{11}$ are H.

In an embodiment of the fourth aspect, $R_9$ is H.

In an embodiment of the second aspect, the compound has a Formula (IV-15), (IV-16), (IV-17), or (IV-18):

-continued (IV-18)

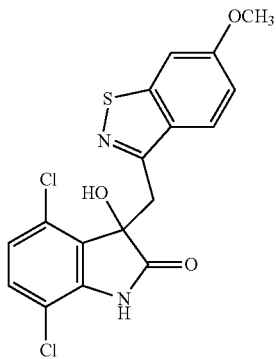

In a fifth aspect a compound is provided having Formula (V):

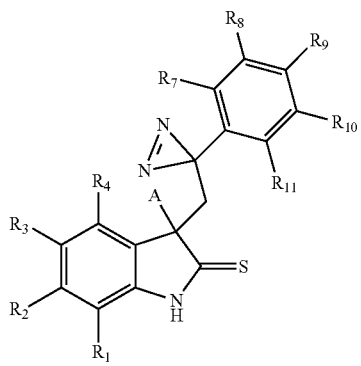

(V)

or a stereoisomer, a pharmaceutically acceptable salt, or solvate thereof, wherein A is selected from the group consisting of —OH, D, H, F, and —NH$_2$; wherein R$_1$, R$_2$, R$_3$, and R$_4$ are independently selected from the group consisting of H, Cl, —CN, —CF$_3$, C$_{1-6}$ alkyl, C$_{1-6}$ alkoxy, —C(=O)NH$_2$, —NO$_2$, —NH$_2$, and —OH; and wherein R$_7$, R$_8$, R$_9$, R$_{10}$ and R$_{11}$ are independently selected from the group consisting of H, D, F, Cl, halogen, CN, CF$_3$, C$_{1-6}$ alkyl, aryl, heteroaryl, —O(aryl), —O(heteroaryl), —CO$_2$H, —CO$_2$(C$_{1-6}$ alkyl), —NHSO$_2$(C$_{1-6}$ alkyl), —NHSO$_2$(aryl), —NHCONH(C$_{1-6}$ alkyl), —NHCON(C$_{1-6}$ alkyl)$_2$, —N(C$_{1-6}$ alkyl)CONH$_2$, —N(C$_{1-6}$ alkyl)CONH(C$_{1-6}$ alkyl), —N(C$_{1-6}$ alkyl)CON(C$_{1-6}$ alkyl)$_2$, —SO$_2$(C$_{1-6}$ alkyl), —SO$_2$NH$_2$, —SO$_2$NH(C$_{1-6}$ alkyl), —SO$_2$N(C$_{1-6}$ alkyl)$_2$, C$_{3-8}$ cycloalkyl, and C$_{3-8}$ heterocycloalkyl.

In an embodiment of the fifth aspect, R$_1$, R$_2$, R$_3$, and R$_4$ are independently selected from the group consisting of H and Cl.

In an embodiment of the fifth aspect, R$_1$ and R$_4$ are Cl and R$_2$ and R$_3$ are H.

In an embodiment of the fifth aspect, A is —OH.

In an embodiment of the fifth aspect, R$_7$, R$_8$, R$_{10}$, and R$_{11}$ are H.

In an embodiment of the fifth aspect, R$_9$ is —OCH$_3$.

In an embodiment of the fifth aspect, the compound has a Formula (V-19):

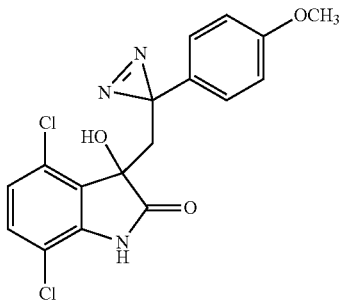

(V-19)

In a sixth aspect a compound is provided having Formula (VI):

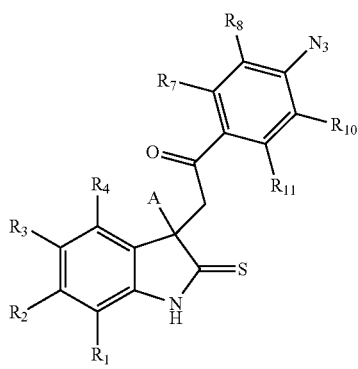

(VI)

or a stereoisomer, a pharmaceutically acceptable salt, or solvate thereof, wherein A is selected from the group consisting of —OH, D, H, F, and —NH$_2$; wherein R$_1$, R$_2$, R$_3$, and R$_4$ are independently selected from the group consisting of H, Cl, —CN, —CF$_3$, C$_{1-6}$ alkyl, C$_{1-6}$ alkoxy, —C(=O)NH$_2$, —NO$_2$, —NH$_2$, and —OH; and wherein R$_7$, R$_8$, R$_{10}$, and R$_{11}$ are independently selected from the group consisting of H, D, F, Cl, halogen, CN, CF$_3$, C$_{1-6}$ alkyl, aryl, heteroaryl, —O(aryl), —O(heteroaryl), —CO$_2$H, —CO$_2$(C$_{1-6}$ alkyl), —NHSO$_2$(C$_{1-6}$ alkyl), —NHSO$_2$(aryl), —NHCONH(C$_{1-6}$ alkyl), —NHCON(C$_{1-6}$ alkyl)$_2$, —N(C$_{1-6}$ alkyl)CONH$_2$, —N(C$_{1-6}$ alkyl)CONH(C$_{1-6}$ alkyl), —N(C$_{1-6}$ alkyl)CON(C$_{1-6}$ alkyl)$_2$, —SO$_2$(C$_{1-6}$ alkyl), —SO$_2$NH$_2$, —SO$_2$NH(C$_{1-6}$ alkyl), —SO$_2$N(C$_{1-6}$ alkyl)$_2$, C$_{3-8}$ cycloalkyl, and C$_{3-s}$ heterocycloalkyl.

In an embodiment of the sixth aspect, R$_1$, R$_2$, R$_3$, and R$_4$ are independently selected from the group consisting of H and Cl.

In an embodiment of the sixth aspect, R$_1$ and R$_4$ are Cl and R$_2$ and R$_3$ are H.

In an embodiment of the sixth aspect, A is —OH.

In an embodiment of the sixth aspect, R$_7$, R$_8$, R$_{10}$, and R$_{11}$ are H.

In an embodiment of the sixth aspect, the compound has a Formula (VI-20):

(VI-20)

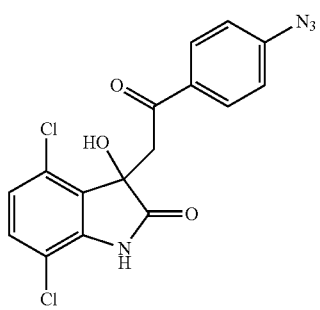

In a seventh aspect a compound is provided having Formula (VII):

(VII)

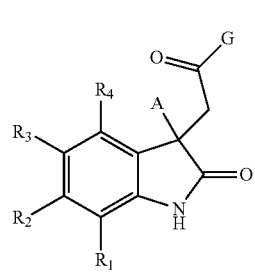

or a stereoisomer, a pharmaceutically acceptable salt, or solvate thereof, wherein A is selected from the group consisting of —OH, D, H, F, and —NH$_2$; wherein $R_1$, $R_2$, $R_3$, and $R_4$ are independently selected from the group consisting of H, Cl, —CN, —CF$_3$, C$_{1-6}$ alkyl, C$_{1-6}$ alkoxy, —C(=O)NH$_2$, —NO$_2$, —NH$_2$, and —OH; and wherein G is selected from the group consisting of

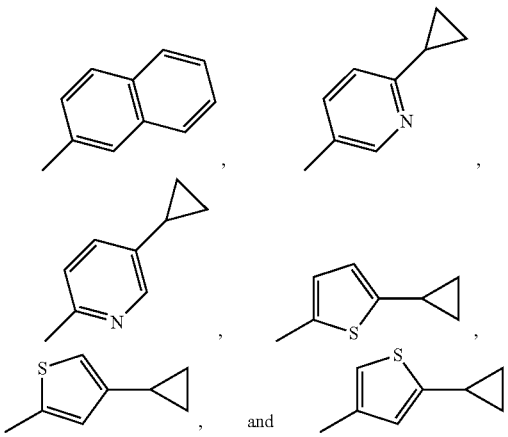

, and

.

In an embodiment of the seventh aspect, $R_1$, $R_2$, $R_3$, and $R_4$ are independently selected from the group consisting of H and Cl.

In an embodiment of the seventh aspect, $R_1$ and $R_4$ are Cl, and $R_2$ and $R_3$ are H.

In an embodiment of the seventh aspect, A is —OH.

In an embodiment of the seventh aspect, the compound has a Formula (VII-20-21):

(VII-19)

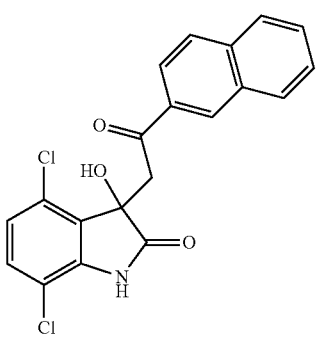

(VII-20)

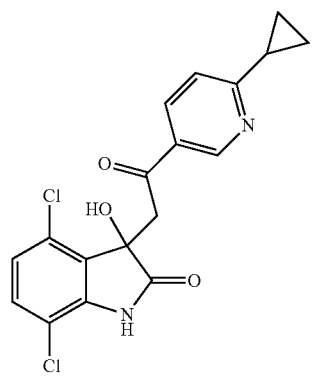

(VII-21)

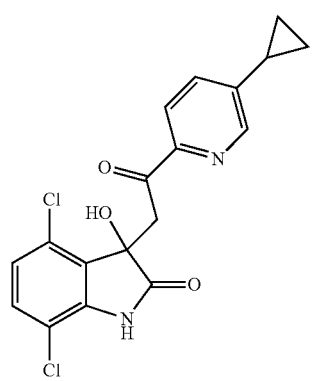

(VII-22)

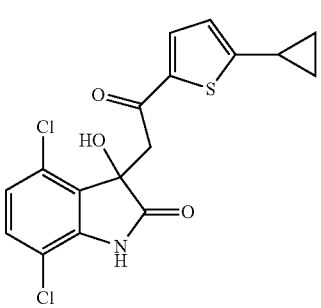

-continued (VII-23)

[Chemical structure: 4,7-dichloro-3-hydroxy-3-(2-(4-cyclopropylthiophen-2-yl)-2-oxoethyl)indolin-2-one]

(VII-24)

[Chemical structure: 4,7-dichloro-3-hydroxy-3-(2-(5-cyclopropylthiophen-3-yl)-2-oxoethyl)indolin-2-one]

In an eighth aspect, a pharmaceutical composition comprising the compound of any of the first through sixth aspects or any embodiment thereof and a pharmaceutically acceptable carrier is provided.

In an ninth aspect, a pharmaceutical composition comprising the compound of any of the first through sixth aspects or any embodiment thereof and a pharmaceutically acceptable excipient is provided.

In a tenth aspect, a pharmaceutical composition is provided comprising the compound of any of the first through sixth aspects or any embodiment thereof and at least one additional pharmaceutically active agent.

In a eleventh aspect, a method for treating cancer is provided comprising administering an effective amount of the compound of the first aspect or any embodiment thereof to a subject in need thereof.

In an embodiment of the eleventh aspect, the subject is mammalian.

In an embodiment of the eleventh aspect, the subject is human.

In an embodiment of the eleventh aspect, the cancer is selected from the group consisting of Ewing's sarcoma, prostate cancer, glioblastoma, acute myeloid leukemia, breast cancer, head and neck cancer, melanoma, non-small cell lung cancer, ovarian cancer, and uterine cancer.

In an twelfth aspect, a method of killing or inhibiting the growth of a neoplastic cell is provided, comprising contacting the cell with an effective amount of the compound of the first aspect or any embodiment thereof.

In an embodiment of the twelfth aspect, the cell is mammalian.

In an embodiment of the twelfth aspect, the cell is human.

In an embodiment of the twelfth aspect, the cell is in vitro.

In an embodiment of the twelfth aspect, the cell is in vivo.

In an embodiment of the twelfth aspect, the cell is a cancer cell, the cancer being selected from the group consisting of Ewing's sarcoma, prostate cancer, glioblastoma, acute myeloid leukemia, breast cancer, head & neck cancer, melanoma, non-small cell lung cancer, ovarian cancer, and uterine cancer.

In a thirteenth aspect, a method for inhibiting proliferation of a cell, wherein the cell overexpresses an ETS gene or comprises an ETS fusion gene, comprising contacting the cell with an effective amount of the compound of the first aspect or any embodiment thereof.

In an embodiment of the thirteenth aspect, the ETS gene or the ETS fusion gene is selected from the group consisting of FLI1, ERG, ETV1, and ETV4.

In an embodiment of the thirteenth aspect, the cell is mammalian.

In an embodiment of the thirteenth aspect, the cell is human.

In an embodiment of the thirteenth aspect, the cell is in vitro.

In an embodiment of the thirteenth aspect, the cell is in vivo.

In an embodiment of the thirteenth aspect, the cell is a cancer cell, the cancer being selected from the group consisting of Ewing's sarcoma, prostate cancer, glioblastoma, acute myeloid leukemia, breast cancer, head & neck cancer, melanoma, non-small cell lung cancer, ovarian cancer, and uterine cancer.

Any of the features of an embodiment of the first through thirteenth aspects is applicable to all aspects and embodiments identified herein. Moreover, any of the features of an embodiment of the first through thirteenth aspects is independently combinable, partly or wholly with other embodiments described herein in any way, e.g., one, two, or three or more embodiments may be combinable in whole or in part. Further, any of the features of an embodiment of the first through thirteenth aspects may be made optional to other aspects or embodiments. Any aspect or embodiment of a method can be performed using a compound or composition of another aspect or embodiment, and any aspect or embodiment of a compound or composition can be used to perform a method of another aspect or embodiment.

Synthetic Methods

Compounds of Formulae (I)-(VII) described herein may be prepared in various ways. General synthetic routes to compounds of Formulae (I)-(VII) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I)

Compounds of Formula (I) can be prepared by the following synthetic route. The synthetic route is a modification of a route described in Thompson et al. "Tyrosine Kinase Inhibitors. 1. Structure-Activity Relationships for Inhibition of Epidermal Growth Factor Receptor Tyrosine Kinase Activity by 2,3-Dihydro-2-thioxo-1H-indole-3-alkanoic Acids and 2,2'-Dithiobis(1 H-indole-3-alkanoic acids)" J. Med. Chem. 1993, 36, 2459-2469, the contents of which are hereby incorporated by reference in their entirety.

[Chemical structure: 4,7-dichloroisatin] +

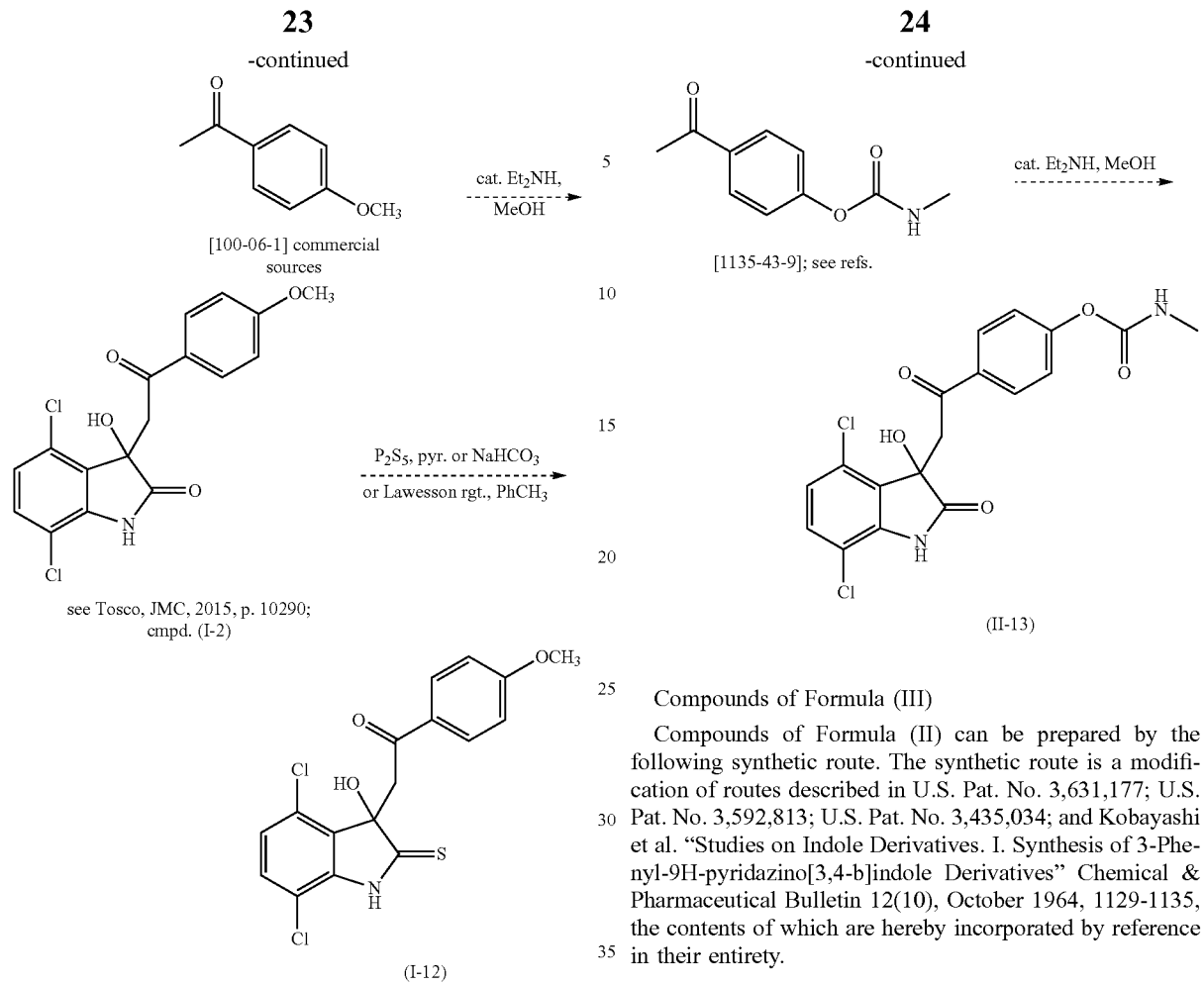

Compounds of Formula (II)

Compounds of Formula (II) can be prepared by the following synthetic route. The synthetic route is a modification of routes described in Al-Rawi, H.; Williams, A.; Journal of the American Chemical Society; vol. 99; (1977); p. 2671-2678; Kulkarni; Naik; Tandel; Rajappa; Tetrahedron; vol. 47; nb. 7; (1991); p. 1249-1256; Deshpande, Sunita R.; Likhite, Anjali P.; Rajappa, Srinivasachari; Tetrahedron; vol. 50; nb. 34; (1994); p. 10367-10370; Al Sabbagh, Mohamed Mowafak; Calmon, Michelle; Calmon, Jean-Pierre; Bulletin de la Societe Chimique de France; vol. 2; nb. 3-4; (1983); p. 73-77; Iwakura; Nabeya; Journal of Organic Chemistry; vol. 26; (1961); p. 4384, 4387; Iwakura; Nabeya; Journal of Organic Chemistry; vol. 26; (1961); p. 4384, 4387; Schwezowa-Schilowskaja et al.; J. Gen. Chem. USSR (Engl. Transl.); vol. 33; (1963); p. 2109, 2054; and U.S. Pat. No. 4,376,731, the contents of which are hereby incorporated by reference in their entirety.

Compounds of Formula (III)

Compounds of Formula (II) can be prepared by the following synthetic route. The synthetic route is a modification of routes described in U.S. Pat. No. 3,631,177; U.S. Pat. No. 3,592,813; U.S. Pat. No. 3,435,034; and Kobayashi et al. "Studies on Indole Derivatives. I. Synthesis of 3-Phenyl-9H-pyridazino[3,4-b]indole Derivatives" Chemical & Pharmaceutical Bulletin 12(10), October 1964, 1129-1135, the contents of which are hereby incorporated by reference in their entirety.

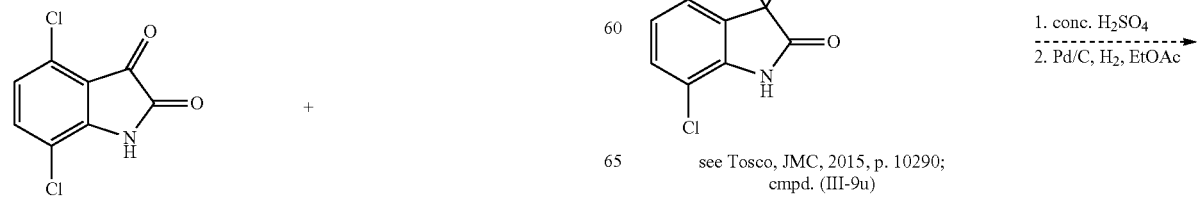

-continued

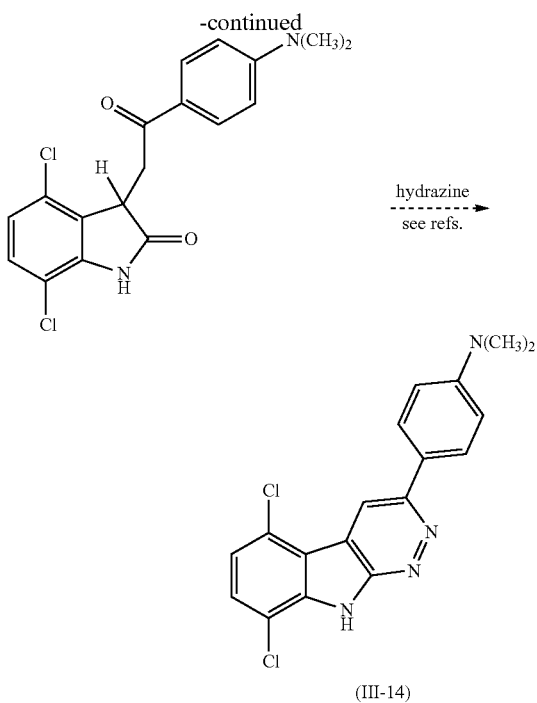

(III-14)

Compounds of Formula (IV)

Compounds of Formula (IV) can be prepared by the following synthetic routes.

Compounds of Formula (IV-A)

Two alternative routes can be employed to prepare compounds of Formula (IV-A). In one approach, the indazole is formed in the last step of the synthetic sequence via intramolecular displacement of the fluorine atom of penultimate intermediate (IV-15A). Elevated temperatures may be required, however, and this may lead to elimination of a tertiary hydroxyl group leading to the E/Z olefin.

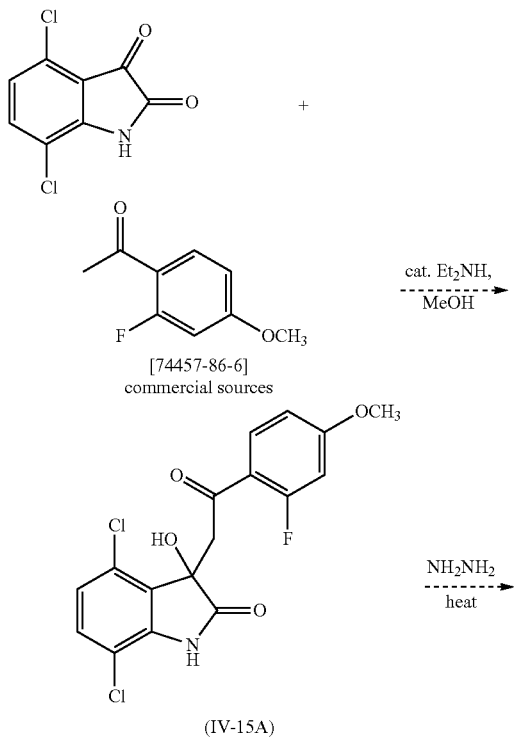

-continued

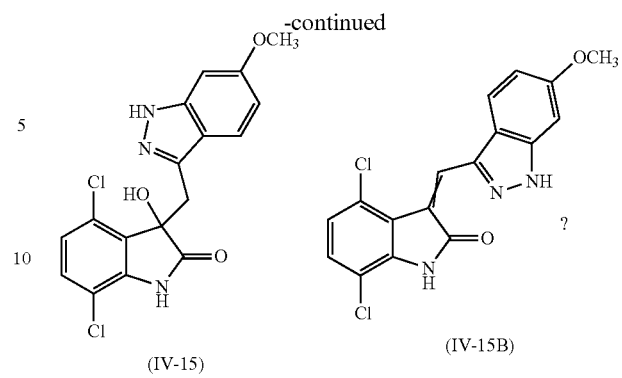

(IV-15)  (IV-15B)

An alternative synthetic approach involves use of an organometallic indazole reagent that may be generated by different methods, either as the Li or Mg organometallic by direct deprotonation or halogen exchange. Cuprates can also be used when opening epoxides, as described in WO2004/18441; WO2006/135826; Lipshutz et al., Journal of Organic Chemistry; vol. 49; nb. 21; (1984); p. 3928-3938; Sone et al., Journal of the American Chemical Society; vol. 130; nb. 31; (2008); p. 10078-10079; WO2012/177603; Chen et al., Journal of Organic Chemistry; vol. 62; nb. 13; (1997); p. 4349-4357; Yadav et al., Tetrahedron Letters; vol. 42; nb. 13; (2001); p. 2557-2559; Archelas; Furstoss; Journal of Organic Chemistry; vol. 64; nb. 16; (1999); p. 6112-6114; Fujisawa et al., Chemistry Letters; (1988); p. 59-62; U.S. Pat. No. 5,057,529; Wakabayashi et al., Journal of Organic Chemistry; vol. 75; nb. 13; (2010); p. 4337-4343; Kireenko et al., Dalton Transactions; vol. 44; nb. 26; (2015); p. 11963-11976; Bawden et al., European Journal of Medicinal Chemistry; vol. 18; nb. 1; (1983); p. 91-96; Coppola et al., Journal of Heterocyclic Chemistry; vol. 18; (1981); p. 31-35; EP613890; U.S. Pat. No. 4,935,436; Cristol et al.; Journal of the American Chemical Society; vol. 73; (1951); p. 816; Lipshutz et al., Journal of the American Chemical Society; vol. 104; nb. 8; (1982); p. 2305-2307; US2016/75712; Lam et al., Chemistry—A European Journal; vol. 22; nb. 13; (2016); p. 4440-4446; Buchstaller et al., Synthesis; nb. 19; (2011); p. 3089-3098; Art. No: T48411SS; Lynch et al., Bioorganic and Medicinal Chemistry Letters; vol. 23; nb. 9; (2013); p. 2793-2800; Youngsaye et al., Beilstein Journal of Organic Chemistry; vol. 9; (2013); p. 1501-1507; Slade et al., Journal of Organic Chemistry; vol. 74; nb. 16; (2009); p. 6331-6334; Lukin et al., Journal of Organic Chemistry; vol. 71; nb. 21; (2006); p. 8166-8172; Tung et al., Journal of Medicinal Chemistry; vol. 54; nb. 8; (2011); p. 3076-3080; WO2012/3418; Wheeler et al., Organic Process Research and Development; vol. 15; nb. 3; (2011); p. 565-569; WO2014/152144; Tono-Oka et al., Bulletin of the Chemical Society of Japan; vol. 58; nb. 1; (1985); p. 309-315; Vernekar et al., Journal of Medicinal Chemistry; vol. 53; nb. 5; (2010); p. 2324-2328; Shimada et al., Bioorganic and Medicinal Chemistry; vol. 16; nb. 4; (2008); p. 1966-1982; Senwar et al., European Journal of Medicinal Chemistry; vol. 102; (2015); p. 413-424; Art. No: 8053; Hajra et al., Organic Letters; vol. 17; nb. 14; (2015); p. 3430-3433; Gorokhovik et al., Organic Letters; vol. 13; nb. 20; (2011); p. 5536-5539; Pace et al., Advanced Synthesis and Catalysis; vol. 358; nb. 2; (2016); p. 172-177; Kennewell et al., Journal of Chemical Research, Miniprint; nb. 10; (1995); p. 2380-2388; Chouhan et al., Green Chemistry; vol. 13; nb. 9; (2011); p. 2553-2560; Li et al., Organic Letters; vol. 17; nb. 5; (2015); p. 1098-1101; Allous et al., European Journal of Organic Chemistry; nb. 27; (2011); p. 5303-5310; Wille, S., Synthesis; nb. 5; (2001); p. 759-762; Aikawa et al., European Journal of Organic Chemistry; nb. 1; (2011); p. 62-65; Vyas et al., Journal of Organic Chemistry; vol. 75; nb. 19; (2010); p. 6720-6723; Banerjee et al., RSC Advances; vol. 4; nb. 63; (2014); p. 33236-33244; Sabahi et al., Angewandte Chemie—International Edition; vol. 45; nb. 26; (2006); p. 4317-4320; Noole et al., Chemistry—A European Journal; vol. 18; nb. 47; (2012); p. 14929-14933; Li et al., Angewandte Chemie—International Edition; vol. 52; nb. 17; (2013); p. 4628-4632; Quintavalla et al., Journal of Organic Chemistry; vol. 78; nb. 23; (2013); p. 12049-12064; Badiola et al., Journal of the American Chemical Society; vol. 136; nb. 51; (2014); p. 17869-17881, the contents of which are hereby incorporated by reference in their entirety. 6-Methoxy-1H-indazole can be prepared from 6-hydroxy indazole or 2-fluoro-4-methoxy-benzaldehyde.

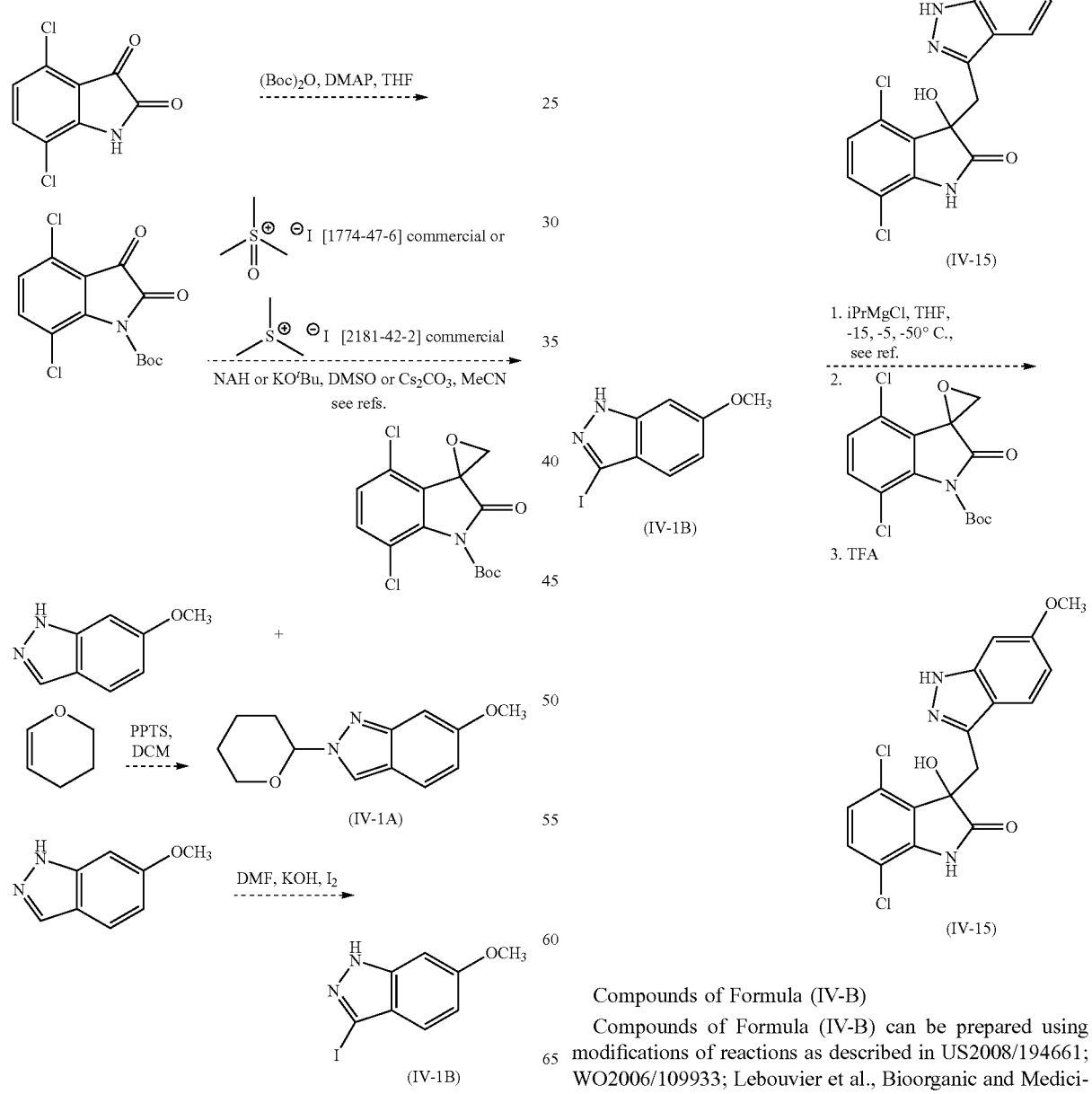

Compounds of Formula (IV-B)

Compounds of Formula (IV-B) can be prepared using modifications of reactions as described in US2008/194661; WO2006/109933; Lebouvier et al., Bioorganic and Medicinal Chemistry Letters; vol. 17; nb. 13; (2007); p. 3686-3689, the contents of which are hereby incorporated by reference in their entirety. 5-Methoxy-1H-indazole can be prepared from 2-fluoro-5-methoxy-benzaldehyde (see Lukin, J O C, 2006, p. 8166).

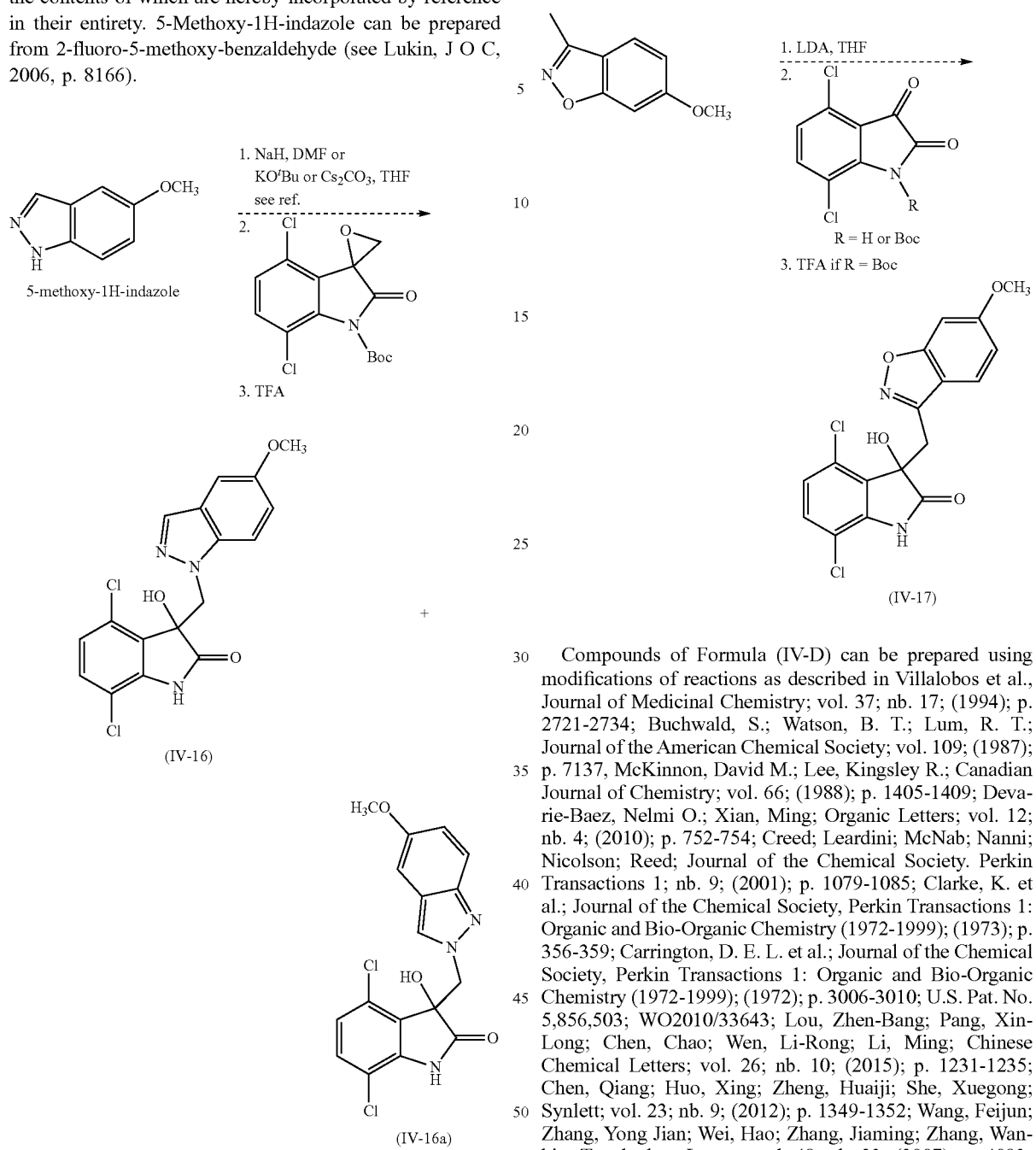

Compounds of Formula (IV-C)

Compounds of Formula (IV-C) can be prepared using modifications of reactions as described in U.S. Pat. No. 5,538,984; Chen et al., Organic Letters; vol. 13; nb. 23; (2011); p. 6300-6303; Villalobos et al., Journal of Medicinal Chemistry; vol. 37; nb. 17; (1994); p. 2721-2734; Sahasrabudhe et al., Indian Journal of Chemistry, Section B: Organic Chemistry Including Medicinal Chemistry; vol. 22; nb. 12; (1983); p. 1266-1267; U.S. Pat. No. 5,856,503, the contents of which are hereby incorporated by reference in their entirety. 6-methoxy-3-methylbenzo[d]isoxazole can be prepared from 2-hydroxy-4-methoxy-acetophenone.

Compounds of Formula (IV-D) can be prepared using modifications of reactions as described in Villalobos et al., Journal of Medicinal Chemistry; vol. 37; nb. 17; (1994); p. 2721-2734; Buchwald, S.; Watson, B. T.; Lum, R. T.; Journal of the American Chemical Society; vol. 109; (1987); p. 7137, McKinnon, David M.; Lee, Kingsley R.; Canadian Journal of Chemistry; vol. 66; (1988); p. 1405-1409; Devarie-Baez, Nelmi O.; Xian, Ming; Organic Letters; vol. 12; nb. 4; (2010); p. 752-754; Creed; Leardini; McNab; Nanni; Nicolson; Reed; Journal of the Chemical Society. Perkin Transactions 1; nb. 9; (2001); p. 1079-1085; Clarke, K. et al.; Journal of the Chemical Society, Perkin Transactions 1: Organic and Bio-Organic Chemistry (1972-1999); (1973); p. 356-359; Carrington, D. E. L. et al.; Journal of the Chemical Society, Perkin Transactions 1: Organic and Bio-Organic Chemistry (1972-1999); (1972); p. 3006-3010; U.S. Pat. No. 5,856,503; WO2010/33643; Lou, Zhen-Bang; Pang, Xin-Long; Chen, Chao; Wen, Li-Rong; Li, Ming; Chinese Chemical Letters; vol. 26; nb. 10; (2015); p. 1231-1235; Chen, Qiang; Huo, Xing; Zheng, Huaiji; She, Xuegong; Synlett; vol. 23; nb. 9; (2012); p. 1349-1352; Wang, Feijun; Zhang, Yong Jian; Wei, Hao; Zhang, Jiaming; Zhang, Wanbin; Tetrahedron Letters; vol. 48; nb. 23; (2007); p. 4083-4086; Wang, Feijun; Zhang, Yong Jian; Yang, Guoqiang; Zhang, Wanbin; Tetrahedron Letters; vol. 48; nb. 24; (2007); p. 4179-4182; Pump, Eva; Poater, Albert; Zirngast, Michaela; Torvisco, Ana; Fischer, Roland; Cavallo, Luigi; Slugovc, Christian; Organometallics; vol. 33; nb. 11; (2014); p. 2806-2813; Moreno-Sanz, Guillermo; Duranti, Andrea; Melzig, Laurin; Fiorelli, Claudio; Ruda, Gian Filippo; Colombano, Giampiero; Mestichelli, Paola; Sanchini, Silvano; Tontini, Andrea; Mor, Marco; Bandiera, Tiziano; Scarpelli, Rita; Tarzia, Giorgio; Piomelli, Daniele; Journal of Medicinal Chemistry; vol. 56; nb. 14; (2013); p. 5917-5930; WO2011/30955; US2012/214991; Oki; Bulletin of the Chemical Society of Japan; vol. 26; (1953); p. 331, 334; Zara-Kaczian, Erzsebet; Deak, Gyula; Gyoergy, Lajos; Acta Chimica Hungarica; vol. 126; nb. 4; (1989); p. 441-454;

Bartoli, Giuseppe; Bosco, Marcella; Marcantoni, Enrico; Massaccesi, Massimo; Rinaldi, Samuele; Sambri, Letizia; Tetrahedron Letters; vol. 43; nb. 36; (2002); p. 6331-6333; US2010/4159; Zhang, Xiaohong; Lou, Cong; Li, Ningbo; Xu, Xinhua; Qiu, Renhua; Yin, Shuangfeng; Journal of Organometallic Chemistry; vol. 749; (2014); p. 241-245; Tan, Lay Pheng; Wu, Hao; Yang, Peng-Yu; Kalesh, Karunakaran A.; Zhang, Xiaohua; Hu, Mingyu; Srinivasan, Rajavel; Yao, Shao Q.; Organic Letters; vol. 11; nb. 22; (2009); p. 5102-5105, the contents of which are hereby incorporated by reference in their entirety. 6-Methoxy-3-methylbenzo[d]isothiazole can be prepared from 2-fluoro-4-methoxy-acetophenone or 2-bromo-4-methoxy-acetophenone.

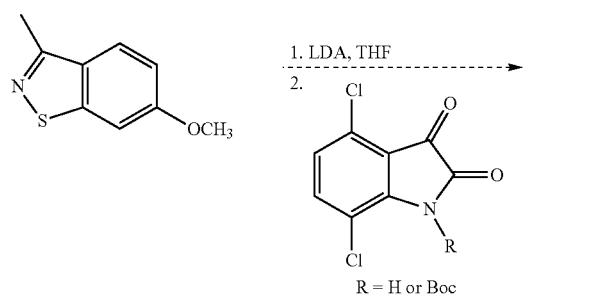

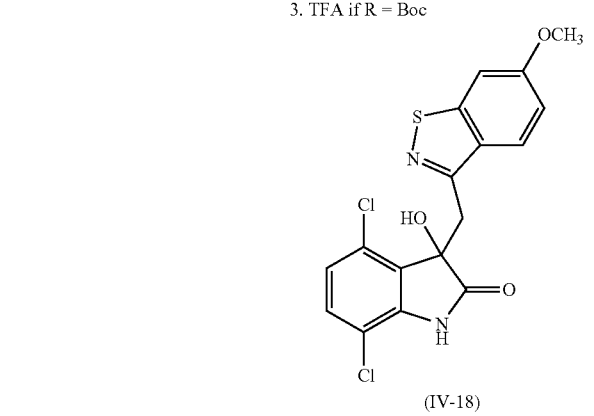

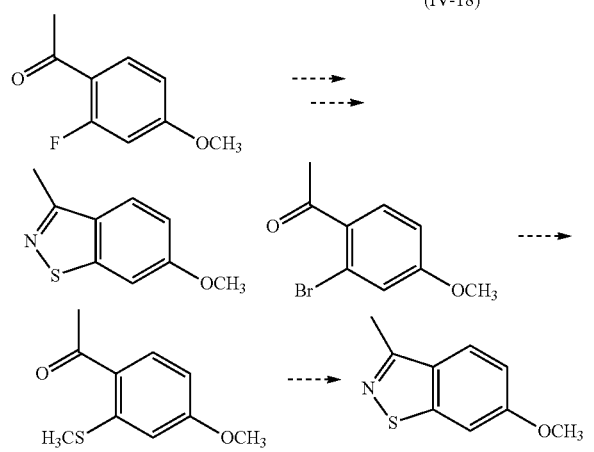

Compounds of Formula (V)

Compounds of Formula (V) can be prepared by the following synthetic route, and using modifications of reactions as described in Dubinski et al., Diazirine based photoaffinity labeling, Bioorganic & Medicinal Chemistry 20 (2012) 554-570, the contents of which are hereby incorporated by reference in their entirety.

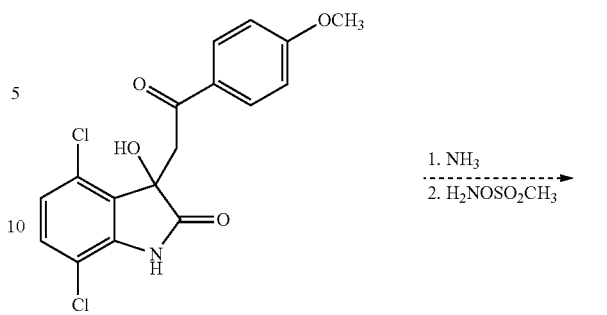

see Tosco, JMC, 2015, p. 10290; cmpd. 2

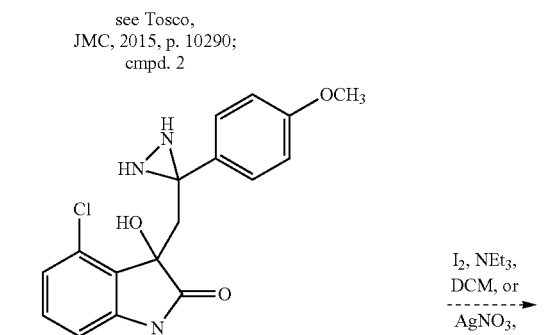

see Dubinsky, Chem. Comm., 2009, p. 7378 and Al-Omari, Angew Chem., Int. Ed., 2006, p. 309

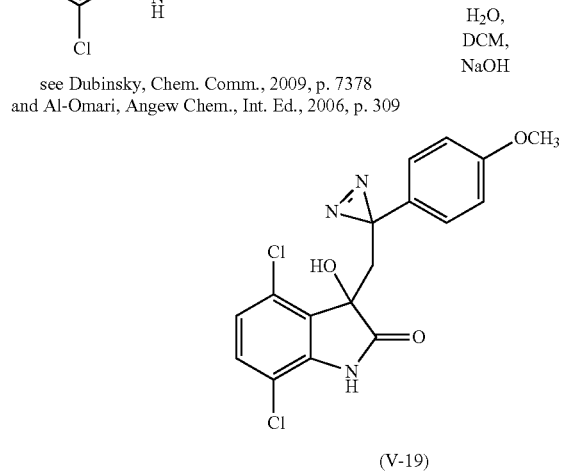

Compounds of Formula (VI)

Compounds of Formula (VI) can be prepared by the following synthetic routes. 1-(4-azidophenyl)ethan-1-one can be prepared from 4-amino-acetophenone.

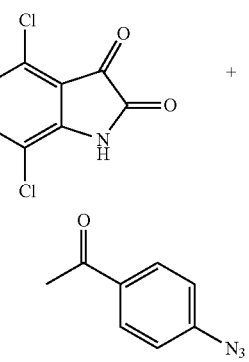

-continued

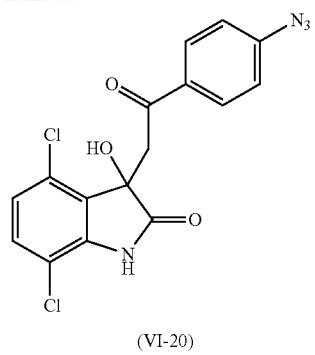

(VI-20)

An alternative route can also be employed.

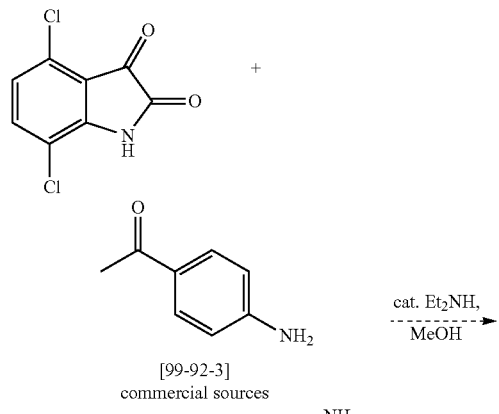

see Tosco, JMC, 2015, p. 10290; cmpd. 9s

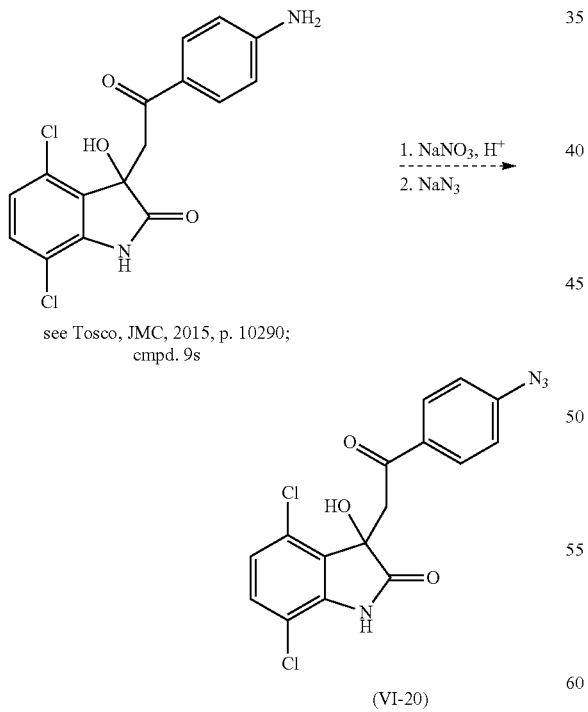

(VI-20)

Compounds of Formula (VII)

Compounds of Formula (VII) can be prepared using standard condensation conditions between the 4,7-dichloroisatin and a suitable methyl-aryl ketone. For example, see:

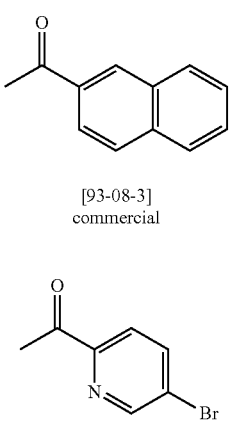

[93-08-3] commercial

[139042-59-4] commercial

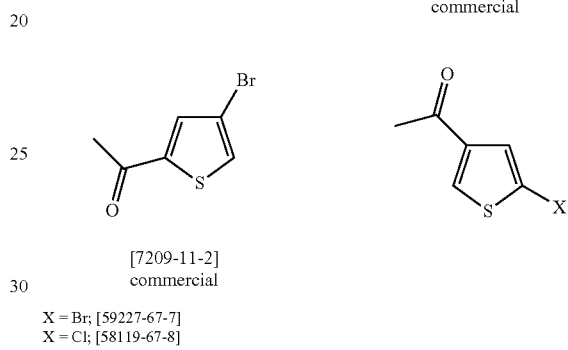

[214701-49-2]

[5370-25-2] commercial

[7209-11-2] commercial

X = Br; [59227-67-7]
X = Cl; [58119-67-8]

The following synthetic route can be employed:

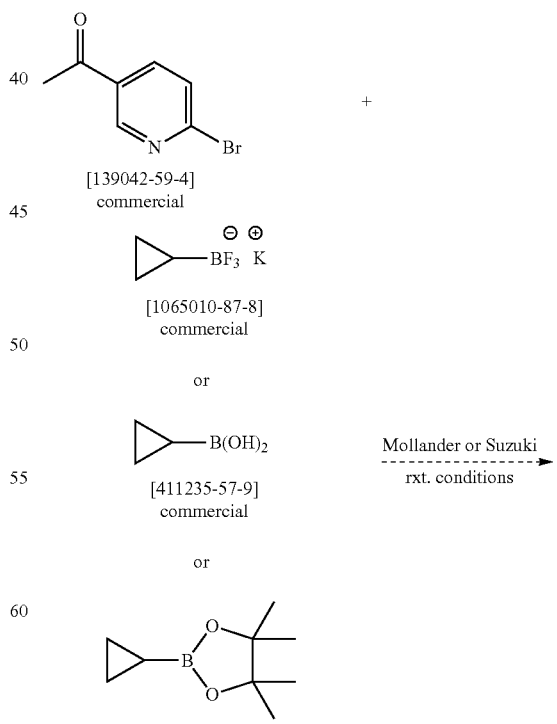

Mollander or Suzuki rxt. conditions

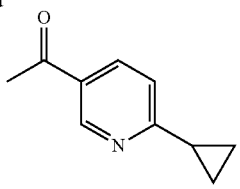

Descriptions of synthetic routes that can be adapted to the preparation of compounds of Formula (VII) include the following: Reck, et al.; Journal of Medicinal Chemistry; vol. 50; nb. 20; (2007); p. 4868-4881; WO98/46605; WO2005/116022; WO2005/116023; Markevitch, et al.; 33; 19; 2003; 3285-3290; Fosso, et al.; Organic and Biomolecular Chemistry; vol. 13; nb. 36; (2015); p. 9418-9426; WO2008/108988; Jo, et al.; Bioorganic and Medicinal Chemistry; vol. 12; nb. 22; (2004); p. 5909-5915; Abarca, et al.; Tetrahedron; vol. 64; nb. 17; (2008); p. 3794-3801; Huo, et al.; Dalton Transactions; vol. 40; nb. 29; (2011); p. 7534-7540; WO2015/27021; WO2012/21467; US2014/249132; WO2008/91681; US2010/16298; WO2013/144224; WO2013/91096; Matulenko, et al.; Bioorganic and Medicinal Chemistry; vol. 13; nb. 11; (2005); p. 3705-3720; Karlsson, Olle; Synthetic Communications; vol. 11; nb. 1; (1981); p. 29-34; Sun, et al.; Bioorganic and Medicinal Chemistry Letters; vol. 21; nb. 19; (2011); p. 5849-5853; U.S. Pat. No. 9,138,427; Stamford, et al.; ACS Medicinal Chemistry Letters; vol. 3; nb. 11; (2012); p. 897-902; US2003/114666; WO2014/31784; Stanetty, et al.; Monatshefte fuer Chemie; vol. 120; (1989); p. 53-63; Sharf, et al.; Chemistry of Heterocyclic Compounds (New York, N.Y., United States); vol. 18; nb. 2; (1982); p. 130-133; Khimiya Geterotsiklicheskikh Soedinenii; vol. 18; nb. 2; (1982); p. 171-175; Molander, et al.; Journal of Organic Chemistry; vol. 73; nb. 19; (2008); p. 7481-7485; WO2015/134701.

Salt Forms

Depending upon the substituents present, the small molecule inhibitors can be in a form of a pharmaceutically acceptable salt. The terms "pharmaceutically acceptable salt" as used herein are broad terms, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

Isomeric Forms

The compounds of preferred embodiments can include isomers, racemates, optical isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)- or (S)-configuration, or can be present as mixtures of the (R)- and (S)-forms. The following are isomeric forms of the compounds of Formulae (I)-(VII):

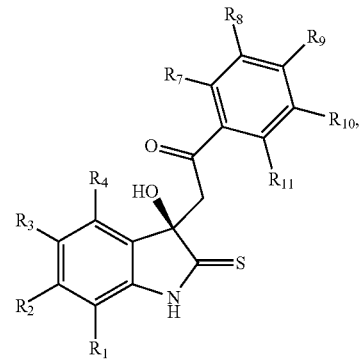

(I-a)

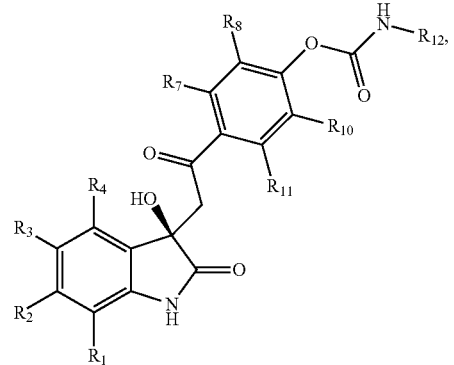

(II-a)

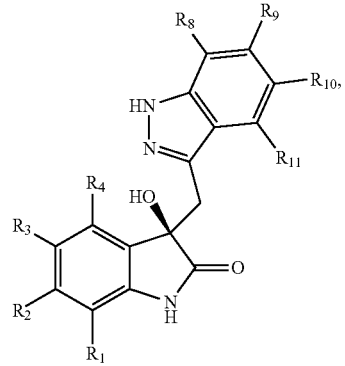

(IV-A-a)

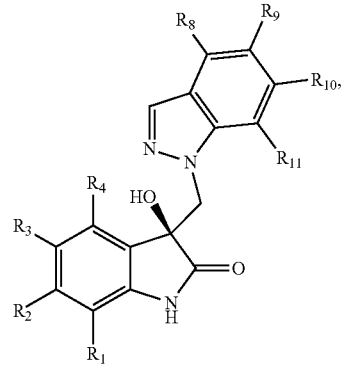

(IV-B-a)

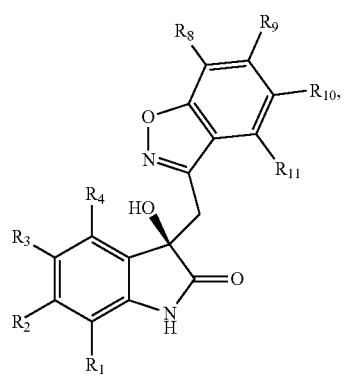
(IV-C-a)
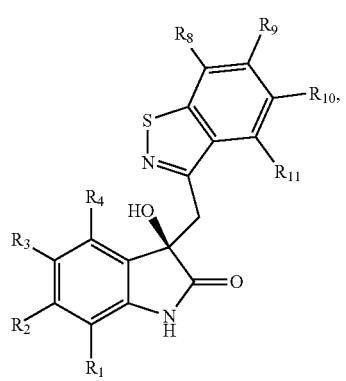
(IV-D-a)
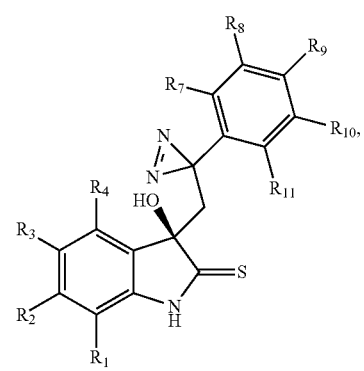
(V-a)
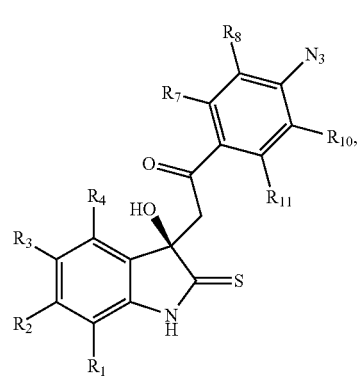
(VI-a)
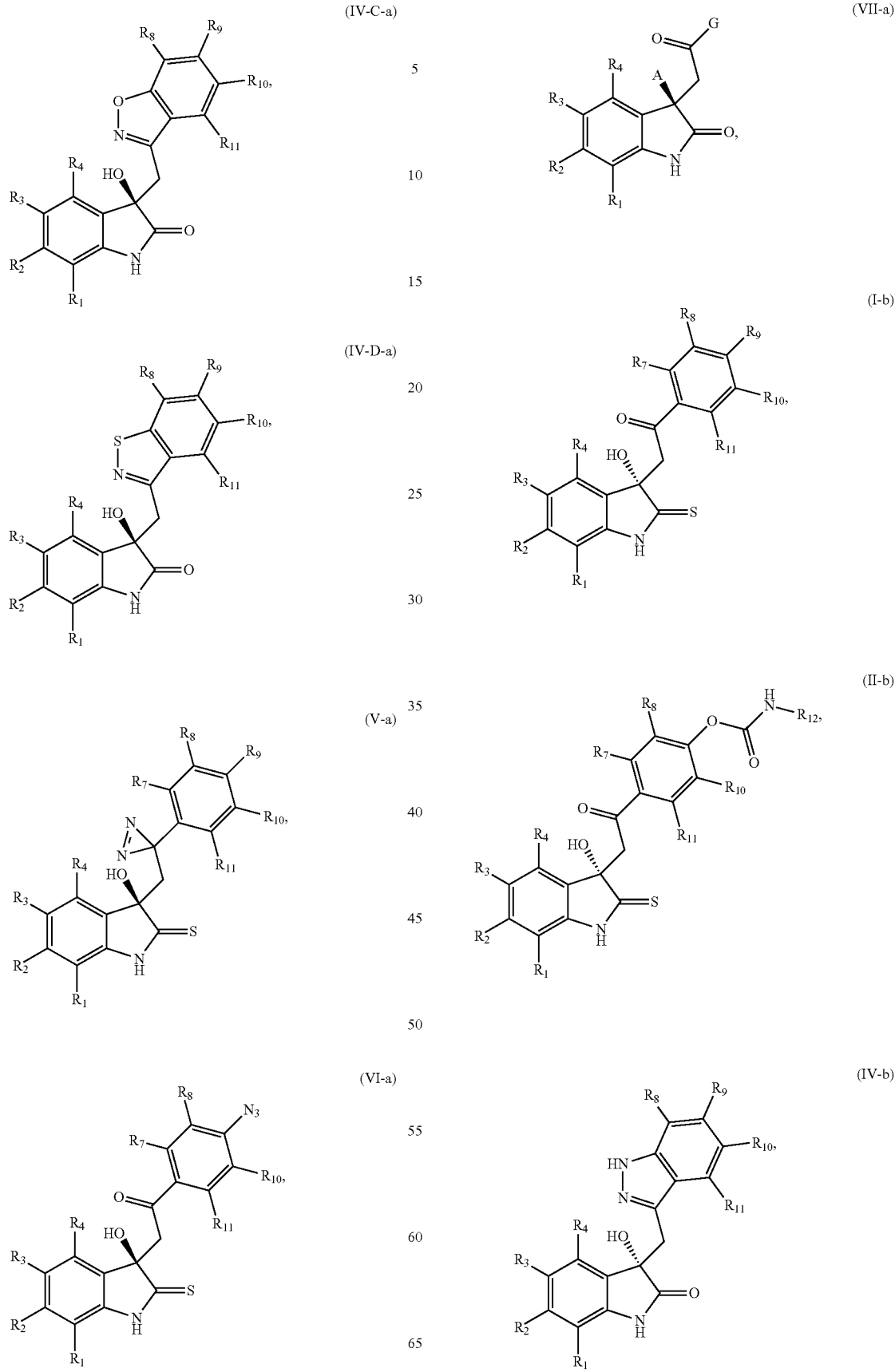

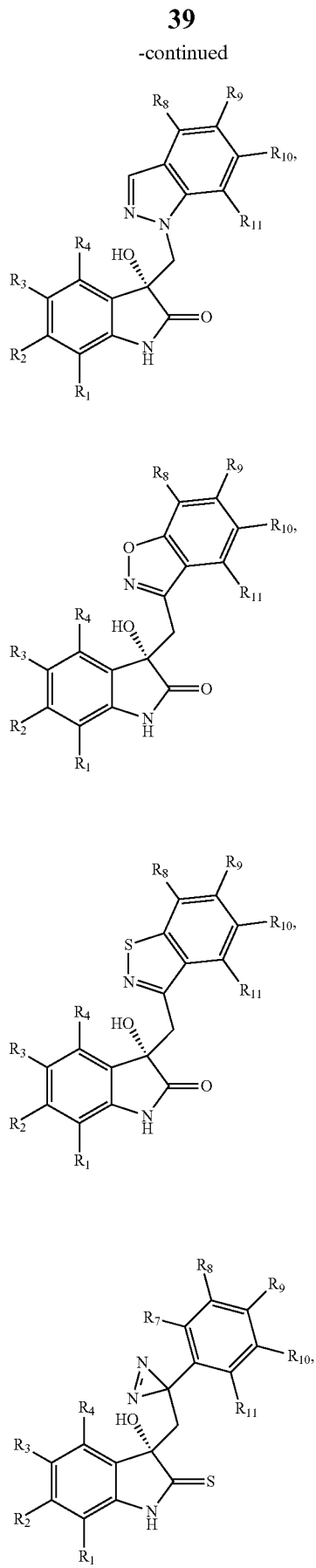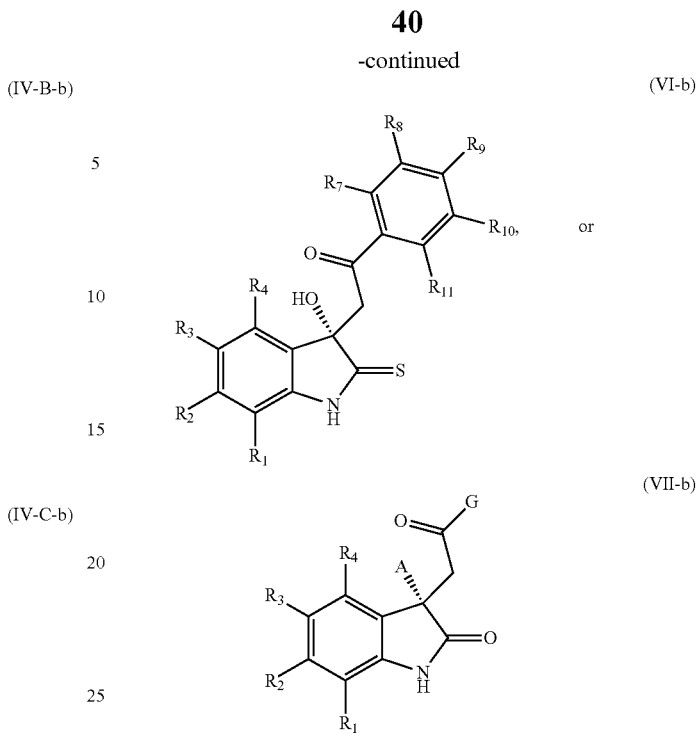

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

Certain Pharmaceutical Compositions

It is generally preferred to administer the inhibitors of preferred embodiments in an intravenous or subcutaneous unit dosage form; however, other routes of administration are also contemplated. Contemplated routes of administration include but are not limited to oral, parenteral, intravenous, and subcutaneous. The inhibitors of preferred embodiments can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice a day, or more.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The inhibitors of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 1 mg or less to about 1,000 mg or more of an inhibitor of the preferred embodiments, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients are advantageously prepared for pulmonary delivery in particulate form with an average particle size of from 0.1 µm or less to 10 µm or more, more preferably from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds of the preferred embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the compounds of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus). In some embodiments, the compounds, compositions and methods provided herein may be in combination with histone deacetylase inhibitors (HDAC), aurora kinase inhibitors, demethylating agents (such as 5-AZA cytidine), immunotherapy with natural killer cells, IGF-IR antibodies, Ewing antigen antibodies, immunosuppressive drugs, and hydroxyurea. Examples of histone deacetylase inhibitors include vorinostat, romidepsin, panobinostat, valproic acid, belinostat, mocetinostat, givinostat, and trichostatin A. Examples of aurora kinase inhibitors include ZM447439, hesperadin, and VX-680. Examples of demethylating agents include 5-azacytidine, 5-azadeoxycytidine, and procaine. Examples of immunosuppressive drugs include 6-mercaptopurine, and azathioprine.

Certain Kits

The compounds of the preferred embodiments can be provided to an administering physician or other health care professional in the form of a kit. The kit is a package which houses a container which contains the compounds in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising compounds of the preferred embodiments in combination with one or more additional chemotherapeutic agents can be provided, or separate pharmaceutical compositions containing an inhibitor of the preferred embodiments and additional therapeutic agents can be provided. The kit can also contain separate doses of a compound of the preferred embodiments for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

Methods of Use

Some embodiments provided herein relate to methods of treating the Ewing's sarcoma family of tumors (ESFT). ESFT contains the unique fusion protein EWS-FLI1. ESFT affects patients between the ages of 3 and 40 years, with most cases occurring in the second decade. Although the embryologic cell type from which ESFT are derived is unknown, the tumor often grows in close proximity to bone, but can occur as a soft-tissue mass. Over 40% of patients who present with localized tumors will develop recurrent disease and the majority of these will die from ESFT, while 75-80% of patients who present with metastatic ESFT will die within 5 years despite high-dose chemotherapy (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). These survival rates have not improved for the past 20 years, even after dose-intensifying chemotherapy. To improve survival and reduce therapy-related morbidity, novel targeted strategies for treating ESFT patients, as provided in the preferred embodiments, can be employed.

ESFT are characterized by a translocation, occurring in 95% of tumors, between the central exons of the EWS gene (Ewing Sarcoma) located on chromosome 22 to the central exons of an ets family gene; either FLI1 (Friend Leukemia Insertion) located on chromosome 11, t(11; 22), or ERG located on chromosome 21, t(21; 22). The EWS-FLI1 fusion transcript encodes a 55 kDa protein (electrophoretic motility of approximately 68 kD) with two primary domains. The EWS domain is a potent transcriptional activator, while the FLI1 domain contains a highly conserved ets DNA binding domain (May W A, Lessnick S L, Braun B S, et al. The Ewing's sarcoma EWS/FLI-1 fusion gene encodes a more potent transcriptional activator and is a more powerful transforming gene than FLI-1. Mol Cell Biol 1993; 13(12): 7393-8); the resulting EWS-FLI1 fusion protein acts as an aberrant transcription factor. EWS-FLI1 transformation of mouse fibroblasts requires both the EWS and FLI1 functional domains to be intact (May W A, Gishizky M L, Lessnick S L, et al. Ewing sarcoma 11; 22 translocation produces a chimeric transcription factor that requires the DNA-binding domain encoded by FLI1 for transformation. Proc Natl Acad Sci USA 1993; 90(12):5752-6).

EWS-FLI1 is an outstanding therapeutic target, in that it is expressed only in tumor cells and is required to maintain the growth of ESFT cell lines. Reduced expression levels of EWS-FLI1 using either antisense oligodeoxynucleotides (ODN) (Toretsky J A, Connell Y, Neckers L, Bhat N K. Inhibition of EWS-FLI-1 fusion protein with antisense oligodeoxynucleotides. J Neurooncol 1997; 31(1-2):9-16; Tanaka K, Iwakuma T, Harimaya K, Sato H, Iwamoto Y. EWS-Fli1 antisense oligodeoxynucleotide inhibits proliferation of human Ewing's sarcoma and primitive neuroectodermal tumor cells. J Clin Invest 1997; 99(2):239-47) or small interfering RNAs (siRNA) (Ouchida M, Ohno T, Fujimura Y, Rao V N, Reddy E S. Loss of tumorigenicity of Ewing's sarcoma cells expressing antisense RNA to EWS-fusion transcripts. Oncogene 1995; 11(6):1049-54; Maksimenko A, Malvy C, Lambert G, et al. Oligonucleotides targeted against a junction oncogene are made efficient by nanotechnologies. Pharm Res 2003; 20(10):1565-7; Kovar H, Aryee D N, Jug G, et al. EWS/FLI-1 antagonists induce growth inhibition of Ewing tumor cells in vitro. Cell Growth Differ 1996; 7(4):429-37) cause decreased proliferation of ESFT cell lines and regression of tumors in nude mice. Recent advances in nanotechnology have improved the delivery and controlled release of siRNA, yet neither antisense ODN nor siRNA reduction of EWS-FLI1 in humans is possible with current technologies (Maksimenko A, Malvy C, Lambert G, et al. Oligonucleotides targeted against a junction oncogene are made efficient by nanotechnologies. Pharm Res 2003; 20(10):1565-7; Lambert G, Bertrand J R, Fattal E, et al. EWS FLI-1 antisense nanocapsules inhibits Ewing sarcoma-related tumor in mice. Biochem Biophys Res Commun 2000; 279(2):401-6). One interesting approach to EWS-FLI1 targeting used comparative expression between siRNA reduced EWS-FLI1 and a library of small molecules, which led to a clinical trial with Ara-C (Stegmaier K, Wong J S, Ross K N, et al. Signature-based small molecule screening identifies cytosine arabinoside as an EWS/FLI modulator in Ewing sarcoma. PLoS medicine 2007; 4(4):e122). This method of identifying Ara-C also indicated doxorubicin and puromycin would reduce EWS-FLI1 levels. Doxorubicin is currently used as standard therapy for ESFT patients and yet, survival is far from acceptable (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). The use of Ara-C in ESFT patients is currently being evaluated in a Phase II trial. While it is hoped that this represents a needed clinical breakthrough, it certainly demonstrates the importance of small molecule targeting of EWS-FLI1. The preferred embodiments provide small molecule protein-protein interaction inhibitors (SMPPII) that disrupt EWS-FLI1 from critical protein partners, thereby achieving tumor specificity and more precise targeting of EWS-FLI1.

EWS-FLI1 is a great therapeutic target since it is only expressed in tumor cells; however, the ability to target this tumor-specific oncogene has previously not been successful. One of the challenges towards small molecule development is that EWS-FLI1 lacks any known enzymatic domains, and enzyme domains have been thought to be critical for targeted therapeutics. In addition, EWS-FLI1 is a disordered protein, indicating that it does not exhibit a rigid structure that can be used for structure based drug design (Uren A, Tcherkasskaya O, Toretsky J A. Recombinant EWS-FLI1 oncoprotein activates transcription. Biochemistry 2004; 43(42):13579-89). In fact, the disordered nature of EWS-FLI1 is critical for its transcriptional regulation (Ng K P, Potikyan G, Savene R O, Denny C T, Uversky V N, Lee K A. Multiple aromatic side chains within a disordered structure are critical for transcription and transforming activity of EWS family oncoproteins. Proc Natl Acad Sci USA 2007; 104(2):479-84). Disordered proteins are considered as more attractive targets for small molecule protein-protein interaction inhibitors specifically because of their biochemical disordered properties (Cheng Y, LeGall T, Oldfield C J, et al. Rational drug design via intrinsically disordered protein. Trends Biotechnol 2006; 24(10):435-42)

EWS-FLI1 binds RNA helicase A in vitro and in vivo. It is believed that protein-protein interactions of EWS-FLI1 may contribute to its oncogenic potential; therefore, novel proteins have been sought that directly interact with and functionally modulate EWS-FLI1. Recombinant EWS-FLI1 that is transcriptionally active (Uren A, Tcherkasskaya O, Toretsky J A. Recombinant EWS-FLI1 oncoprotein activates transcription. Biochemistry 2004; 43(42):13579-89) was used as a target for screening a commercial peptide phage display library. Twenty-eight novel peptides that differentially bind to EWS-FLI1 were identified from phage sequencing. A National Center for Biotechnology Information database search for human proteins homologous to these peptides identified a peptide that was homologous to aa 823-832 of the human RNA helicase A, (RHA, gene bank accession number A47363) (Toretsky J A, Erkizan V, Levenson A, et al. Oncoprotein EWS-FLI1 activity is enhanced by RNA helicase A. Cancer Res 2006; 66(11):5574-81).

While EWS-FLI1 is quite specific to ESFT cells, EWS and RHA are ubiquitously expressed. The region between EWS-FLI1 and RHA are targeted by molecular therapeutics that may have specificity; since EWS-FLI1 is expressed only in tumors and the interaction points with RHA may be unique. Therapeutic agents, namely, small molecule protein-protein interaction inhibitors, are provided herein to inhibit EWS-FLI1 function.

Most translocation-fusion protein sarcomas portend a poor prognosis, including ESFT. The chromosomal translocation t(11; 22), leading to the unique and critical fusion protein EWS-FLI1, is a perfect cancer target. Many other sarcomas share similar translocation variants (Table 2. from Helman L J, Meltzer P. Mechanisms of sarcoma development. Nat Rev Cancer 2003; 3(9):685-94).

EWS-FLI1 translocations have been reported in solid pseudopapillaryneoplasms of the pancreas (Maitra A., et al., Detection of t(11; 22)(q24; q12) translocation and EWS-FLI-1 fusion transcript in a case of solid pseudopapillary tumor of the pancreas. Pediatr Dev Pathol 2000; 3:603-605), however the role of EWS-FLI1 in all solid pseudopapillary neoplasms remains to be resolved (Katharina Tiemann et al., Solid pseudopapillary neoplasms of the pancreas are associated with FLI-1 expression, but not with EWS/FLI-1 translocation).

EWS or FLI1 homologues are partners in translocations that occur in a wide range of sarcomas and leukemias. EWS, or its homologue TLS or FUS, is involved in chromosomal translocations of clear cell sarcoma, myxoid liposarcoma, desmoplastic small round cell tumor, chondrosarcoma and acute myeloid leukemia. FLI1 belongs to the ets family of genes. The FLI1 homologue ERG is translocated in approximately 10% of Ewing's sarcomas and 20% of acute myeloid leukemias. This suggests that EWS-FLI1 can serve as model system that might impact upon a family of diseases (related by translocation partners) that affect a large number of patients (Uren A., Tcherkasskaya O. and Toretsky J. A. Recombinant EWS-FLI1 oncoprotein activates transcription. Biochemistry 43(42) 13579-89 (2004)).

ERG is also translocated in prostate cancer, where the TMPRSS2:ERG fusion suggests a distinct molecular subtype that may define risk for disease progression (F. Demichelis et al., TMPRSS2:ERG gene fusion associated with lethal cancer in a watchful waiting cohort. Oncogene (2007) 26, 4596-4599). Other diseases where translocations of EWS or FLI1 family members have been observed include prostate cancer, glioblastoma, acute myeloid leukemia, breast cancer, head & neck cancer, melanoma, non-small cell lung cancer, ovarian cancer, and uterine cancer (Janknecht, Ralf; Shin, Sook, and Oh, Sangphil, ETV1, 4 and 5: An Oncogenic Subfamily of ETS Transcription Factors. Biochim. Biophys. Acta 1826 (1), 1-12 (2012)).

Therefore, the therapeutic agents of the preferred embodiments have potential for application in many other tumors. More broadly, some of the most difficult leukemias also have translocation-generated fusion proteins involving the mixed-lineage leukemia gene (MLL, 11q23), and our work could serve as a paradigm for a very treatment-resistant group of cancers (Pui C H, Chessells J M, Camitta B, et al. Clinical heterogeneity in childhood acute lymphoblastic leukemia with 11q23 rearrangements. Leukemia 2003; 17(4):700-6.). Thus embodiments include cancers where translocations have occurred. Translocation fusion genes are listed in TABLE 1.

TABLE 1

| Ewing's sarcoma | | |
|---|---|---|
| Translocation | Genes | Type of fusion gene |
| t(11;22)(q24;q12) | EWSR1-FLI1 | Transcription factor |
| t(21;22)(q22;q12) | EWSR1-ERG | Transcription factor |
| t(7;22)(p22;q12) | EWSR1-ETV1 | Transcription factor |
| t(17;22)(q21;q12) | EWSR1-ETV4 | Transcription factor |
| t(2;22)(q33;q12) | EWSR1-FEV | Transcription factor |

A number of disorders include overexpression of an ETS gene, or an ETS gene fusion, that is, a gene translocation that includes an ETS gene. Examples of such ETS genes include FLI1, ERG, ETV1, and ETV4. Examples of fusion genes include EWS-FLI, TMPRSS2-ERG. TABLE 2 lists several cancers in which one or more ETS gene family members are overexpressed, and/or are rearranged.

TABLE 2

| | Tumors with ETS overexpression | ETS member | | | |
|---|---|---|---|---|---|
| Cancer | or gene fusion | FLI1 | ERG | ETV1 | ETV4 |
| Prostate | 41% | 2% | 25% | 10% | 6% |
| Melanoma | 34% | 8% | 8% | 20% | 5% |
| Non-small-cell lung carcinoma | 33% | 12% | 8% | 12% | 5% |
| Uterine | 25% | 6% | 9% | 11% | 6% |

TABLE 2-continued

| Cancer | Tumors with ETS overexpression or gene fusion | ETS member | | | |
| --- | --- | --- | --- | --- | --- |
| | | FLI1 | ERG | ETV1 | ETV4 |
| Head and Neck | 24% | 6% | 4% | 7% | 9% |
| Ovarian | 21% | 7% | 3% | 10% | 3% |
| Glioblastoma multiforme | 19% | 7% | 4% | 7% | 4% |
| Acute myeloid leukemia | 19% | 8% | 8% | 4% | 2% |
| Breast | 18% | 5% | 4% | 5% | 7% |

Indications

Certain compounds, compositions and methods provided herein can be used to treat a number of disorders such as a tumor or tumor cell comprising a translocation gene fusion, such as those listed in TABLE 1, Ewing's sarcoma, prostate cancer, glioblastoma, acute myeloid leukemia, breast cancer, head & neck cancer, melanoma, non-small cell lung cancer, ovarian cancer, and uterine cancer. Some embodiments of the methods provided herein include a method for inhibiting proliferation of a cell. In some embodiments, the cell overexpresses an ETS gene. In some embodiments, the overexpressed ETS gene can include FLI1, ERG, ETV1, or ETV4. In some embodiments, the cell comprises an ETS fusion gene. In some embodiments, the ETS fusion gene can include an ETS gene such as FLI1, ERG, ETV1, and ETV4.

The ETS family of transcription factors is critical for development, differentiation, proliferation, and plays an important role in apoptosis and tissue remodeling. Transcriptional consequences of ETS protein deregulation by overexpression, gene fusion, and modulation by RAS/MAPK and PI3K signaling are linked to alterations in normal cell functions, and lead to increased proliferation, sustained angiogenesis, invasion, and metastasis. Overexpressed ETS proteins and ETS family fusion proteins have been reported in acute myeloid leukemia (AML) and diffuse large B cell lymphoma (DLBCL). In DLBCL, the 11q24.3 region has been identified as a recurrent lesion and a contributor to the pathogenesis of disease, leading to the deregulation of ETS family members, ETS1 and FLI. Additionally, in AML, the overexpression and translocations of ERG, an ETS family member, has been shown to be associated with poor prognosis in complex or normal karyotypes.

Compounds of Formulae (I)-(VII) may directly bind EWS-FLI1 inhibiting the biological activity of ETS-family transcription factor oncoproteins and may be employed in treating patients with Ewing sarcoma. The EWS1-FLI1 is a fusion protein that has been shown to be the driver of Ewing Sarcoma (ES). Compounds of Formulae (I)-(VII) may block the binding between EWS-FLI1 and RNA helicase A, may show a transcriptional decrease in COS7 cells transfected with a EWS-FLI1 responsive promoter ($EC_{50}$<100 nM), and may inhibit the proliferation of A4573 cells (EWS-FLI1 expressing Ewing sarcoma cell line) at nanomolar concentrations ($EC_{50}$<200 nM).

Compounds of Formulae (I)-(VII) may also have antiproliferative effects, may cause cell cycle arrest, and may induce apoptosis in AML and DLBCL cell lines with deregulated ETS family members. Upregulation of FLI1 and/or ERG ETS family members may be observed in myeloid cell lines (e.g., HL60, Kasumi-1, ML-2, MOLM-13, and MOLM-16). Treatment with compounds of Formulae (I)-(VII) may show a decrease in cellular viability and induced dose-dependent apoptosis of cells at 48 hours. In DLBLC cell lines (e.g., TMD8, HBL1, U2932, DOHH2, WSUDLCL2, and OCI-Ly18), treatment with compounds of Formulae (I)-(VII) may result in a decrease in cellular proliferation and an increase in apoptosis. In vivo efficacy studies in xenograft models of DLBCL may indicate antitumor activity, and may confirm the utility and efficacy of compounds of Formulae (I)-(VII) in the treatment of AML and DLBCL by targeting the aberrant expression and translocations in the ETS-family of transcription factors, which contribute to the pathogenesis of the disease.

EXAMPLES

A number of analogs were prepared having structures as in the compounds of Formulae (I)-(VII). Compounds were identified using NMR, mass spectrocopy analysis, and chromatographical purification by UPLC and LCMS. Structures complied with NMR analysis. The structure, mass "[M+H]+" derived from mass spectroscopy analysis, chromatographical purity by UPLC (wt. %), and chromatographical purity by LCMS (wt. %) for these analogs are provided in TABLE 3.

TABLE 3

| Compound | [M + H]+ | Chromatographical purity | | Structure |
| --- | --- | --- | --- | --- |
| | | UPLC | LCMS | |
| TK Analog 2 | 392.07 | 97.89 | 99.67 | 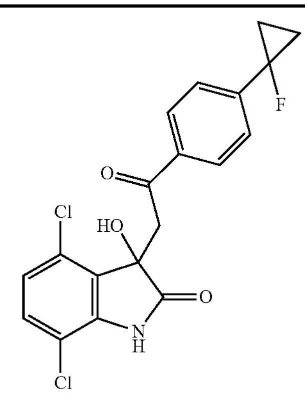 |

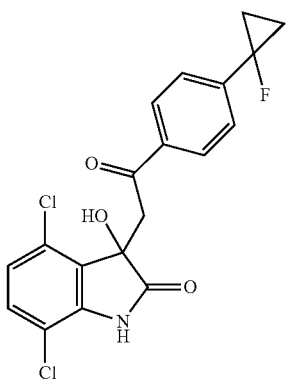

Analogue-2

TABLE 3-continued
| Compound | [M + H]+ | Chromatographical purity | | Structure |
| --- | --- | --- | --- | --- |
| | | UPLC | LCMS | |
| TK Analog 3 | 391.30 | 96.13 | 97.37 | 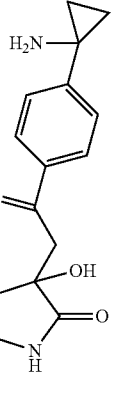 |
| TK Analog 4 | 402.21 | 99.69 | 99.82 | 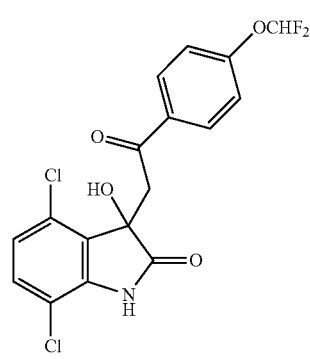<br>Analogue-4 |
| TK Analog 5 | 360.25 | 99.41 | 99.79 | 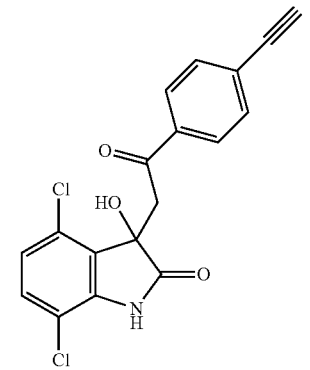 [SMILES: C#Cc1ccc(C(=O)CC2(O)C(=O)Nc3c(Cl)ccc(Cl)c32)cc1] |

TABLE 3-continued

| Compound | [M + H]⁺ | Chromatographical purity | | Structure |
|---|---|---|---|---|
| | | UPLC | LCMS | |
| TK Analog 6 | 350.25 | 98.14 | 98.00 | 3-(2-(4-methoxyphenyl)-2-oxoethyl)-4,7-dichloroindolin-2-one |
| TK Analog 7 | 368.22 | 99.19 | 98.58 | 3-fluoro-3-(2-(4-methoxyphenyl)-2-oxoethyl)-4,7-dichloroindolin-2-one |
| TK Analog 8 | 365.25 | 99.27 | 99.10 | 3-amino-3-(2-(4-methoxyphenyl)-2-oxoethyl)-4,7-dichloroindolin-2-one |
| TK Analog 9 | 376.23 | 99.19 | 99.68 | 3-(2-(benzofuran-5-yl)-2-oxoethyl)-3-hydroxy-4,7-dichloroindolin-2-one |

TABLE 3-continued
| Compound | [M + H]+ | Chromatographical purity | | Structure |
| | | UPLC | LCMS | |
|---|---|---|---|---|
| TK Analog 10 | 392.18 | 99.32 | 99.56 | 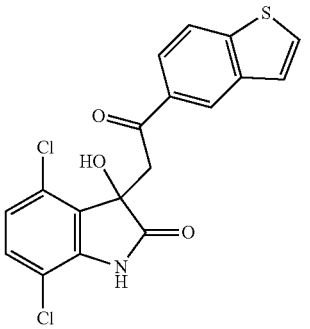 Analogue-10 |
| TK Analog 11 | 375.22 | 97.54 | 97.87 | 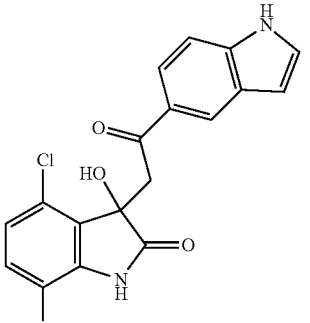 |
| TK-100-OCD3 | 355 | — | — | 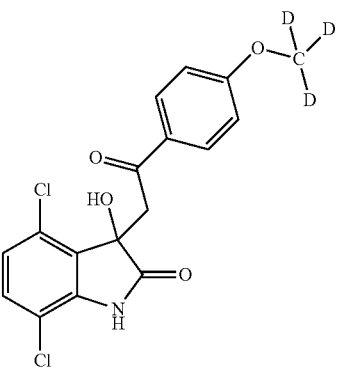 [SMILES: [2H]C([2H])([2H])Oc1ccc(C(=O)CC2(O)C(=O)Nc3c(Cl)ccc(Cl)c32)cc1] |
| TK Analog 13 | 409.30 | 98.27 | 98.94 | 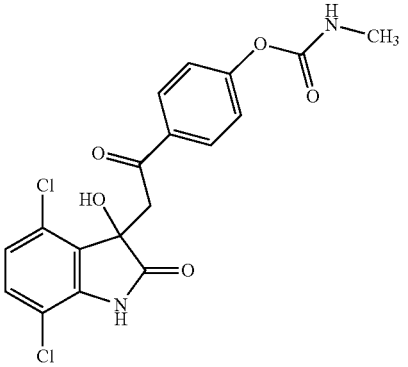 Analogue 13 |

TABLE 3-continued
| Compound | [M + H]+ | Chromatographical purity | | Structure |
| | | UPLC | LCMS | |
|---|---|---|---|---|
| TK Analog 14 | 357.27 | 98.13 | 97.72 | 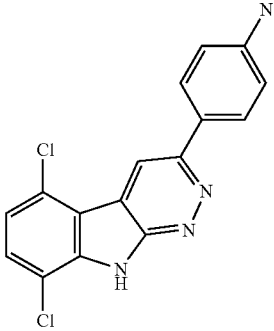<br>Analogue-14 |
| TK Analog 15A | 384.27 | 97.05 | 97.86 | 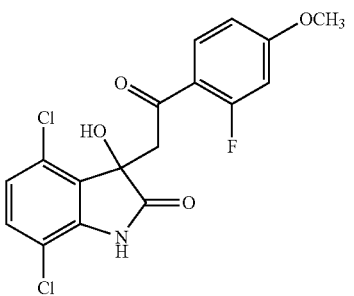<br>Analogue-15A |
| TK Analog 16 | 378.24 | 98.10 | 99.03 | 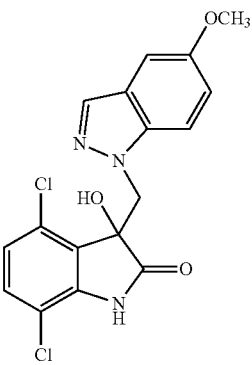<br>Analogue-16 |
| TK Analog 16A | 378.24 | 99.35 | 98.70 | 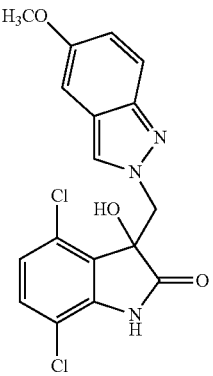<br>Analogue-16A |

TABLE 3-continued
| Compound | [M + H]+ | Chromatographical purity | | Structure |
|---|---|---|---|---|
| | | UPLC | LCMS | |
| TK Analog 17 | 379.23 | 99.12 | 97.32 | 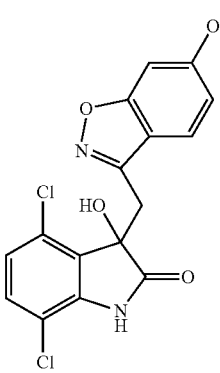 Analogue-17 |
| TK Analog 18 | 395.22 | 96.56 | 97.81 | 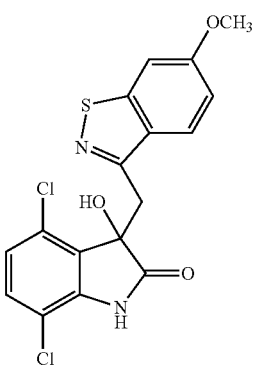 Analogue-18 |
| TK Analog 19 | 386.1 | 99.25 | 99.76 | 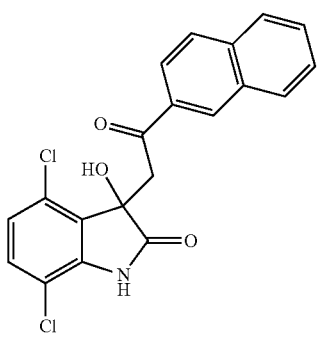 Analog-19 |

TABLE 3-continued
| Compound | [M + H]+ | Chromatographical purity | | Structure |
|---|---|---|---|---|
| | | UPLC | LCMS | |
| TK Analog 20 | 377.0 | 97.64 | 96.62 | 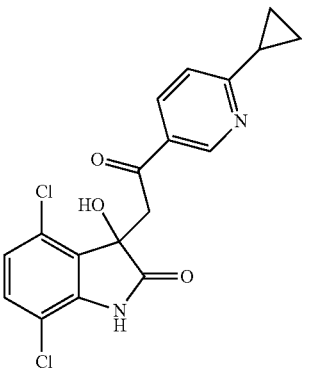<br>Analog-20 |
| TK Analog 21 | 377.1 | 99.18 | 99.68 | 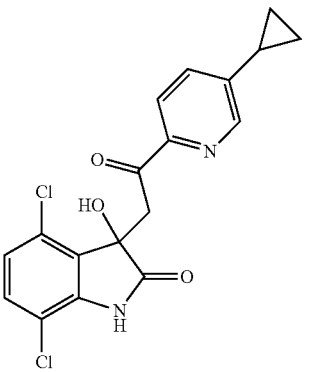<br>Analog-21 |
| TK Analog 22 | 382.0 | 97.01 | 96.86 | 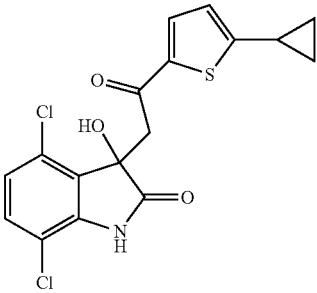<br>Analog-22 |
| TK Analog 23 | 382.1 | 98.01 | 98.46 | 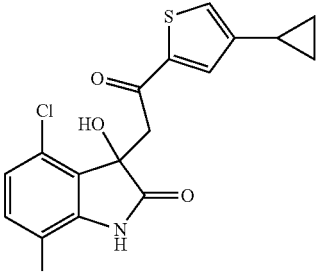<br>Analog-23 |

TABLE 3-continued

| Compound | [M + H]+ | Chromatographical purity UPLC | LCMS | Structure |
|---|---|---|---|---|
| TK Analog 24 | 382.0 | 96.75 | 95.76 | 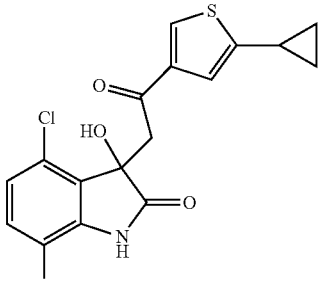<br>Analog-24 |

Examples—Cell Growth Studies

A modified tetrazolium salt assay using the CCK-8 kit (Sigma-Aldrich; St Louis, Mo.) was used to measure the inhibition of human tumor cell growth. Tumor cells (5000-7500 per well) were added to 96 well plates and allowed to attach for 4-5 hours. Compounds were serially diluted and added in triplicate at a concentration of 0.02 to 5 µM. DMSO was included as a vehicle control. Cells were incubated in the presence of compound for 3 days. After incubation CCK-8 reagent was added to each well and incubated for 2-4 hours. Viable cells were quantitated spectrophotometrically at a wavelength of 450 nm. Percent viability of each sample was calculated from the A450 values as follows: % viability=(A450 nm sample/A450 nm DMSO-treated cells×100). The $IC_{50}$ was defined as the concentration that gave rise to 50% inhibition of cell viability. $IC_{50}$ activities of particular compounds were determined using SKES (type 2, 7/5) cells (Ewing Sarcoma cell line), TC71 (Type 1, 7/6) cells (Ewing Sarcoma cell line), and A4573 (Type 3, 10/6) cells (Ewing Sarcoma cell line). The small molecule YK-4-279 (4,7-dichloro-3-hydroxy-3-(2-(4-methoxyphenyl)-2-oxoethyl)indolin-2-one) inhibits binding of EWS1-FLI1 fusion protein to RHA with growth arrest and apoptosis in Ewing sarcoma cells, and exhibits in vitro anti-lymphoma activity. TK-216 is a YK-4-279 clinical derivative that is in phase 1 for patients with relapsed or refractory Ewing sarcoma. Preclinical testing has been conducted for TK-216 in lymphoma models. Test results for the analogs were compared to those for TK-216 and YK-4-279. Results are summarized in TABLE 4.

TABLE 4

| Compound | TC71 IC50 (µM) | SKES IC50 (µM) | A4573 IC50 (µM) |
|---|---|---|---|
| YK-4-279 | <5 | <5 | <5 |
| TK-216-2 | <5 | <5 | <5 |
| TK Analog 2 | <5 | <5 | <5 |
| TK Analog 3 | >5 | <5 | >5 |
| TK Analog 4 | >5 | >5 | >5 |
| TK Analog 5 | >5 | >5 | >5 |
| TK Analog 6 | <5 | <5 | <5 |
| TK Analog 7 | <5 | <5 | <5 |
| TK Analog 8 | >5 | <5 | >5 |
| TK Analog 9 | >5 | >5 | >5 |
| TK Analog 10 | <5 | <5 | <5 |

TABLE 4-continued

| Compound | TC71 IC50 (µM) | SKES IC50 (µM) | A4573 IC50 (µM) |
|---|---|---|---|
| TK Analog 11 | <5 | <5 | <5 |
| TK-100-OCD3 | <5 | <5 | <5 |
| TK Analog 13 | >5 | >5 | >5 |
| TK Analog 14 | >5 | >5 | >5 |
| TK Analog 15A | <5 | <5 | <5 |
| TK Analog 16 | >5 | <5 | >5 |
| TK Analog 16A | >5 | >5 | >5 |
| TK Analog 17 | >5 | >5 | >5 |
| TK Analog 18 | >5 | <5 | >5 |
| TK Analog 19 | <5 | <5 | <5 |
| TK Analog 20 | >5 | >5 | >5 |
| TK Analog 21 | >5 | >5 | >5 |
| TK Analgo 22 | >5 | <5 | >5 |
| TK Analog 23 | >5 | >5 | >5 |
| TK Analog 24 | >5 | >5 | >5 |

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein and in the Appendix are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A compound having Formula (IV-A), (IV-B), (IV-C), or (IV-D):

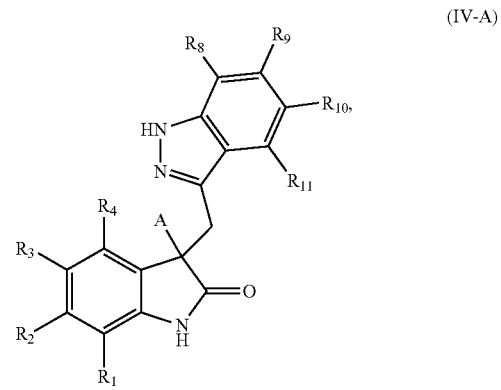

(IV-A)

-continued

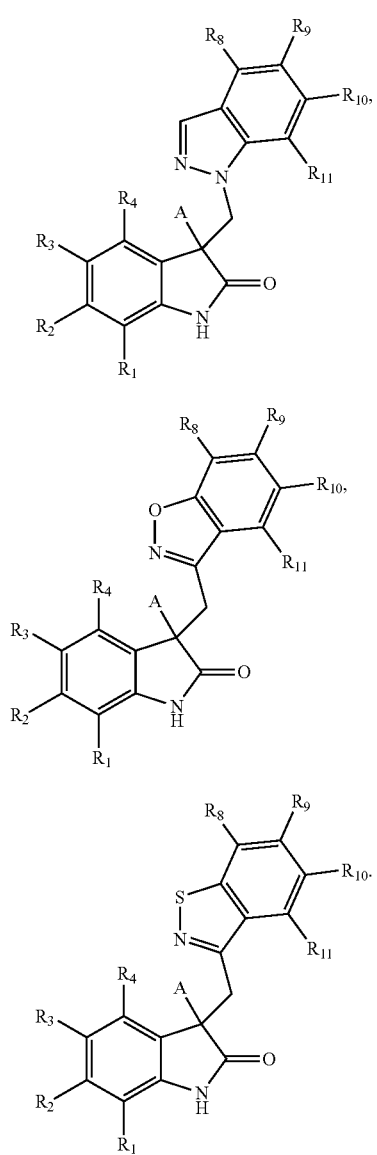

or a stereoisomer, a pharmaceutically acceptable salt, or solvate thereof, wherein A is selected from the group consisting of —OH, D, H, F, and —NH$_2$; wherein R$_1$, R$_2$, R$_3$, and R$_4$ are independently selected from the group consisting of H, Cl, —CN, —CF$_3$, C$_{1-6}$ alkyl, C$_{1-6}$ alkoxy, —C(=O)NH$_2$, —NO$_2$, —NH$_2$, and —OH; and wherein R$_8$, R$_9$, R$_{10}$ and R$_{11}$ are independently selected from the group consisting of H, D, F, Cl, halogen, CN, CF$_3$, C$_{1-6}$ alkyl, aryl, heteroaryl, —O(aryl), —O(heteroaryl), —CO$_2$H, —CO$_2$(C$_{1-6}$ alkyl), —NHSO$_2$(C$_{1-6}$ alkyl), —NHSO$_2$(aryl), —NHCONH(C$_{1-6}$ alkyl), —NHCON(C$_{1-6}$ alkyl)$_2$, —N(C$_{1-6}$ alkyl)CONH$_2$, —N(C$_{1-6}$ alkyl)CONH(C$_{1-6}$ alkyl), —N(C$_{1-6}$ alkyl)CON(C$_{1-6}$ alkyl)$_2$, —SO$_2$(C$_{1-6}$ alkyl), —SO$_2$NH$_2$, —SO$_2$NH(C$_{1-6}$ alkyl), —SO$_2$N(C$_{1-6}$ alkyl)$_2$, C$_{3-8}$ cycloalkyl, and C$_{3-8}$ heterocycloalkyl.

2. The compound of claim 1, wherein R$_1$, R$_2$, R$_3$, and R$_4$ are independently selected from the group consisting of H and Cl.

3. The compound of claim 1, wherein R$_1$ and R$_4$ are Cl and R$_2$ and R$_3$ are H.

4. The compound of claim 1, wherein A is —OH.

5. The compound of claim 1, wherein R$_8$, R$_{10}$, and R$_{11}$ are H.

6. A compound, which has a Formula (IV-15), (IV-16), (IV-17), or (IV-18):

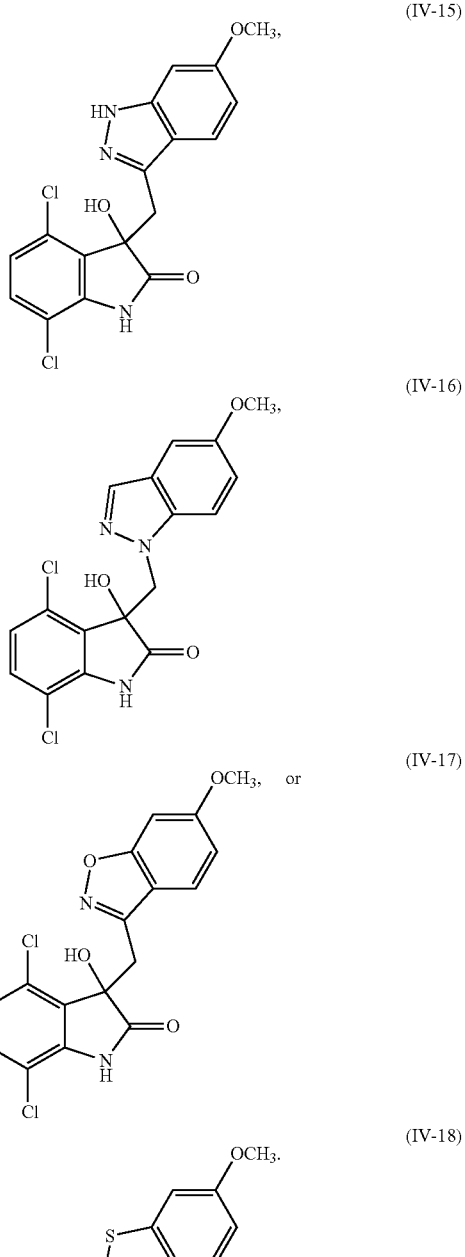

7. A method for treating cancer selected from the group consisting of Ewing's sarcoma, prostate cancer, glioblastoma, acute myeloid leukemia, breast cancer, head and neck cancer, melanoma, non-small cell lung cancer, ovarian cancer, and uterine cancer, comprising:

administering an effective amount of the compound of claim 1, to a subject in need thereof.

8. A method for killing or inhibiting the growth of a neoplastic cell, wherein the neoplastic cell is a cancer cell, the cancer being selected from the group consisting of Ewing's sarcoma, prostate cancer, glioblastoma, acute myeloid leukemia, breast cancer, head & neck cancer, melanoma, non-small cell lung cancer, ovarian cancer, and uterine cancer, comprising:

contacting the neoplastic cell with an effective amount of the compound of claim 1.

9. A method for inhibiting proliferation of a cell, wherein the cell overexpresses an ETS gene or comprises an ETS fusion gene, comprising:

contacting the cell with an effective amount of the compound of claim 1.

10. The method of claim 9, wherein the ETS gene or the ETS fusion gene is selected from the group consisting of FLI1, ERG, ETV1, and ETV4.

* * * * *

UNITED STATES PATENT AND TRADEMARK OFFICE
CERTIFICATE OF CORRECTION

PATENT NO. : 9,822,122 B2
APPLICATION NO. : 15/461327
DATED : November 21, 2017
INVENTOR(S) : Stephen E. Webber It is certified that error appears in the above-identified patent and that said Letters Patent is hereby corrected as shown below:

In Column 2 (item (56)) at Line 28, Under Other Publications, change "adol" to --aldol--.

In Column 2 (item (56)) at Line 35, Under Other Publications, change "5'-pyrazonlin)" to --5'-pyrazolin)--.

In Column 2 (item (56)) at Line 46, Under Other Publications, change "Benzailide" to --Benzanilide--.

In Column 2 (page 2, item (56)) at Line 21, Under Other Publications, change "blocing oncongenic" to --blocking oncogenic--.

In Column 2 (page 2, item (56)) at Line 48, Under Other Publications, change "Classsification" to --Classification--.

In Column 2 (page 2, item (56)) at Line 53, Under Other Publications, change "hyroxy" to --hydroxy--.

In Column 1 (page 3, item (56)) at Line 3, Under Other Publications, change "Josh" to --Joshi--.

In Column 1 (page 3, item (56)) at Line 3, Under Other Publications, change "Hetercycles:" to --Heterocycles:--.

In Column 1 (page 3, item (56)) at Line 4, Under Other Publications, change "Fluroinated" to --Fluorinated--.

In Column 1 (page 3, item (56)) at Line 8, Under Other Publications, change "3-Aroylmethyleneindolin" to --3-Arylmethyleneindolin--.

In Column 1 (page 3, item (56)) at Line 20, Under Other Publications, change "Appreviated" to --Abbreviated--.

Signed and Sealed this
Twenty-sixth Day of June, 2018

Andrei Iancu
*Director of the United States Patent and Trademark Office*

CERTIFICATE OF CORRECTION (continued)

In Column 1 (page 3, item (56)) at Line 21, Under Other Publications, change "Recommentations" to --Recommendations--.

In Column 1 (page 3, item (56)) at Line 24, Under Other Publications, change "Sciene" to --Science--.

In Column 1 (page 3, item (56)) at Line 24, Under Other Publications, change "(2006) 94" to --(2006)--.

In Column 1 (page 3, item (56)) at Line 31, Under Other Publications, change ""NROB1" to --"NR0B1--.

In Column 2 (page 3, item (56)) at Line 5, Under Other Publications, change "3-hyrdrozyoxindoles"" to --3-hydroxyoxindoles"--.

In Column 2 (page 3, item (56)) at Line 7, Under Other Publications, change "Alkyidene" to --Alkadiene--.

In Column 2 (page 3, item (56)) at Line 10, Under Other Publications, change "Tetrahetron" to --Tetrahedron--.

In Column 2 (page 3, item (56)) at Line 13, Under Other Publications, change "acrykuc" to --acrylic--.

In Column 2 (page 3, item (56)) at Line 38, Under Other Publications, change ".nik." to --.nih.--.

In Column 2 (page 3, item (56)) at Line 44, Under Other Publications, change "Ewing's i ;'sarcoma," to --Ewing's sarcoma,--.

In Column 2 (page 3, item (56)) at Line 47, Under Other Publications, change "benigh" to --benign--.

In Column 2 (page 3, item (56)) at Line 48, Under Other Publications, change "i Clin" to --Clin--.

In Column 2 (page 3, item (56)) at Line 58, Under Other Publications, change "assocation" to --association--.

In Column 2 (page 3, item (56)) at Line 61, Under Other Publications, change "132 fusion" to --fusion--.

In Column 2 (page 3, item (56)) at Line 63, Under Other Publications, change "(PubChm" to --(PubChem--.

In Column 1 (page 4, item (56)) at Line 6, Under Other Publications, change "137 Pagliaro" to --Pagliaro--.

In Column 1 (page 4, item (56)) at Line 10, Under Other Publications, change "Keytones," to --Ketones,--.

CERTIFICATE OF CORRECTION (continued)
U.S. Pat. No. 9,822,122 B2

In Column 1 (page 4, item (56)) at Line 41, Under Other Publications, change "149;421578-89-4;" to ---421578-89-4;--.

In Column 1 (page 4, item (56)) at Line 54, Under Other Publications, change ""Heterodiene Syntheses." to --"Heterodyne Synthesis.--.

In Column 1 (page 4, item (56)) at Line 63, Under Other Publications, change "-oxoehyl]," to -- -oxoethyl],--.

In Column 1 (page 4, item (56)) at Line 66, Under Other Publications, change "-oxoethy1]" to -- -oxoethyl]--.

In Column 1 (page 4, item (56)) at Line 69, Under Other Publications, change "4-dimethoxyphenyI)" to --4-dimethoxyphenyl)--.

In Column 2 (page 4, item (56)) at Line 2, Under Other Publications, change "-trimethoxphenyl)" to -- -trimethoxyphenyl)--.

In Column 2 (page 4, item (56)) at Line 5, Under Other Publications, change "ethylpheny1)" to --ethylphenyl)--.

In Column 2 (page 4, item (56)) at Line 7, Under Other Publications, change "-oxoethy1]" to -- -oxoethyl]--.

In Column 2 (page 4, item (56)) at Line 10, Under Other Publications, change "dimethoxypheny1)-2 oxoethy1)" to --dimethoxyphenyl)-2-oxoethyl)--.

In Column 2 (page 4, item (56)) at Line 12, Under Other Publications, change "Antioselective" to --Enantioselective--.

In Column 2 (page 4, item (56)) at Line 12, Under Other Publications, change "3-Hyrdoxy" to --3-Hydroxy--.

In Column 2 (page 4, item (56)) at Line 14, Under Other Publications, change "Trifuoromethyl" to --Trifluoromethyl--.

In Column 2 (page 4, item (56)) at Lines 22-23, Under Other Publications, change ":18:3152-3157" to --18:3152-3157--.

In Column 2 (page 5, item (56)) at Line 8, Under Other Publications, change "Neucleophilic" to --Nucleophilic--.

In Column 2 (page 5, item (56)) at Line 9, Under Other Publications, change "Flourine" to --Fluorine--.

CERTIFICATE OF CORRECTION (continued)

In Column 2 (page 5, item (56)) at Line 28, Under Other Publications, change "-spirocycline" to -- -spirocyclic--.

In Column 8 at Line 27, After "invention" insert --.--.

In Column 9 at Line 8 (approx.), After " 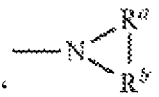 " insert --.--.

In Column 10 at Line 27, Change "thioimides" to --thioamides--.

In Column 10 at Line 29, Change "heterocycloalky" to --heterocycloalkyl--.

In Column 10 at Line 42, Change "pyrrolidione," to --pyrrolidinone,--.

In Column 10 at Line 61, Change "p-toluensulfonic," to --p-toluenesulfonic,--.

In Column 12 at Line 33, Change "—N($C_{1-6}$alkyl" to -- —N($C_{1-6}$ alkyl--.

In Column 16 at Line 6, Change "—N($C_{1-6}$alkyl" to -- —N($C_{1-6}$ alkyl--.

In Column 18 at Line 55 (approx.), Change "$C_{3-8}$ heterocycloalkyl." to --$C_{3-8}$ heterocycloalkyl.--.

In Column 38 at Lines 34-47 (approx.), Change " 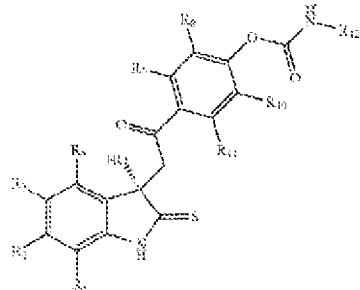 " to -- 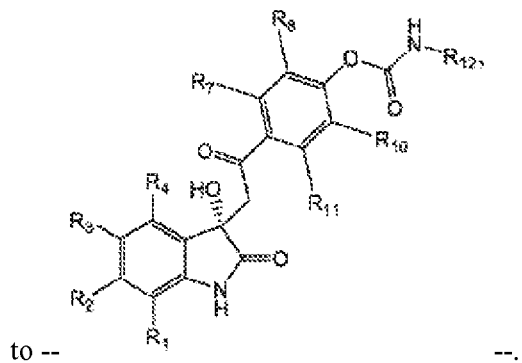 --.

In Column 41 at Line 37, Change "spheroblasts." to --spheroplasts.--.

In Column 42 at Line 47, Change "ultramylopectin," to --ultraamylopectin,--.
In Column 43 at Line 12, Change "providone" to --povidone--.

CERTIFICATE OF CORRECTION (continued)
U.S. Pat. No. 9,822,122 B2

In Column 43 at Line 15, After "doses" insert --.--.

In Column 45 at Line 2, Change "actinomyocin" to --actinomycin--.

In Column 45 at Line 2, Change "mithomycin" to --mitomycin--.

In Column 47 at Line 26, After "24(10):435-42)" insert --.--.

In Column 47 at Line 40, Change "aa" to --a--.

In Column 50 at Line 38, Change "spectrocopy" to --spectroscopy--.

In Column 64 at Line 35 (approx.), Change "Analgo" to --Analog--.